(12) United States Patent
Hoffman

(10) Patent No.: US 6,723,055 B2
(45) Date of Patent: Apr. 20, 2004

(54) SYSTEM FOR MEASURING RESPIRATORY FUNCTION

(75) Inventor: Andrew Hoffman, Boston, MA (US)

(73) Assignee: Trustees of Tufts College, Boston, MA (US)

( * ) Notice: Subject to any disclaimer, the term of this patent is extended or adjusted under 35 U.S.C. 154(b) by 0 days.

(21) Appl. No.: 09/950,318

(22) Filed: Sep. 10, 2001

(65) Prior Publication Data

US 2002/0120207 A1 Aug. 29, 2002

Related U.S. Application Data

(63) Continuation-in-part of application No. 09/298,352, filed on Apr. 23, 1999, now Pat. No. 6,287,264.

(51) Int. Cl.[7] ............................................. A61B 5/00
(52) U.S. Cl. ................................................... 600/538
(58) Field of Search ................................... 600/533–8

(56) References Cited

U.S. PATENT DOCUMENTS

| | | | |
|---|---|---|---|
| 2,569,849 A | 10/1951 | Emerson | 128/2.08 |
| 2,970,041 A | 1/1961 | Burlis | 23/256 |
| 3,511,237 A | 5/1970 | Jaeger | 128/2.08 |
| 3,621,833 A | 11/1971 | Crane | 128/2.08 |
| 3,677,261 A | 7/1972 | Day | 128/2.1 Z |
| 4,036,217 A | 7/1977 | Ito et al. | 128/2.08 |
| 4,036,222 A | 7/1977 | Gillard et al. | 128/2.08 |
| 4,305,400 A | 12/1981 | Logan | 128/670 |
| 4,314,563 A | 2/1982 | Wheeler | 128/693 |
| 4,493,692 A | 1/1985 | Reed | 604/4 |
| 4,671,297 A | 6/1987 | Schulze, Jr. | 128/716 |
| 4,777,962 A | 10/1988 | Watson et al. | 128/716 |
| 4,796,639 A | 1/1989 | Snow | 128/719 |
| 4,960,118 A | 10/1990 | Pennock | 128/200 |
| 5,038,773 A | 8/1991 | Norlien et al. | 128/205 |
| 5,273,036 A | 12/1993 | Kronberg et al. | 128/633 |
| 5,308,310 A | 5/1994 | Roff et al. | 600/21 |
| 5,316,010 A | 5/1994 | Brown | 128/721 |
| 5,331,968 A | 7/1994 | Williams et al. | 128/721 |
| 5,379,777 A | 1/1995 | Lomask | 128/716 |
| 5,419,326 A | 5/1995 | Harnoncourt | 128/660.02 |
| 5,513,647 A | 5/1996 | Castile | 128/720 |

(List continued on next page.)

FOREIGN PATENT DOCUMENTS

| | | |
|---|---|---|
| FR | 2294677 | 7/1976 |
| WO | WO 97/32619 | 9/1997 |
| WO | WO 97/50049 | 12/1997 |
| WO | WO 98/41146 | 9/1998 |

OTHER PUBLICATIONS

Lindberg, L. G. et al, "Monitoring of respiratory and heart rates using a fibre–optic senson," Medical & Biological Engineering & Computing, 533–537 (Sep. 1992).

(List continued on next page.)

Primary Examiner—Robert L. Nasser
(74) Attorney, Agent, or Firm—Bowditch & Dewey, LLP

(57) ABSTRACT

The present invention relates to a system for measuring respiratory function of living organisms. More particularly, signals indicative of the change in lung volume, defined as active and passive work, required to breathe and the airflow through the respiratory system of the living organism are obtained and processed as waveforms to provide a signal indicative of the respiratory restriction. The methods of the present invention measure clinical forms of airway obstruction, airway reactivity and lung volume and may be used to continuously or intermittently monitor patients with compromised respiratory function. In a preferred embodiment, a head-out, breath in respiratory plethysmograph system provides the signals indicative of change in lung volume as related to pressure changes in a chamber. Further, flowmetric variables are generated that provide a characterization of airway obstructions.

51 Claims, 56 Drawing Sheets

U.S. PATENT DOCUMENTS

| | | | |
|---|---|---|---|
| 5,513,648 A | 5/1996 | Jackson | 128/721 |
| 5,520,192 A | 5/1996 | Kitney et al. | 128/716 |
| 5,522,397 A | 6/1996 | Vermaak | 128/720 |
| 5,582,182 A | 12/1996 | Hillsman | 128/716 |
| 5,598,838 A | 2/1997 | Servidio et al. | 128/204 |
| 5,680,871 A | 10/1997 | Ganshorn | 128/204 |
| 5,709,202 A | 1/1998 | Lloyd et al. | 128/200.14 |
| 5,810,741 A | 9/1998 | Essen-Moller | 600/529 |
| 5,857,459 A | 1/1999 | Snow et al. | 128/204 |
| 5,944,680 A | 8/1999 | Christopherson et al. | 600/42 |
| 5,980,463 A | 11/1999 | Brockway et al. | 600/485 |
| 5,984,872 A | 11/1999 | Vriend | 600/529 |
| 6,113,550 A | 9/2000 | Wilson | 600/534 |
| 6,183,423 B1 | 2/2001 | Gaumond et al. | 600/529 |
| 6,287,264 B1 | 9/2001 | Hoffman | 600/538 |

OTHER PUBLICATIONS

Pennock, B. E., et al., *A Noninvasive Technique for Measurement of Changes in Specific Airway Resistance*, 1999 The American Physiological Society pps. 399–406.

Dorsch, W., et al., *Continuous Recording of Intrapulmonary "Compressed Air" as a Sensitive Noninvasive Method of Measuring Bronchial Obstruction in Guinea Pigs*, Pflugers Archiv, pps. 236–241.

Silbaugh, S. A., et al., *Noninvasive detection of airway constriction in awake guinea pigs*, The American Physiological Society pps 1666–1669.

Gonzalez, H., *Accuracy of Respiratory Inductive Plethysmograph Over Wide Range of Rib Cage and Abdominal Compartmental Contributions to Tidal Volume in Normal Subjects and in Patients with Chronic Obstructive Pulmonary Disease*, pps. 171–174.

Stick, Stephen, *Measurements During Tidal Breathing*, 1996 Wiley–Liss, Inc., pps. 117–138.

Adams, Jose Antonio, *Respiratory Inductive Plethysmography*, 1996 Wiley–Liss, Inc., pps. 139–164.

Adams, A., et al., *Tidal Volume Measurements in Newborns Using Respiratory Inductive Plethysmography*, 1993 American Review of Respiratory Disease. Vol 148, pps. 585–588.

Davis C; Mazzolini A; Mills J; Dargaville P. *A New Sensor for monitoring chest wall motion during high–frequency oscillatory ventilation*. Med Eng Phys, Nov. 1999, 21(9):619–23.

Alverti A; Dellaca R; Pelosi P; Chiumello D; Pedotti A; Gattinoni L. *Optoelectronics Plethysmography in Intensive Care Patients*. Am J Respir Crit Care Med, May 2000, 161(5):1546–52.

DuBois, A; Botelho, S; Comroe, J; *A New Method for Measuring Airway Resistance in Man Using A Body Plethysmograph: Values In Normal Subjects and in Patients with Respiratory Disease*. J. Clin. Invest., 1956, 35, 327.

DuBois, A; Botelho, S; Bedell, G; Marshall, R; Comroe, J. *A Rapid Plethysmographic Method for Measuring Thoracic Gas Volume: A Comaprison with A Nitrogen Washout Method For Measuring Functional Residual Capacity In Normal Subjects*. J. Clin. Invest., 1956, 35, 327.

DuBois, A. *Significance of Measurement of Airway Resistance.*, Int. Symposium on Body Plethysmography, Nijmegen 1968, Progr. Resp. Res., vol 4, pp. 109–115 (Karger, Basel/New York 1969).

Mead, J; Whittenberger, J. *Evaluation of Airway Interruption Technique as a Method for Measuring Pulmonary Air–Flow Resistance*. J. Applied Physiol., 1954, 6, pp. 408–416.

Hemingway, A. *Measurement of Airway Resistance with the Body Plethysmograph*. 1973, Charles C. Thomas Publishing, Springfield, Illinois. pp. 5, 7–8, CH.III pp. 17–27, CH.V pp. 37–41.

Stocks, J; Marchal, F; Kraemer, R; Gutkowski, P; Yishhay, Ephriam; Godfrey, S. *Plethysmographic Assessment of Functional Residual Capacity and Airway Resistance*. Infant Resp. Function Testing., 1996, pp. 191–239.

Hoffman, A; Kuehn, H; Riedelberger, Klaus; Kupcinskas, R; Miskovic, M. *Flowmetric Comparison of Respiratory Inductance Plethysmography and Pneumotachography*. J. Appl Physiol 91:2767–2775, 2001.

Hoffman, H; Riedelberger, Klaus; Kupcinskas, R; Miskovic, M; Xuan–Mai Vo; Chase, S; Allen, T. *Airway Obstruction Assessed by Comparison of Inductance Plethysmographic (RIP) and Pneumotachraphic Flows*. Presentation Abstract, Comp Resp Soc, 1999, Vancouver.

Kuehn, H; Bolton, B; Bruns, S; Swanson, L; Hoffman, A; *Repeatability of a Large Animal Flowmetric System (LAFS) for Testing Airway Reactivity in the Field*. Presentation Abstract, Comp Resp Soc, 2000, Melbourne.

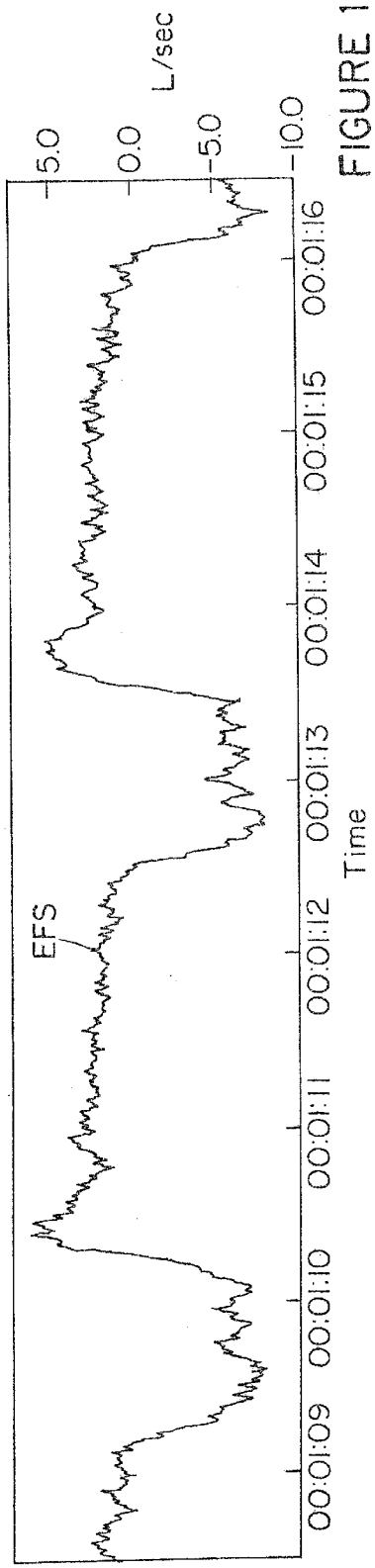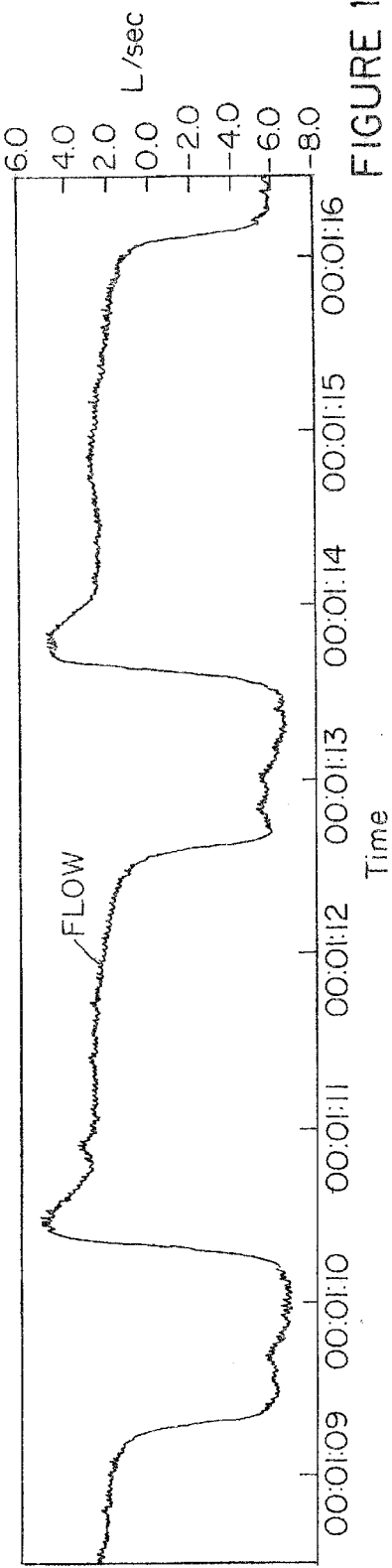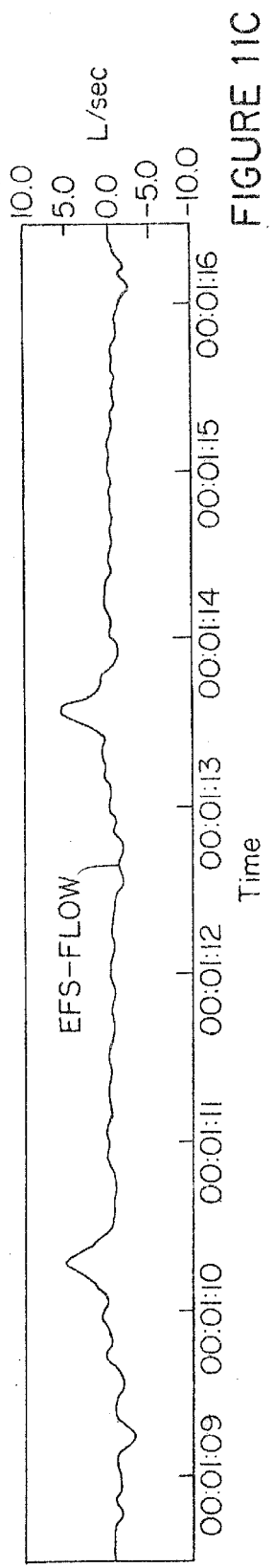

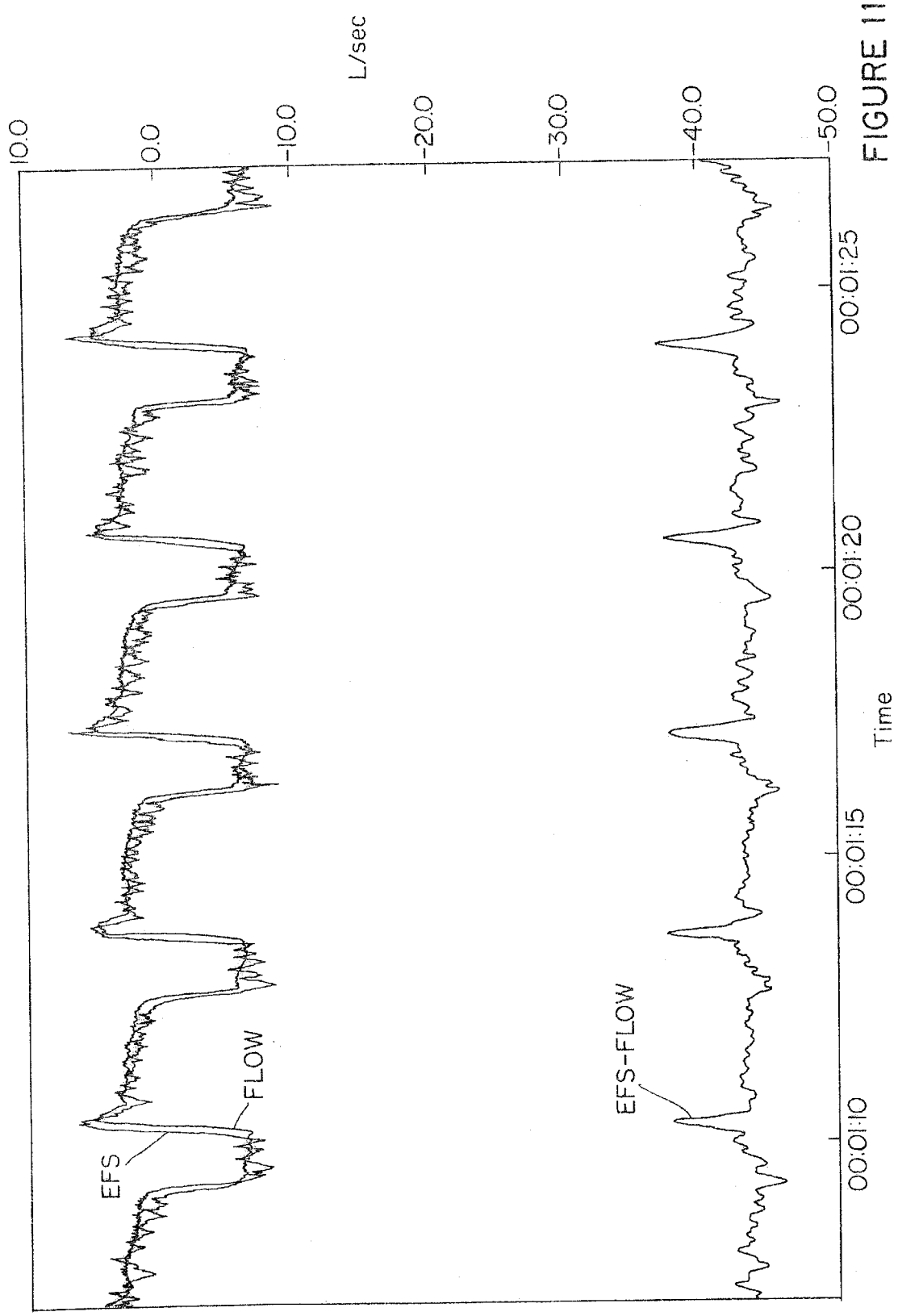

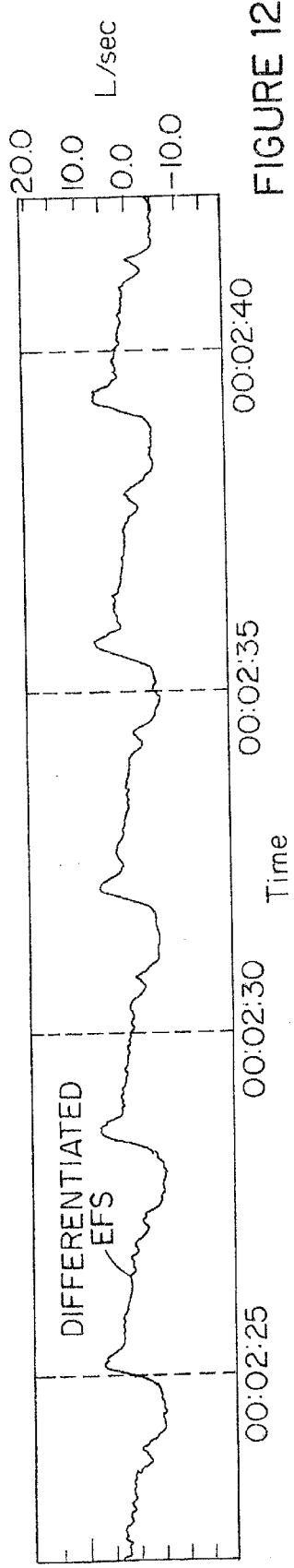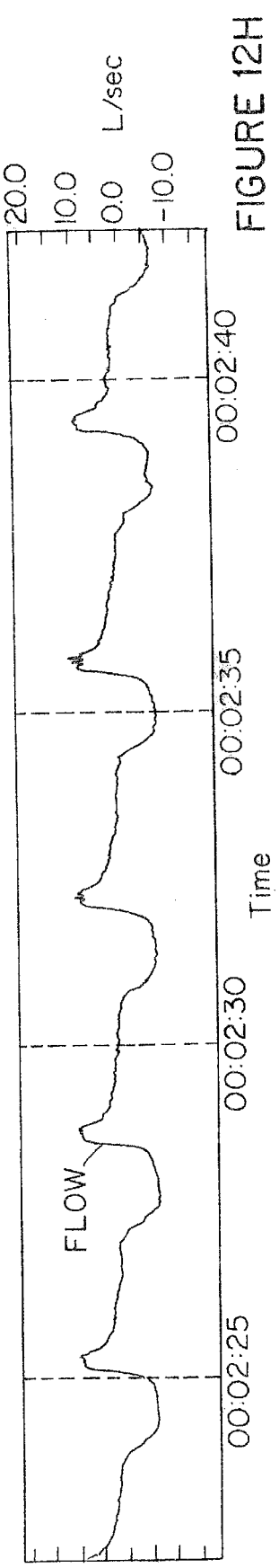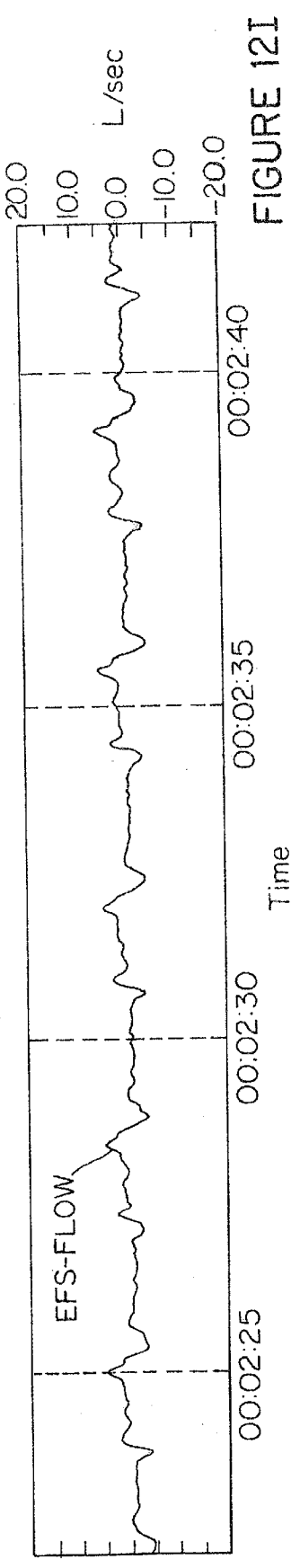

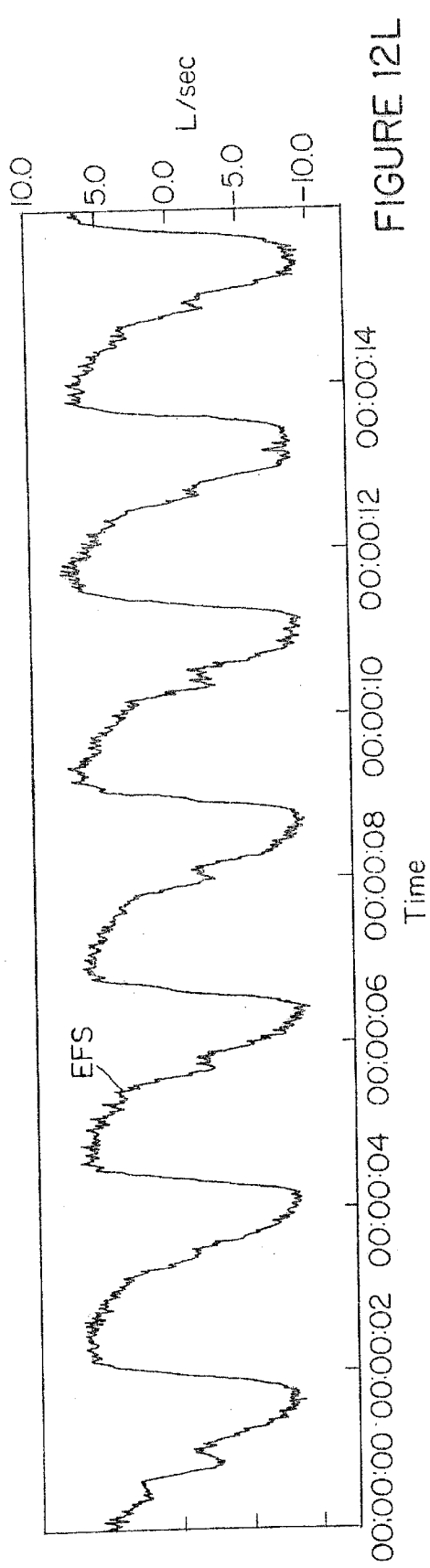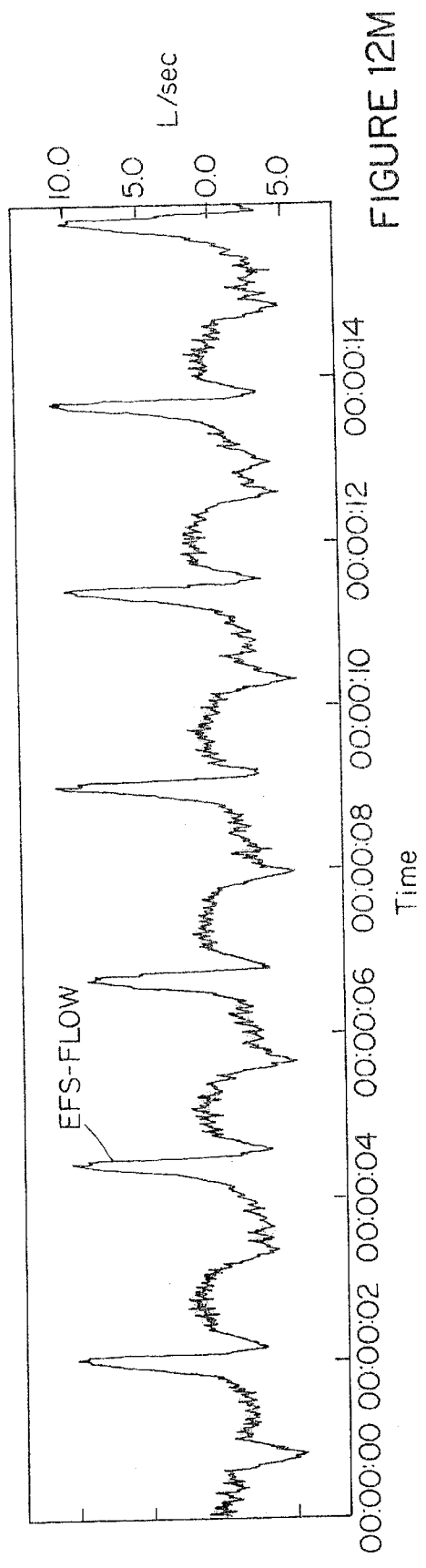

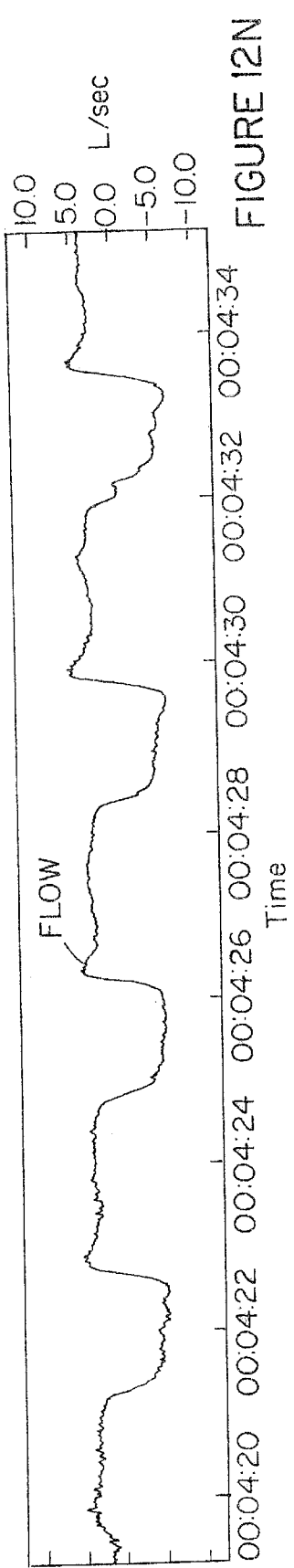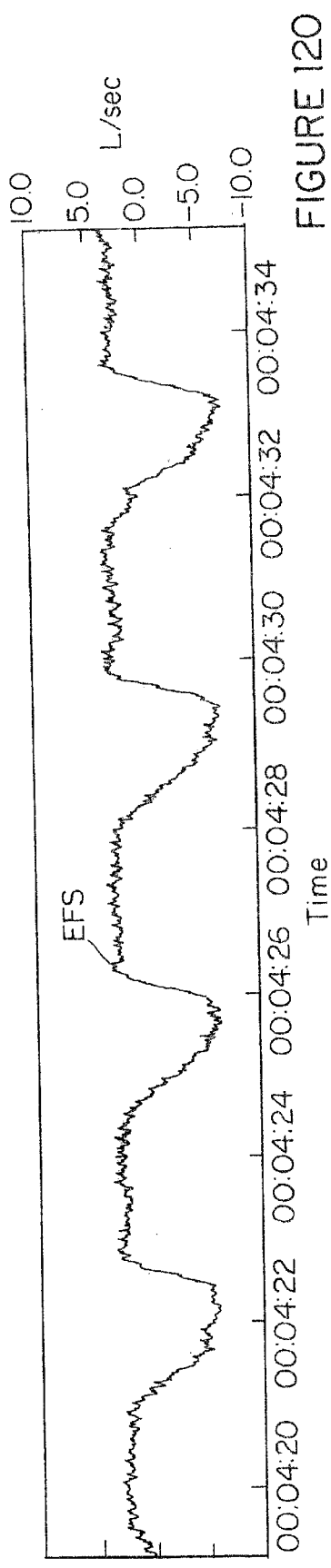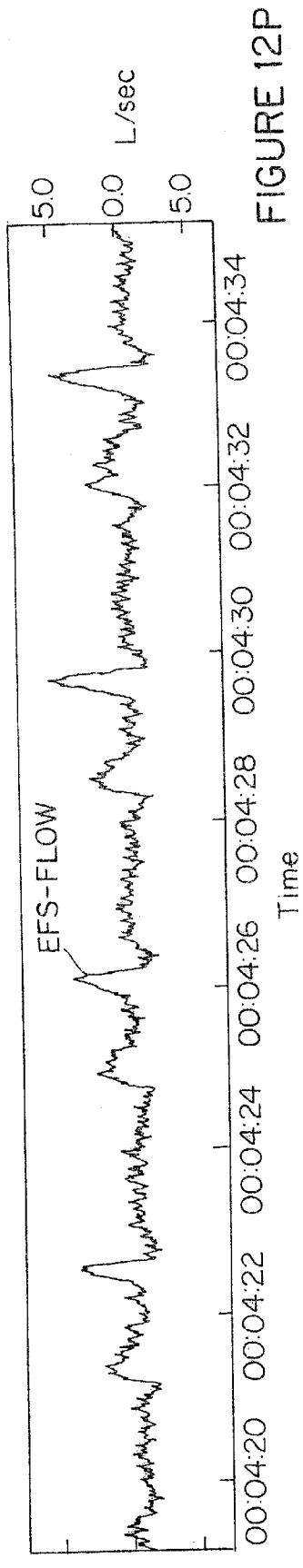

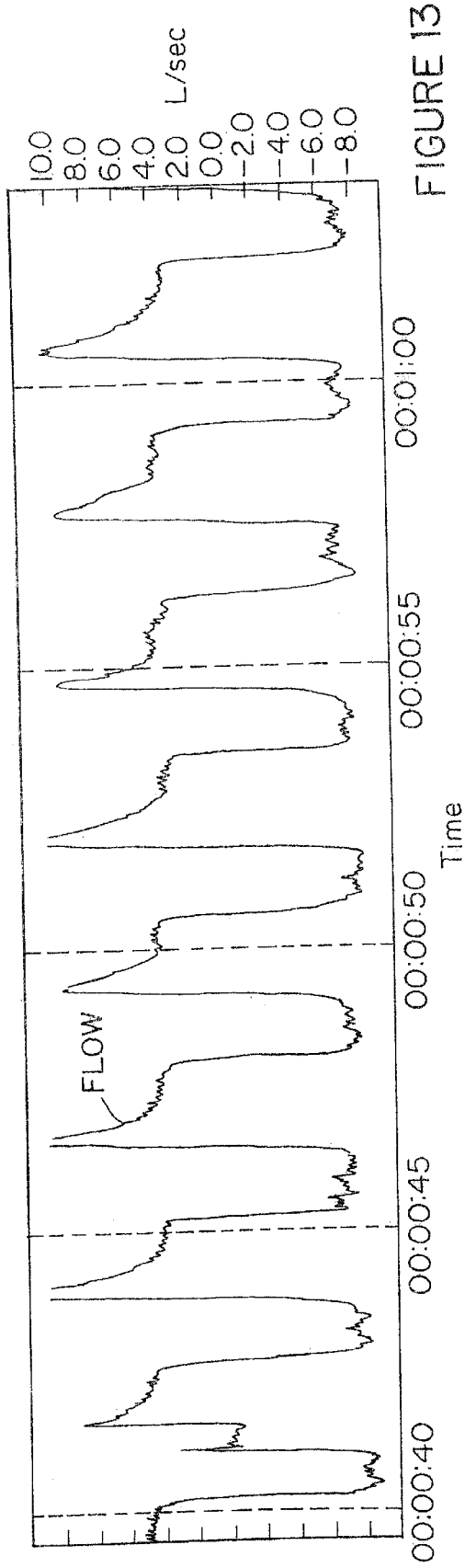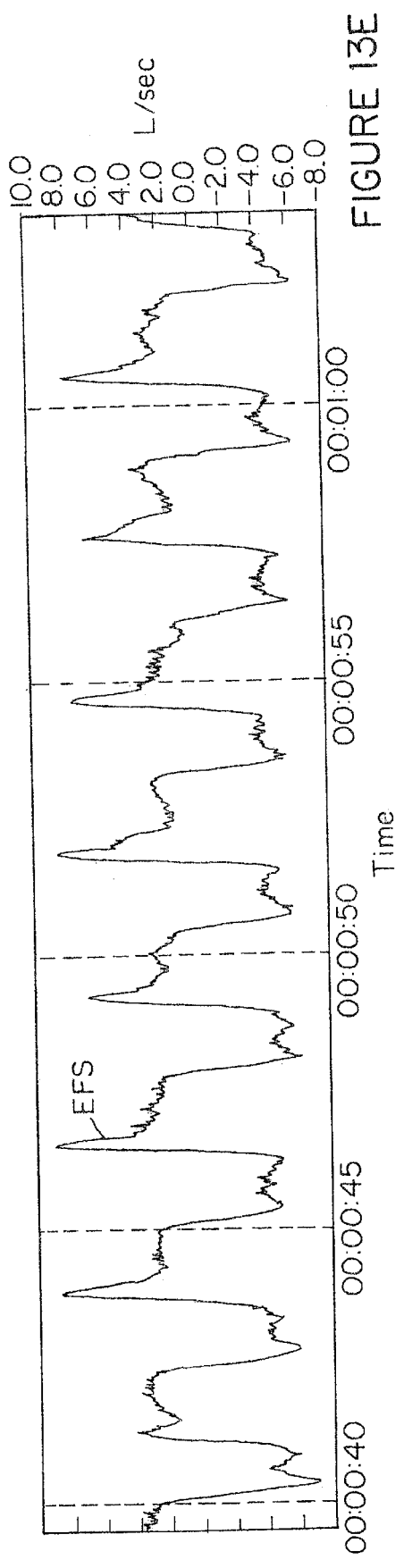

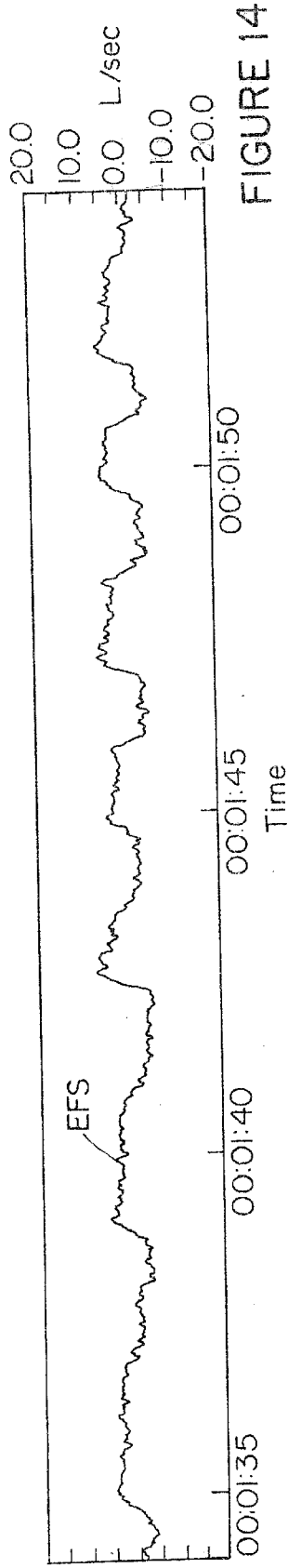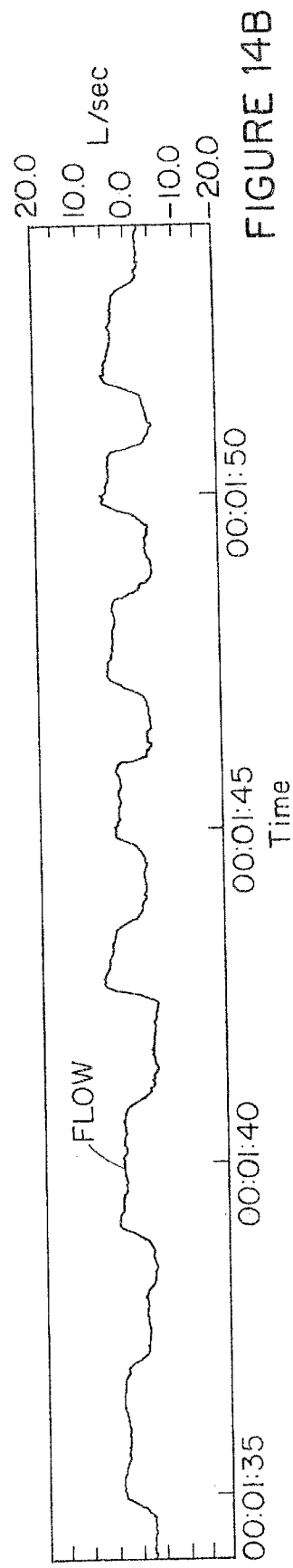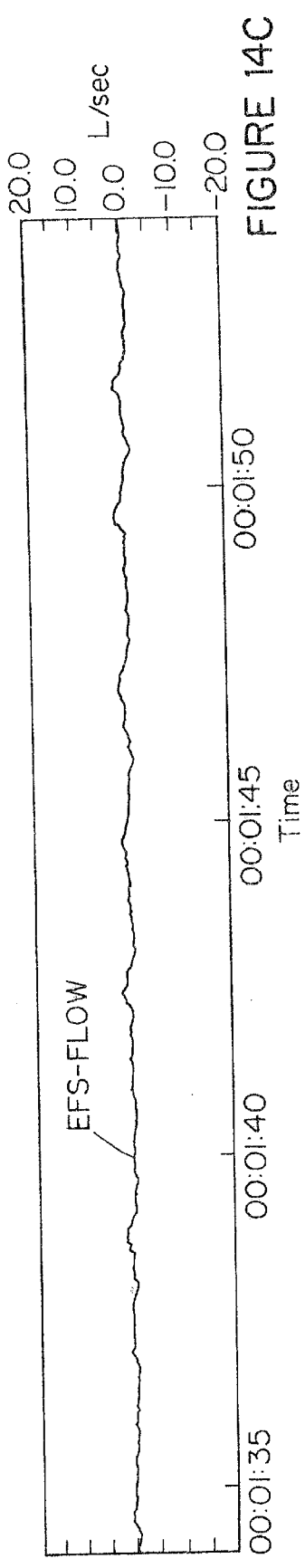

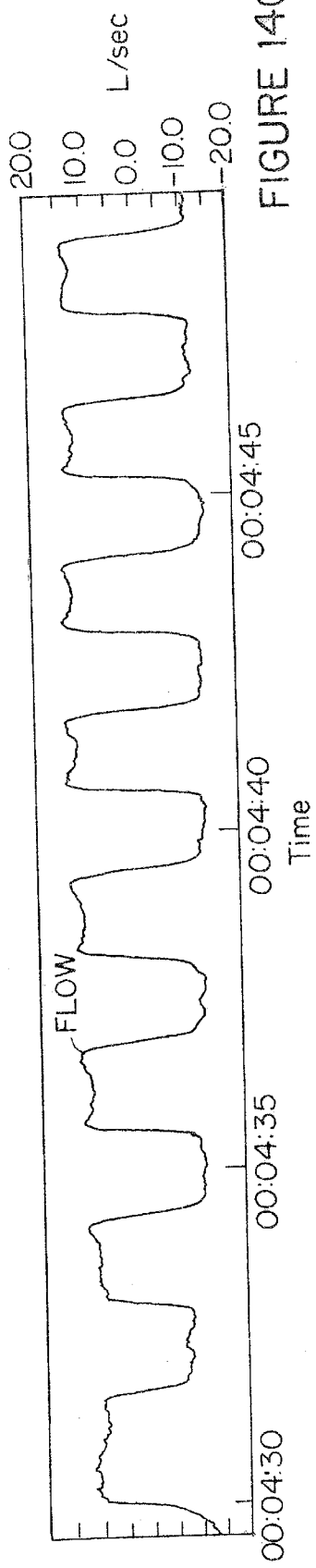
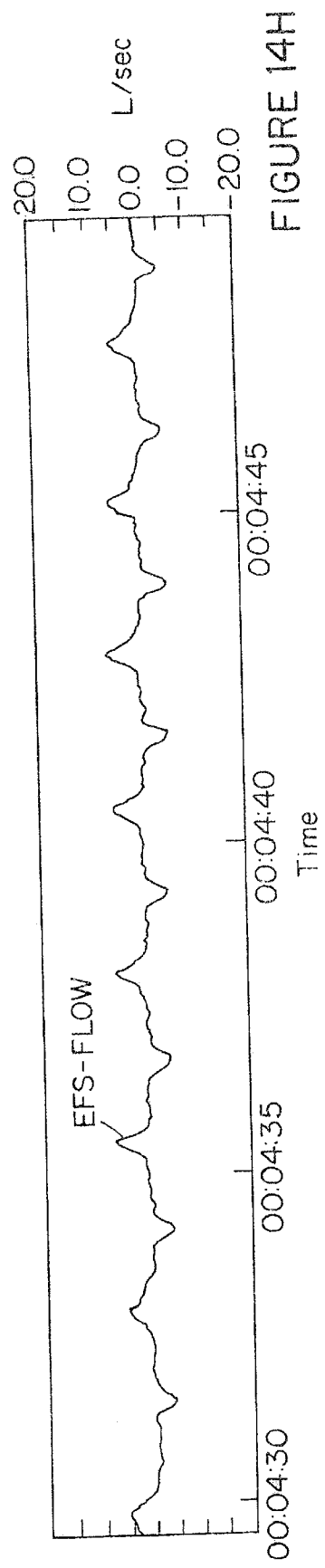
FIGURE 14G
FIGURE 14H

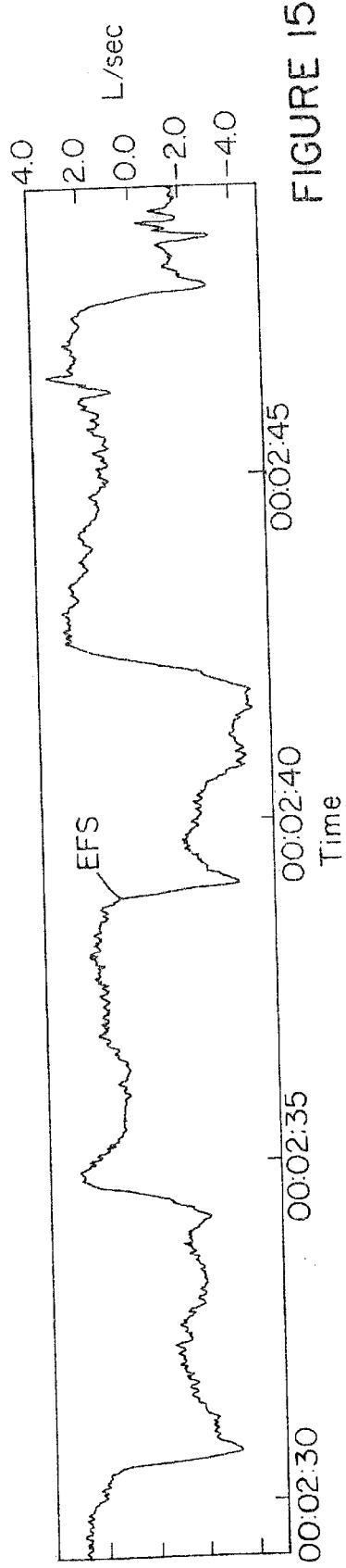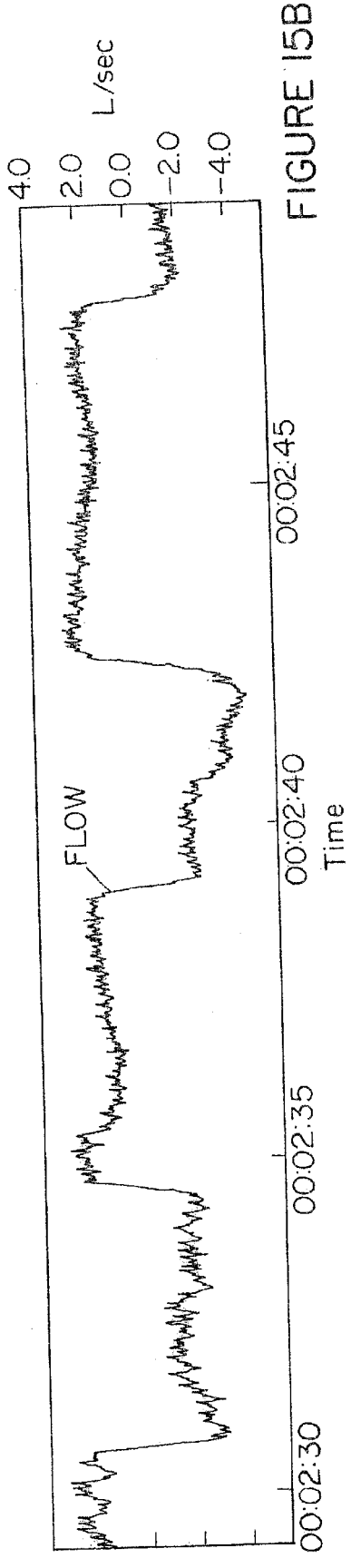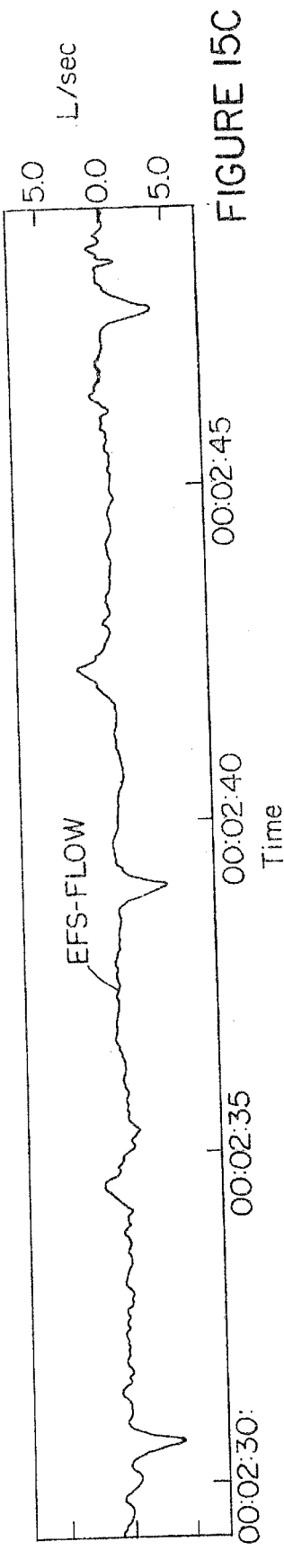

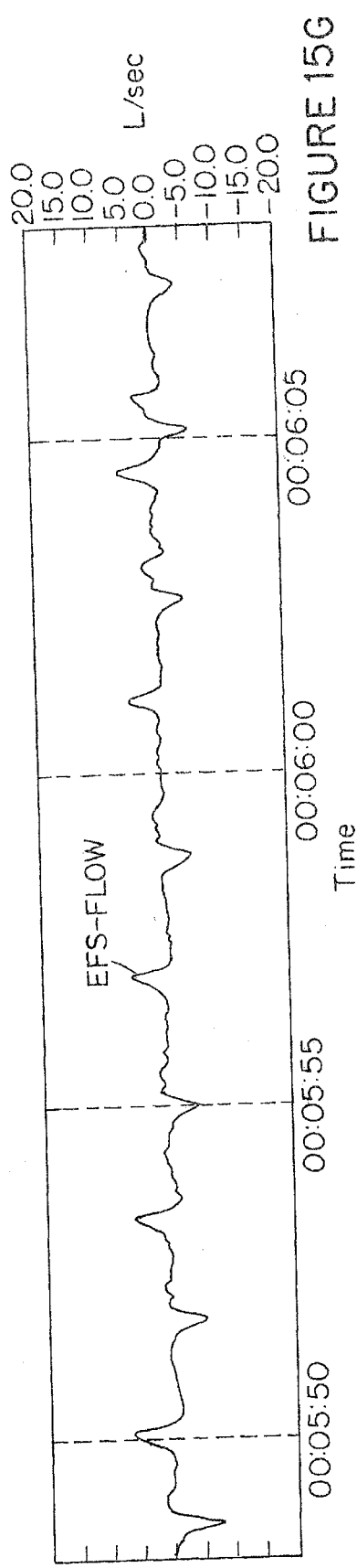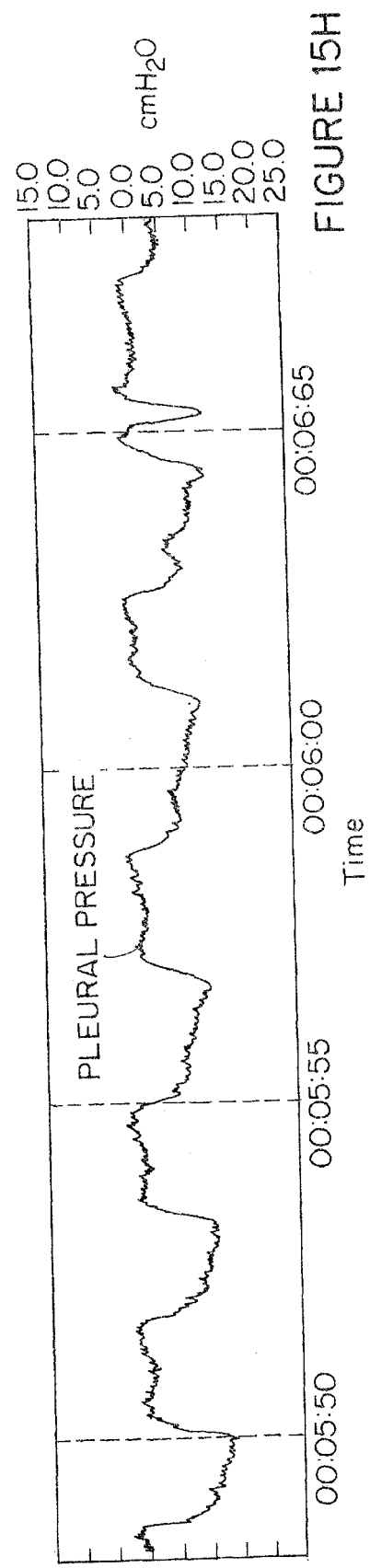

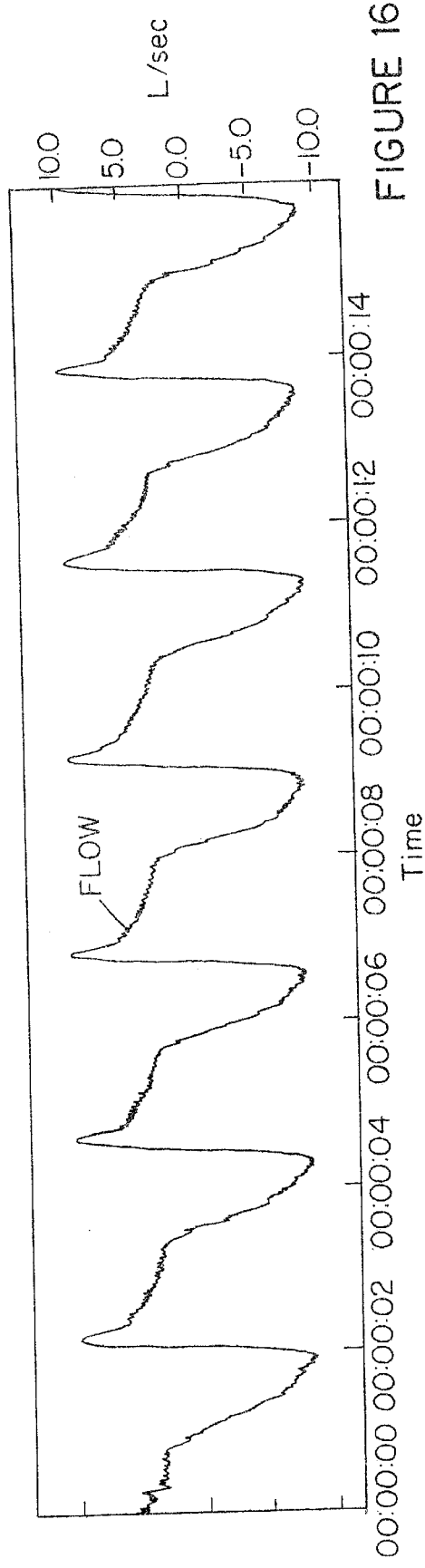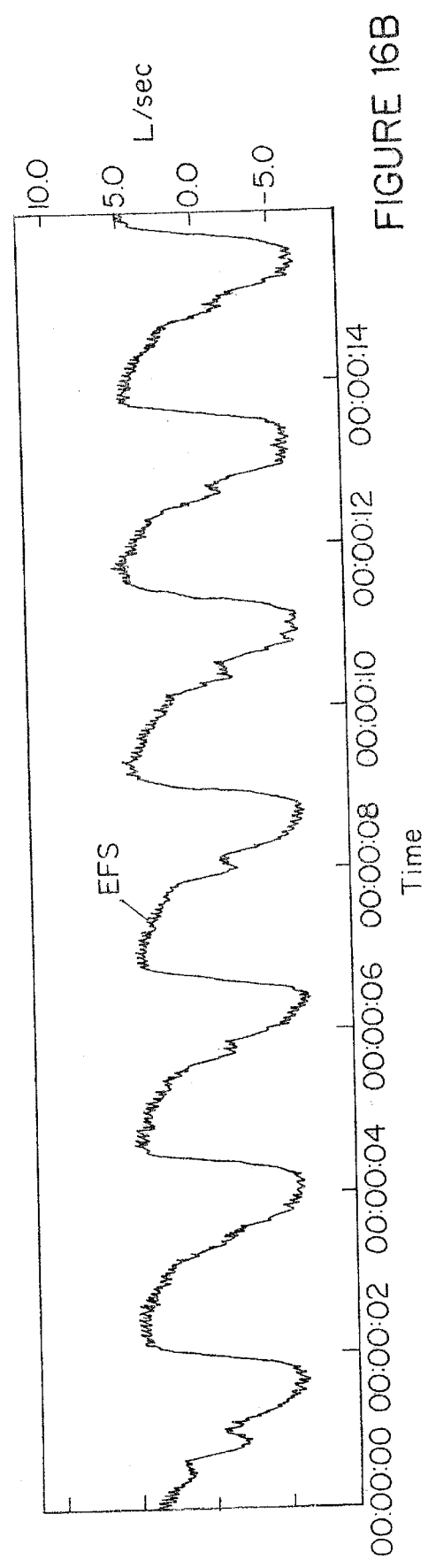

FIGURES 19A-G

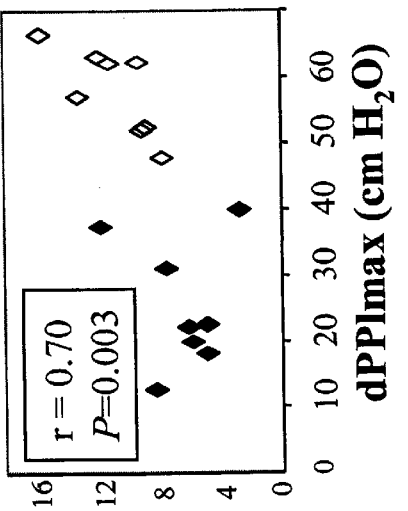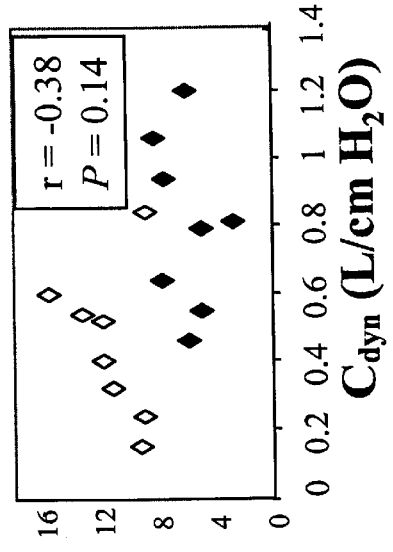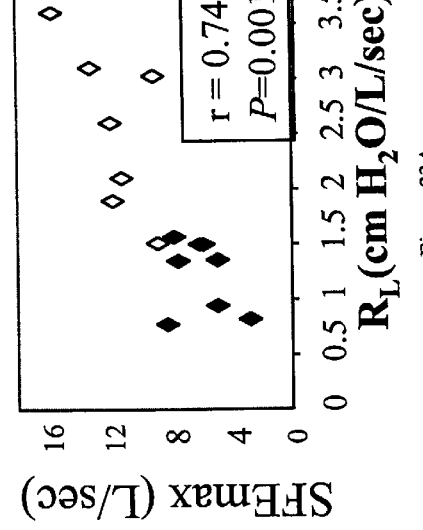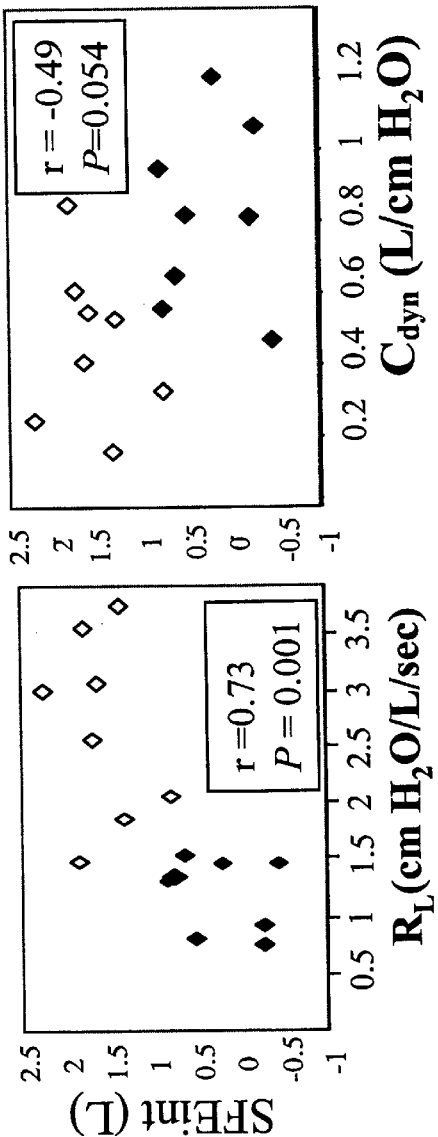
FIGURES 23A-23F

SYSTEM FOR MEASURING RESPIRATORY FUNCTION

CROSS REFERENCES TO RELATED APPLICATIONS

This application is a continuation-in-part-of U.S. patent application Ser. No. 09/298,352 now U.S. Pat. No. 6,287,264 filed on Apr. 23, 1999.

The entire contents of the above applications are incorporated herein by reference in entirety.

BACKGROUND OF THE INVENTION

Information regarding respiratory function of a living organism is important in the field of medicine. Respiratory function provides a measure of how efficiently air is moved through the respiratory system, and thus provides important clinical information for the diagnosis and treatment of many respiratory conditions and diseases. Some examples of these conditions are chronic obstructive pulmonary disease (COPD), asthma, and emphysema. In addition, respiratory function measurements allow medical practitioners to observe effects of a bronchodilator or long-term treatments for COPD, or conversely, the airway responses to a bronchoconstrictor challenge for assessment of airway reactivity.

Respiratory function testing includes mechanical function tests which typically compare the effort or driving pressure put forth by the organisms to some quantifiable outcome, such as the output of flow or minute ventilation. Lung function tests differ based on how these inputs and outputs are assessed. Examples of inputs to the respiratory system that are measured, include diaphragmatic electromyographic activity, changes in thoracic esophageal pressure or pleural pressure, changes in airway pressures in ventilated subjects, or noninvasive measures of drive including respiratory inductance plethysmography or impedance plethysmography, and whole body plethysmography. Examples of output measurements include flow, tidal volume, or ventilation measurements using devices that collect: flow at the airway opening. In general, the mechanical function of the respiratory system is best described by combining some measure of drive with output. Variables such as resistance and compliance can then be derived to assess the level of airway obstruction or loss of lung elasticity, respectively. This is the basis for classical physiologic modeling of the respiratory system: the comparison of transpulmonary pressure changes with flow or tidal volume, carefully assessed in the same time domain with avoidance of phase lag between signals.

Classical physiologic modeling measures total pulmonary resistance, dynamic compliance and related variables. However, the classical physiologic modeling relies on the invasive passage of an esophageal balloon for example, for measuring driving pressure, and flow as a measure of output. An esophageal balloon catheter is positioned in the midthoracic esophagus. Thus, classical physiologic measures are not used because of the invasive nature of the esophageal balloon catheter and the difficulty in calibrating the classical system under field conditions.

Lung function tests have evolved with respect to the sensors, recording devices, and analysis techniques used to evaluate input and output. However, a need still exists for the noninvasive determination of lung mechanical function and monitoring in human and animal subjects for clinical and research purposes. In this respect, a number of technologies to measure drive, mentioned above, are available. Devices such as single and double plethysmographs are used to measure drive. In the double chamber plethysmograph, thoracic and nasal flows are recorded as separate signals, whereas in barometric plethysmography, a single signal is recorded that is the net signal from the thoracic and nasal components. The latter is achieved simply on the basis that animals breathe inside a box where pressure changes are the net effects of both components. The aforementioned plethysmographic techniques, due to their size and complexity, preclude their use as a portable field test. In addition, these techniques enclose the subject, which is objectionable to both humans and animals.

Extending lung function tests to animals has been difficult because technological limitations prevent restraining a conscious animal for prolonged periods of time in devices or chambers such as, without limitations in plethysmograph chambers. As a result, most lung function studies to date have been limited to animals which are typically anesthetized or conscious animals that provide data with artifacts such as motion artifacts.

Significant challenges remain in conducting lung function tests in conscious animals. The respiratory system of conscious animals, such as canines, is evaluated by physical examination, x-rays, endoscopy, cytology, arterial blood gases, capnography and oximetry. Fluoroscopy can also be used for imaging the respiratory system in small animals, but only if they are sufficiently sedated. Simple measurements of spirometry using a facemask have been conducted in small animals that provide measurements of flow, tidal volume, minute ventilation, and respiratory frequency. These measurements are generally not useful beyond clinical impressions. None of these currently used methods address the mechanical function of the lungs. At best, the current methods determine tidal volume, airflow resistance, lung elasticity, and diffusion characteristics. Some of these characteristics can be inferred indirectly such as, for example, lung volume using an x-ray, and diffusion based on arterial blood gases or capnography, but are typically inaccurate measures.

A need still exists for improved systems and methods which provide for measuring respiratory function for health care practitioners, are portable and which are non-invasive to the living organisms. Further, there is still a need for pulmonary function testing devices for conscious animals.

SUMMARY OF THE INVENTION

The present invention relates to a system for measuring respiratory function of living organisms such as measuring airway obstruction, airway reactivity and changes in lung volume. In a preferred embodiment, the system for measuring respiratory function includes measuring gas compression or expansion which is the difference between the effort (defined herein as having active and passive work components and change in lung volume) required to breathe and airflow, by the combination of external sensors and direct measures of true flow. A preferred embodiment of the system of the present invention uses a direct comparison of an external flow signal (EFS) indicative of effort required to breathe which includes both an active work component and a passive work component indicative of the passive recoil of the lung, diaphragm and chest wall during exhalation, and the uncompressed flow, preferably in the same time domain, thereby permitting real time analysis using a plurality of measured variables to assess respiratory function. The apparatus and methods of the present invention provide noninvasive measures of airway obstruction or respiration restriction in the subjects.

The present invention is important for patients/subjects with known clinical obstructions. Response to treatments such as bronchodilators can be monitored and assessed to measure improvements using the present invention.

In addition, it is important to measure respiratory function in subjects who have a subclinical form of an airway obstruction, i.e., the subjects who do not normally display the clinical symptoms associated with airway obstructions. The present invention provides diagnosis of subclinical progressive or episodic conditions by testing the airway reactivity of the subjects. This is accomplished by provoking an obstruction of the airways by challenging the airways with a chemical such as a histamine, for example, and using the present invention to measure changes in the respiratory function of the subject.

According to one aspect of the present invention, the methods for measuring respiratory function of the present invention include the steps of obtaining a signal indicative of the effort required to breathe by the living organism, obtaining a signal indicative of uncompressed airflow through the respiratory system of the subject as measured at the airway opening, processing the signals indicative of effort and flow by comparing the signals dynamically in the same time domain to detect transient periods of gas compression or expansion that signify airway obstruction and to provide a signal indicative of the respiration restriction of the subject. Increase in respiratory system impedance is therefore detected by measuring gas compression or expansion indirectly, using non-invasive sensors.

A preferred embodiment of the present invention to measure airway reactivity features obtaining a signal indicative of the effort required to breathe and also referred to herein as the external flow sensor (EFS), obtaining a signal indicative of airflow through the respiration system of the subject and processing the two signals which includes the comparison of the two signals to provide a signal indicative of the measure of respiration restriction of the subject. This method uses bronchoconstrictors to challenge the respiratory system of the subjects so as to provoke a response and test the airway reactivity of the subjects.

The preferred embodiment to measure airway reactivity may employ different sensors such as respiration induction plethysmography or impedance plethysmography or devices such as piezoelectric sensors to obtain the signal indicative of effort required to breathe. Fiber optic respiratory plethysmography methods may also be used similar to respiratory inductance plethysmography. The bands in the fiber optic embodiment are composed of fiber optic material. The signal indicative of effort or change in lung volume can also be obtained by using optoelectronic plethysmography that measures the movement of a plurality of retro-reflective markers using television cameras connected to a motion analyzer. The signal indicative of uncompressed airflow through the respiratory system can be obtained through the use of a pneumotachographic measurement device, an ultrasonic device, a thermistor or a breath-sound intensity device. Additionally, the signal indicative of the effort required to breathe is calibrated by assigning a voltage span to the specific volume or flow span. Calibration for the signal indicative of uncompressed airflow is optional, but preferred in conjunction with the use of methods such as flow meters or precision volume syringes.

The signals indicative of the effort and airflow are amplified and digitized. The signals are then compared and subtracted to give an indication of the respiration function of the subject. A programmable computer can be programmed to perform an analysis of the measured signals and a display formatted to show the recorded and processed data. An electronic memory can be used to store the measured and/or processed data. The comparison of the effort or external flow signal with uncompressed airflow is performed either by overlapping the waveforms and performing visual comparisons between the two waveforms or by synthesizing a composite waveform by performing a digital subtraction point-by-point of the airflow from the external flow or effort signal. Further, Fourier analysis may be used to compare the signal indicative of effort with uncompressed airflow. For a subject with a healthy respiration system, the effort and flow signals are in phase. However, during a condition such as one that occurs with bronchoconstriction, the airflow signal of the subject is no longer in phase with the signal indicative of effort or thoracic movement. During the condition when the airways are obstructed the effort signal or thoracic movement will lead nasal flow. This phase shift occurs in the time domain. The magnitude of the phase shift can be used as a measure of airway resistance or obstruction.

Another preferred embodiment of the present invention to measure clinical obstructions and response to treatments, such as the administration of bronchodilation medication, features obtaining a signal indicative of the effort required to breathe and a signal indicative of airflow through the respiration system and processing the two signals to obtain a signal indicative any respiration restriction of the subject. In another embodiment, the present invention can be used as a monitoring system for respiration functions. The advantage of the present invention in terms of its lack of obtrusiveness allows the subject to adopt normal body posture and yet be monitored. The monitoring application of the present invention is well suited for continuous or intermittent home or hospital monitoring of adults, children, infants and animal subjects. In particular, for patients on continuous positive airway pressure (CPAP) or assisted ventilation, the system of the present invention can be coupled to a CPAP delivery device or ventilator. The present invention triggers the use of the ventilators upon detecting respiratory restriction. Similarly, an oxygen delivery system can be coupled to the respiration function measurement system of the present invention.

According to another aspect of the present invention, an apparatus for obtaining a signal indicative of respiration of a living organism includes a first device that obtains a first input signal indicative of effort required to breathe by the organism, a second device that obtains a second input signal indicative of actual airflow through the respiratory system of the organism and a processing device that processes the first and second inputs to form a third signal indicative of respiration restriction of the organism. The processing device may be a programmable computer, programmed to perform an analysis of the measured input signals and a display formatted to show the recorded and processed data. The processing device can process the input signals using analog circuitry or digital circuitry. An electronic memory can be used to store the measured and/or processed data. The programmable computer can be a laptop computer, facilitating the portability of the apparatus. Thus, the system for measuring respiration function is lightweight and compact, having a weight of less than fifteen (15) pounds, preferably less than ten (10) pounds. This provides a portable system that can be readily transported by the user.

According to another aspect of the present invention, an apparatus and method of a preferred embodiment measures lung function and structure during tidal breathing or during occlusions for conscious animals. The method for measuring airway and lung tissue functionality includes calibrating a chamber that is a constant volume plethysmograph in which the subject's head is positioned outside the chamber but the subject breathes into the chamber. The calibration may include adjusting the gain settings of amplifiers, and calibrating the chamber pressure relative to a known volume of gas. The method to measure lung functionality further includes acclimatizing a subject in the chamber, measuring the functional residual capacity (FRC) of the subject and the airway pressure as it relates to chamber pressure. A movable cover or shutter assembly is preferably closed prior to the FRC measurement. Upon opening the shutter assembly airway resistance is measured. The method may further include the measurement of dynamic flow metric indices which provide the ability to study differences between inspiratory and expiratory breaths.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention. The principles and features of this invention may be employed in varied and numerous embodiments without departing from the scope of the invention.

BRIEF DESCRIPTION OF THE DRAWINGS

FIGS. 11A–11E graphically illustrate the effort, flow and comparative signals as measured and processed from an equine subject after administration of a bronchodilator;

FIGS. 12F–12J graphically illustrate the effort flow and comparative signals measured and processed from the equine, subject used in FIGS. 12A–12E after administration of a bronchodilator;

FIGS. 12K–12M graphically illustrate calibrated and normalized flow, effort and comparative signals measured and processed from an equine subject having chronic obstructive pulmonary disease;

FIGS. 12N–12P graphically illustrate calibrated and normalized flow, effort and comparative signals measured and processed from the equine subject used in FIGS. 12K–12M after administration of a bronchodilator;

FIGS. 13D–13F graphically illustrate the effects on the effort signal as measured only from the abdomen of the equine subject used in FIGS. 13A–13C, the flow signal and comparative signal after the administration of a bronchoconstrictor;

FIGS. 14A–14E graphically illustrate the effort, flow, comparative and pleural pressure signal of an equine subject without any airway obstructions;

FIGS. 14F–14J graphically illustrate the effort, flow, comparative and pleural pressure signals of the equine subject used in FIGS. 14A–14E during hyperventilation, in the form of hyperpnea;

FIGS. 15A–15D graphically illustrate the effort, flow, comparative and pleural pressure signals of an equine subject without any airway obstructions;

FIGS. 15E–15H graphically illustrate the effort, flow, comparative and pleural pressure signals of the equine subject used in FIGS. 15A–15D during hyperventilation, in the form of tachypnea;

FIGS. 16A–16C graphically illustrate the uncalibrated flow, effort and comparative signals from an equine subject having chronic obstructive pulmonary disease;

FIGS. 23A–23F graphically illustrate the correlation between conventional and present invention test variables in eight horses with naturally occurring recurrent airway obstruction, before and after administration of a bronchodilator;

DETAILED DESCRIPTION OF THE INVENTION

The present invention is directed to systems and methods for measuring respiratory function of subjects by measuring gas compression or expansion and airflow resistance by a combination of external flow sensors and direct measures of airflow. The external flow sensors measure effort required to breathe, which includes an active work component and a passive work component indicative of the passive recoil of the lung, diaphragm and chest wall during exhalation and are hereinafter referred to as effort or EFS signals or waveforms.

Figure 1:
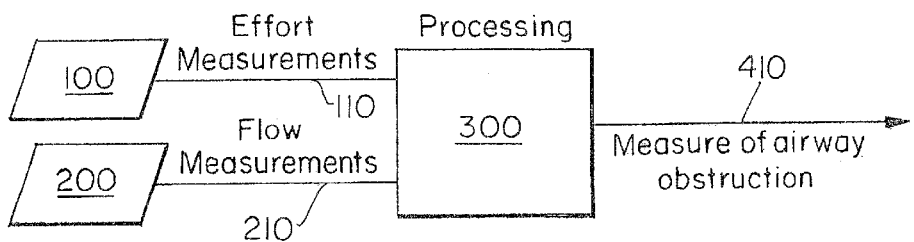
FIG. 1 is a top-level flow chart describing the method for measuring respiratory function in accordance with the present invention.

Referring to the drawings, FIG. 1 is a flow chart that describes the system for measuring respiration function in accordance with the present invention. Essentially signals 110 indicative of the effort required to breathe by a subject are obtained using an external flow sensor, along with signals 210 indicative of the uncompressed airflow in the respiratory system of the subject. The two signals are processed in processor 300 and a third signal 410 indicative of the difference between the effort and airflow signals is obtained which is a measure of airway obstruction, in the subject using the system of the present invention.

Figure 2:
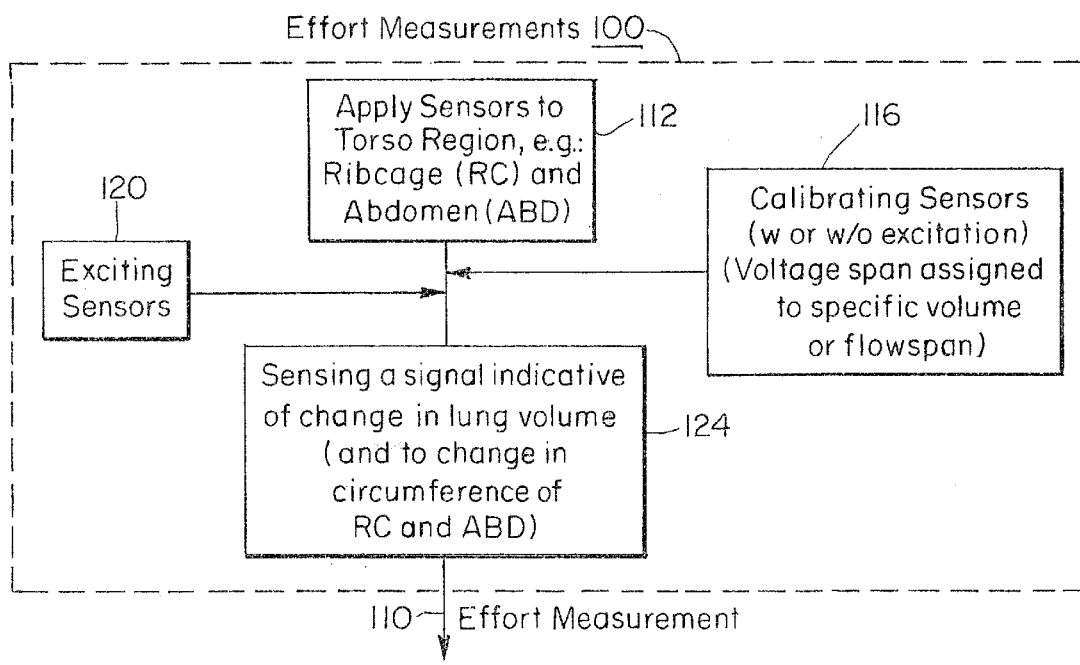
FIG. 2 is a flow chart describing the effort measurement methodology in accordance with the present invention.

Referring now to FIG. 2, the signals 110 indicative of the effort measurements are obtained by the step of applying external flow sensors 112 to the torso of a subject, for example to the rib cage and the abdominal regions of the subject. The sensors are calibrated per step 116 by exciting or alternatively not exciting the sensors. Essentially the voltage span is assigned to specific volume or flow spans. Once the signals are excited per step 120 after calibration 116, a signal indicative of the change in lung volume which is essentially a change in the circumference of the rib cage and the abdomen is collected per step 124 and obtained for further processing.

Figure 3:
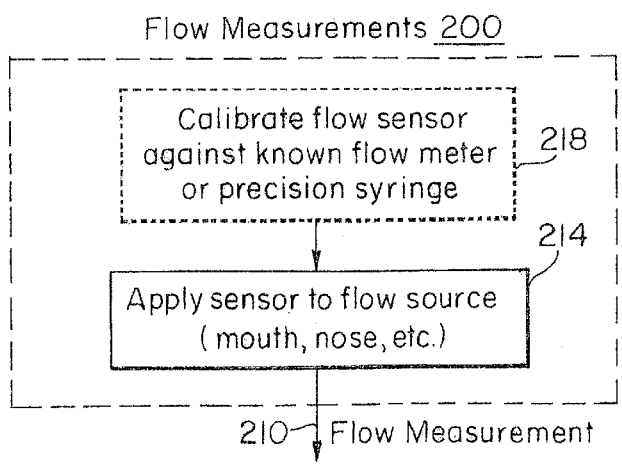
FIG. 3 is a flow chart describing the airflow measurement methodology in accordance with the present invention.

Referring now to FIG. 3, airflow measurements are obtained, which are indicative of the uncompressed airflow through the respiratory system of the subject by the step of applying 214 sensors to the flow source, be it the mouth and/or the nose, etc. The calibration per step 218 of the flow sensor is not required for all measurements and is optional. However, if a calibration is performed it is done so by calibrating the flow sensor against a known flow meter or precision syringe. An uncalibrated flow sensor such as a sound microphone can be applied to gauge the airflow through the respiratory system.

Figure 4:
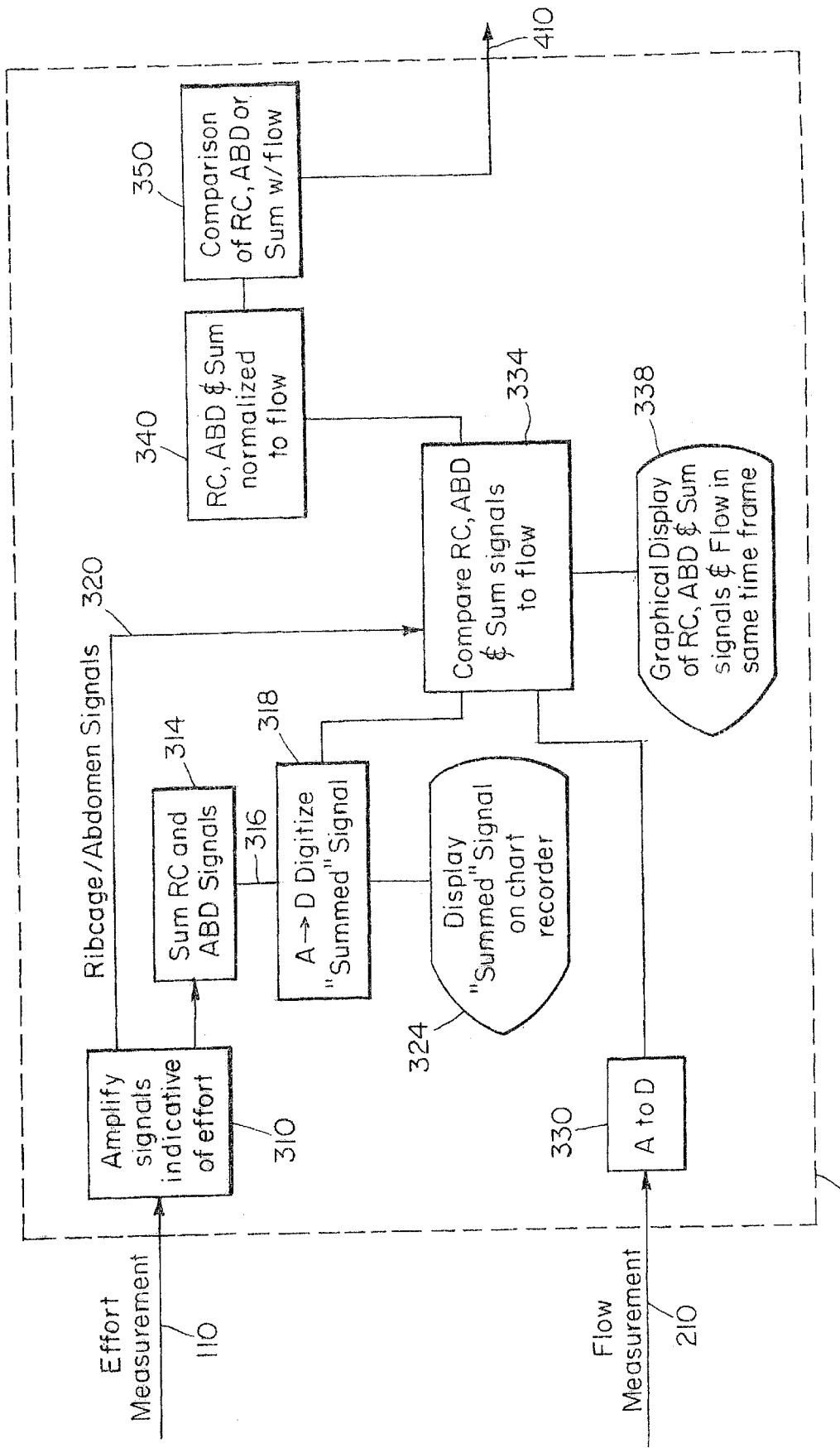
FIG. 4 is a flow chart describing the processing methodology in accordance with present invention.

Referring to FIG. 4, the effort measurements 110 and flow measurements 210 are then processed by the processor 300 of the present invention using a particular sequence of steps. The effort measurements are amplified per step 310. The rib cage and abdomen signals are summed per step 314 and the summed signal 316 is digitized per step 318. Alternatively, the analog signals can be used. The summed signal as well as the individual rib cage and abdominal signals 320 can be displayed on a chart recorder per step 324. The flow measurements 210 are also converted to digital signals per step 330. Both the effort measurements and airflow measurements, either as analog or digital signals, are then compared against each other per step 334 and the comparison can be graphically displayed in the same time domain per step 338. The rib cage, abdominal and summed signals are normalized to the airflow per step 340 prior to comparison of the signals. Normalizing preconditions the signals in order to provide a magnitude comparison. The inspiratory area of the airflow waveforms are used for normalization as the inspiratory area is typically not affected by lower airway obstructions. The comparison of the summed signal with airflow and the individual rib cage and abdominal signals with airflow is performed per step 350. Essentially, the airflow signals are subtracted from the effort signals using various algorithms. Effort and flow signals are compared dynamically, using digital point by point comparisons throughout each breath. As the frequency response of each sensor is matched, transient compression or expansion of gas due to obstruction is evident by instantaneous differences between effort and flow amplitude and phase. The resultant signal 410 of the comparison provides a measure of the respiratory function of the subject.

Figure 5:
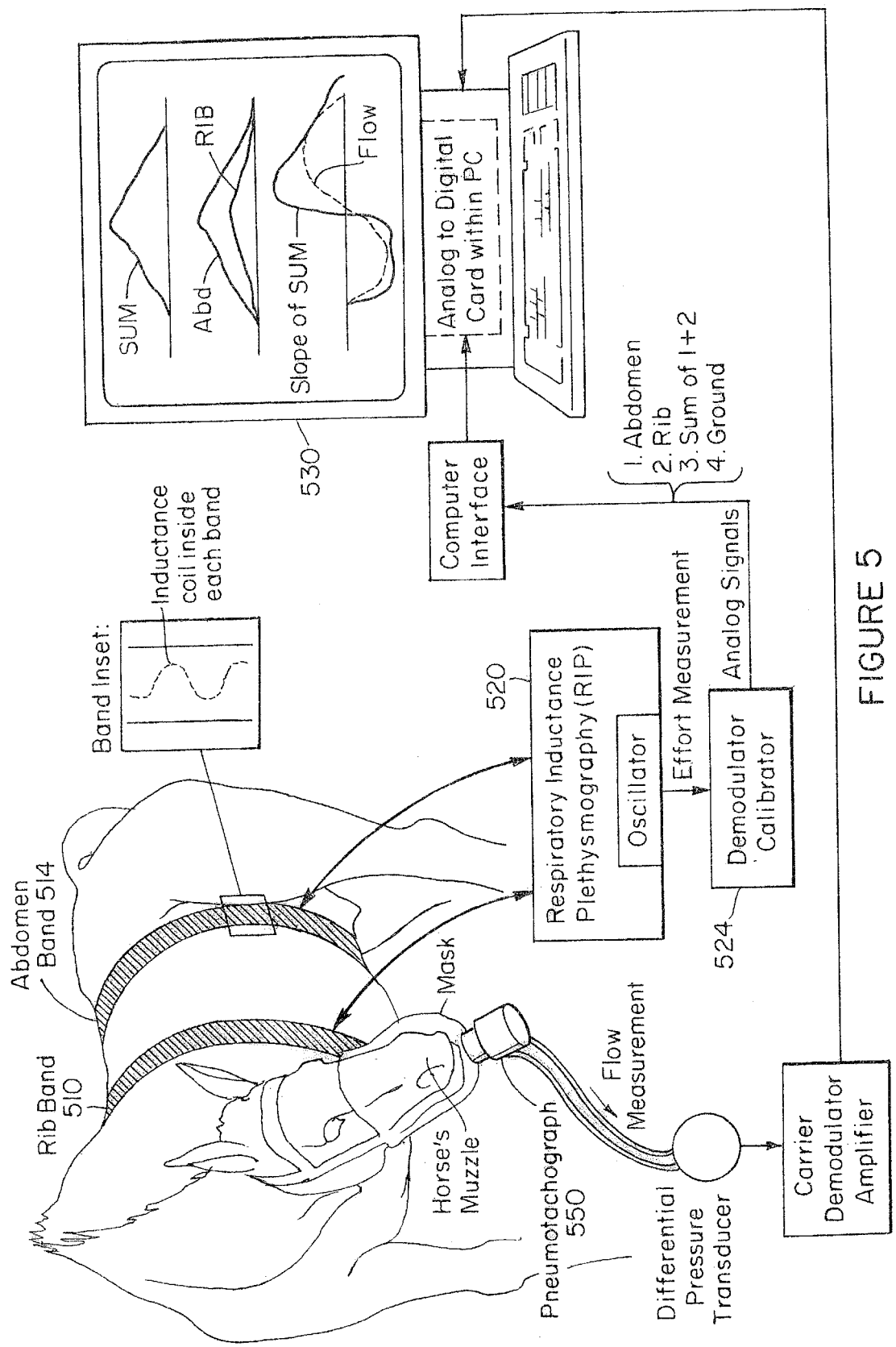
FIG. 5 is a schematic diagram of the system used for measuring respiratory function in horses in accordance with the present invention.

Referring to FIG. 5, the system to measure respiratory function uses respiratory inductance plethysmography (RIP) which includes two self sticking elastic cloth bands placed around the rib cage 510 and abdomen 514 to measure the effort or external flow. The bands can be folded unto themselves to create a snug fit. The bands contain a sinusoidal coil of wire sandwiched between two pieces of cloth band. The wire stretches with deflections of the subject's cross-sectional area of chest wall and abdomen with respiration. An external oscillator circuit 520 excites the wires with an oscillating voltage. Respiratory movements change the inductance of the coiled wires proportionally to the changes in volume, of the rib cage and abdomen. The change in inductance alters the net voltage across the coil. The voltage is demodulated and converted into an analog signal per step 524 that can be amplified and recorded by computer software on a real time basis, and replayed for post-acquisition analysis. Alternatively, the use of a piezoelectric sensor and amplifier to measure effort directly provides a flow signal, thus, not requiring differentiation of a volume signal which typically adds noise and may potentially change the characteristics of the effort signals, i.e., either the magnitude or phase components.

Voltage recordings of RIP are converted by software in a processor 530 into differentiated waveform of the volume deflections of the sum of the rib and abdomen bands if necessary. The difference in magnitude between the differentiated sum and flow waveform peaks or areas of particular segments of the breath are calculated. RIP has been used in human medicine to measure tidal volume and respiratory frequency and to detect apnea in adults, infants, and children. The system can also be used to monitor breathing patterns. RIP is based on the similar concepts of barometric plethysmography and is therefore confounded by similar factors. In barometric plethysmography, for instance, thoracic movement overestimates flow in patients with airway obstruction because of gas compression. The degree that thoracic movement overestimates flow can be used as a quantitative measure of obstruction. More recently, non-invasive whole body plethysmography or single chamber barometric plethysmography has been used in this regard. This technique is based on the fact that an animal in a closed chamber creates pressure fluctuations within the chamber with respiration. With inspiration, air is moved from the chamber into the animal, and the pressure within the chamber decreases. The air is warmed and humidified within the animal and thus the air expands as does chest volume. This thoracic flow increases the pressure measured in the chamber to a greater extent than the drop in pressure caused by nasal flow. The pressure in the chamber, or box pressure, reflects the net differences of these two processes. Tidal volume can be determined from these pressure changes in normal subjects.

During bronchoconstriction or other obstructive disorders, air is compressed in the animal. Nasal airflow of the animal is no longer in phase with thoracic movement. Thoracic movement leads nasal flow. This phase shift affects the box pressure signal in the time domain. The magnitude of the phase shift can be used as a measure of airway resistance. The degree of bronchoconstriction can be quantified by analyzing the shape of the waveform.

The same concept of gas compression with bronchoconstriction and phase delay can be detected by the RIP system when compared with flow. This technique of non-invasive monitoring of respiration is based on the separate contributions of rib cage and abdomen to tidal volume. The respiratory system can be approximated by two degrees of motion, displacements of the rib and abdomen compartments then compared to flow on the same time scale.

The lung function testing methodology of the present invention combines a pneumotachograph 550 or other flow sensors for flow measurement with RIP bands or other external sensors. Just as there is a measurable change in the magnitude and phase of nasal versus thoracoabdominal signals in a box plethysmograph, similar changes are detected by measuring RIP and flow separately. This methodology enables medical practitioners to evaluate the response of humans or animals such as horses with chronic obstructive pulmonary disease (COPD) to bronchodilators, and to monitor the progression of the disorder.

Calibration of Respitrace® bands or other sensors which are used as the RIP bands or sensors in human medicine can be performed using the iso-volume method which relies on training the patient to shift a held breath between the abdominal and rib compartments of the respiratory system. Another method, the least mean squares regression technique relies on varying body position or by taking measurements in different sleep stages and solving simultaneous equation. Both these methods are not appropriate for equines.

A possible method of calibration in horse is the qualitative diagnostic calibration method. This method does not require active subject cooperation as it is carried out during a five minute period of natural breathing in one posture. A proportionality constant of the relative contribution of rib and abdomen can be determined and applied to the system.

The types of flow sensors that may be used for practicing the present invention includes pneumotachographs. Two types of pneumotachographs that may be used are a Fleisch type and a screen-resistor type such as one supplied by Hans Rudolph, Inc. The pneumotachograph such as the one supplied by Hans Rudolph uses a unique housing configuration and screen assembly design to convert the flow of gas into a proportional linear signal of differential pressure from the two pressure taps for input into a differential gas pressure transducer. Another kind of flow sensor which may be used is an ultrasonic flow sensor which also provides a linear signal. In addition, thermistors such as a hot-wire anemometer may be used to measure flow. Further, a breath sound intensity flow sensor may also be used to gauge flow.

Effort sensors may comprise respiratory inductance plethysmography, such as sensors supplied by Sensor Medics, Inc., or Ambulatory Monitoring, Inc. The functions of oscillation and demodulation for RIP bands may be provided by a personal computer interface box. In addition, piezoelectric sensors which are excited with stretching or bending may also be used to provide a signal indicative of effort with the advantage of providing a flow signal directly. No differentiation of the measured signal is required as the measured signal is the flow signal unlike the RIP bands which measures a volume change. Impedance plethysmography may also be used to provide a signal indicative of the effort.

Figure 6A:
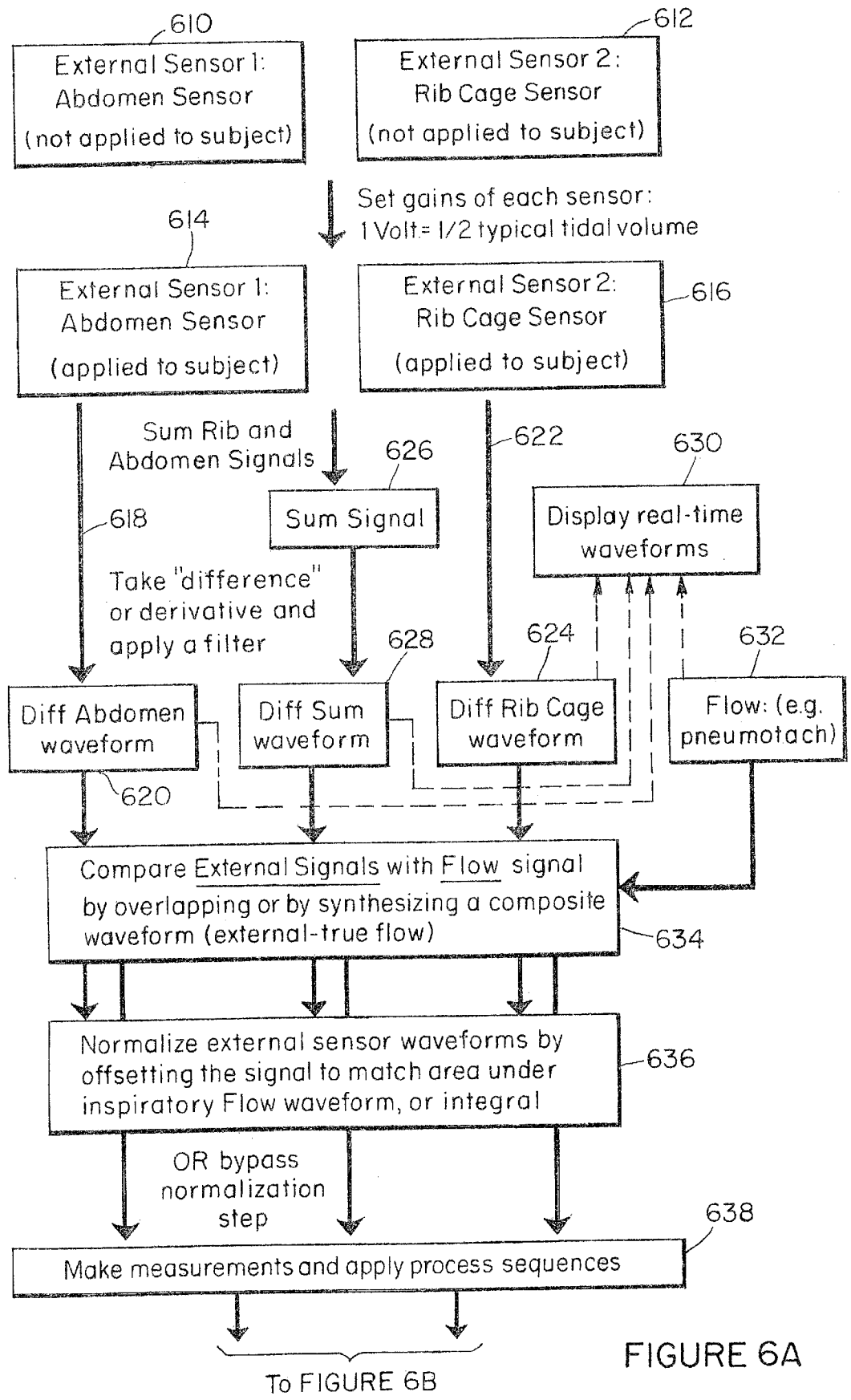
FIGS. 6A and 6B are flow charts describing the details regarding the processing of the signals measured in accordance with the present invention.
Figure 6B:
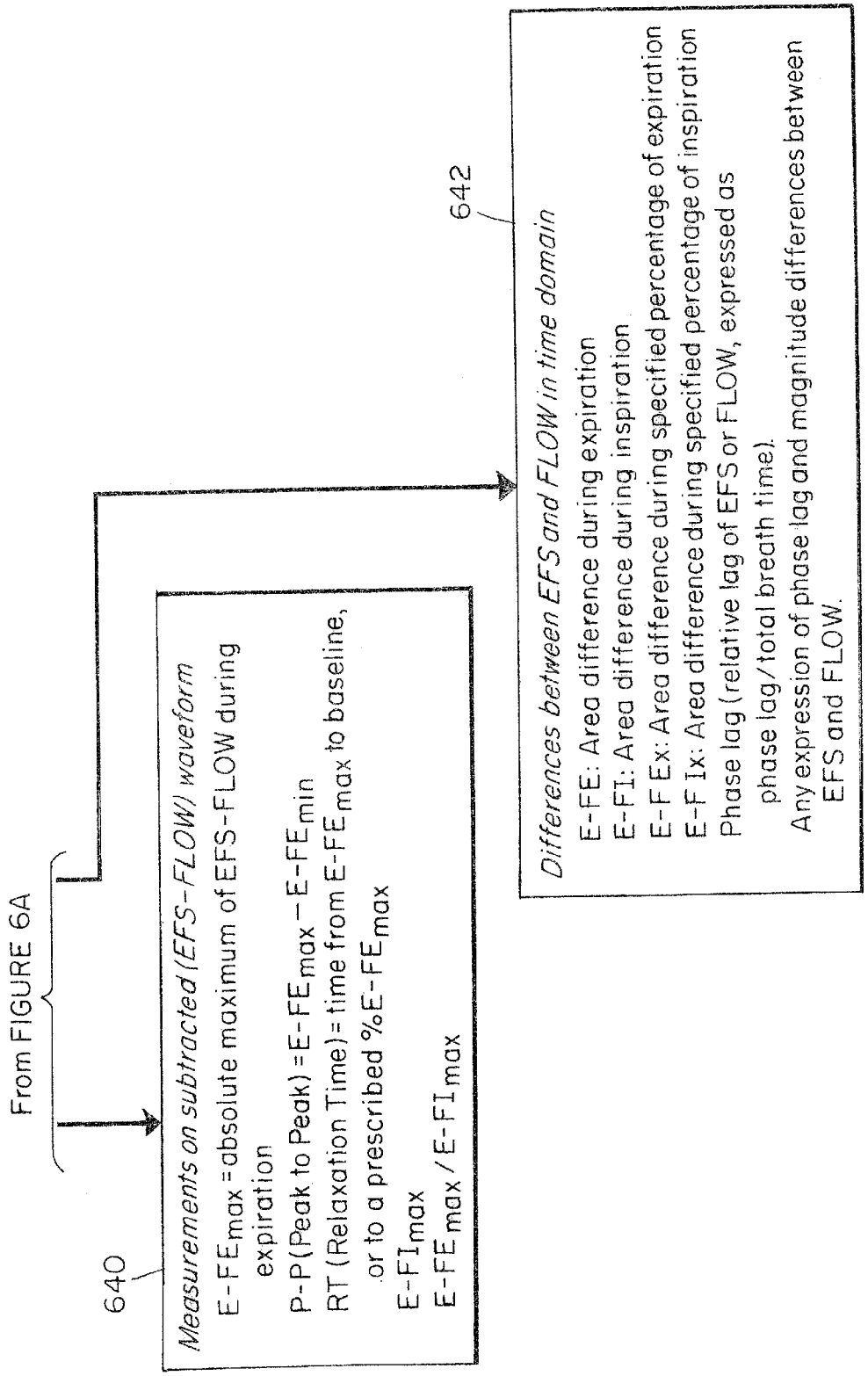

Referring to FIGS. 6A and 6B two external sensors, one for the abdomen 610 and another for the rib cage 612 are calibrated. The gains of each sensor are set to correspond to a pre-selected tidal volume. The external sensors, both for the abdomen and the rib cage, are then applied onto the subject at the respective locations 614, 616. The abdominal sensor results in a signal 618 which is the effort or external flow signal indicative of volume changes measured in the abdominal region. This abdominal waveform is differentiated per step 620. The rib cage sensor results in a signal 622 which is differentiated to result in the differentiated waveform indicative of the external flow signal per step 620. In addition, the two signals originating from the rib cage and the abdomen are summed in the summer 626 and the derivative of the two signals is then taken to result in a differentiated sum waveform 628. The three differentiated signals or waveforms 620, 624, 628, resulting from the abdomen, the rib cage and the summed signal, are displayed real time 632 and compared with the flow signal 632 either by visually displaying and overlapping the waveforms or by synthesizing a composite waveform per step 634 indicative of the point-by-point subtraction of the flow signal from the effort signal. The external effort signals or waveforms are normalized per step 636 by offsetting the signal to match an area under the inspiratory flow waveform. The step of normalization 636 is optional. The signals that result from the comparison of the external effort signal and flow signal are then processed by applying a process sequence per step 638. The measurements applied to the composite waveform resulting from subtracting the flow from the effort signal or external flow signal (EFS) are provided in step 640. One process sequence comprises subtracting the maximum flow during expiration from the absolute maximum effort signal. Other processes which can be applied comprise peak-to-trough measurements of the subtracted waveforms during expiration. An alternative measurement of the composite waveform (EFS-Flow) comprises calculating a relaxation time signal which is indicative of the time from the peak composite signal to the trough during expiration or from the peak to a prescribed percentage of the peak composite signal during expiration. Other measurement processes comprise subtracting the maximum inspiratory flow from the effort signal or a ratio of the maximum flow during expiration subtracted from the effort signal to the maximum flow during inspiration subtracted from the effort signal.

Other methods for comparing the overlapping signals indicative of effort and flow in the time domain are provided in step 642. One such method comprises measuring the area difference during expiration, or measuring the area difference during inspiration. Alternatively, the area difference during a specified percentage of expiration or inspiration can also serve to highlight the difference between the effort and the flow signals in the time domain. Alternatively, the relative phase lag between the effort or the flow signals expressed as a ratio of phase lag to the total breath time could also provide the difference between the two signals. Thus, generally any expression of phase lag and magnitude difference between the effort and flow signals provide the measures for the overlapped comparison signal.

Figure 6C:
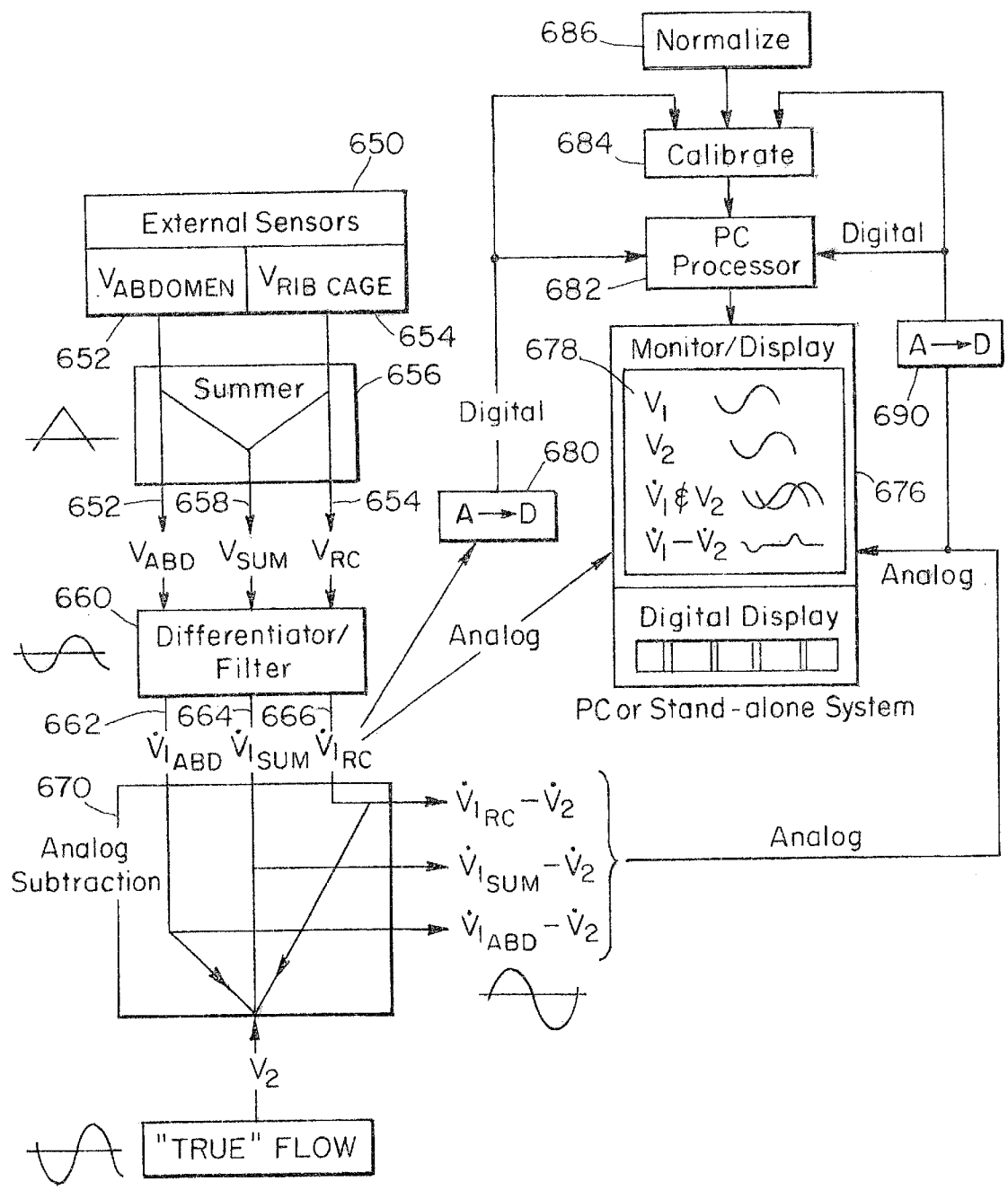
FIG. 6C is a schematic diagram of the hardware components required to implement the method for measuring respiratory function in accordance with the present invention.

Referring to FIG. 6C, a schematic diagram of the hardware components required to implement the system for measuring the respiratory function in accordance with the present invention is illustrated. External sensors 650 to measure effort, both from the abdominal and rib cage region., are applied to the subject and signals indicative of the effort required both from the abdominal region 652 and the rib cage region 654 are collected and summed in summer 656. The resultant signals, $V_{sum}$ 658, $V_{rc}$ 654 and $V_{abdomen}$ 652 provide input into a differentiator and filter 660. The signals as measured from the subject are indicative of a volume change during breathing and are differentiated to result in a flow signal represented by Vdot. Filtering of the differentiated signal is required to filter noise components added by the process of differentiation. The resultant signals $Vdot_{abdomen}$ 662, $Vdot_{sum}$ 664 and $Vdot_{rc}$ 666 form the inputs into an analog subtraction device 670. True flow 672 as measured by the pneumotachograph, is subtracted out from the differentiated signals resulting in the difference between the effort signals as represented by the signal for the rib cage, the abdomen and the sum, and the true flow signal. The analog signals then form inputs into a processing system 676 and are displayed on a monitor or a display 678. In the alternative, the signals that result from the analog subtractor 670 are digitized in an analog to digital converter 680 providing input into a processor 682. The output of the processor 682 is then displayed on a monitor 678. Calibration information 684 provides an input into the processor 682 which is used to normalize the effort signal per step 686 to an inspiratory area for example, or any other parameter to provide for magnitude comparisons of the effort and flow signals. In the alternative, the analog signals that result from the analog subtractor 670 can be displayed using the monitor 678. An analog to digital converter 690 can then convert the analog signals resulting from the analog subtractor 670. The digitized signals provide inputs into the processor 682 for further processing.

Figure 6D:
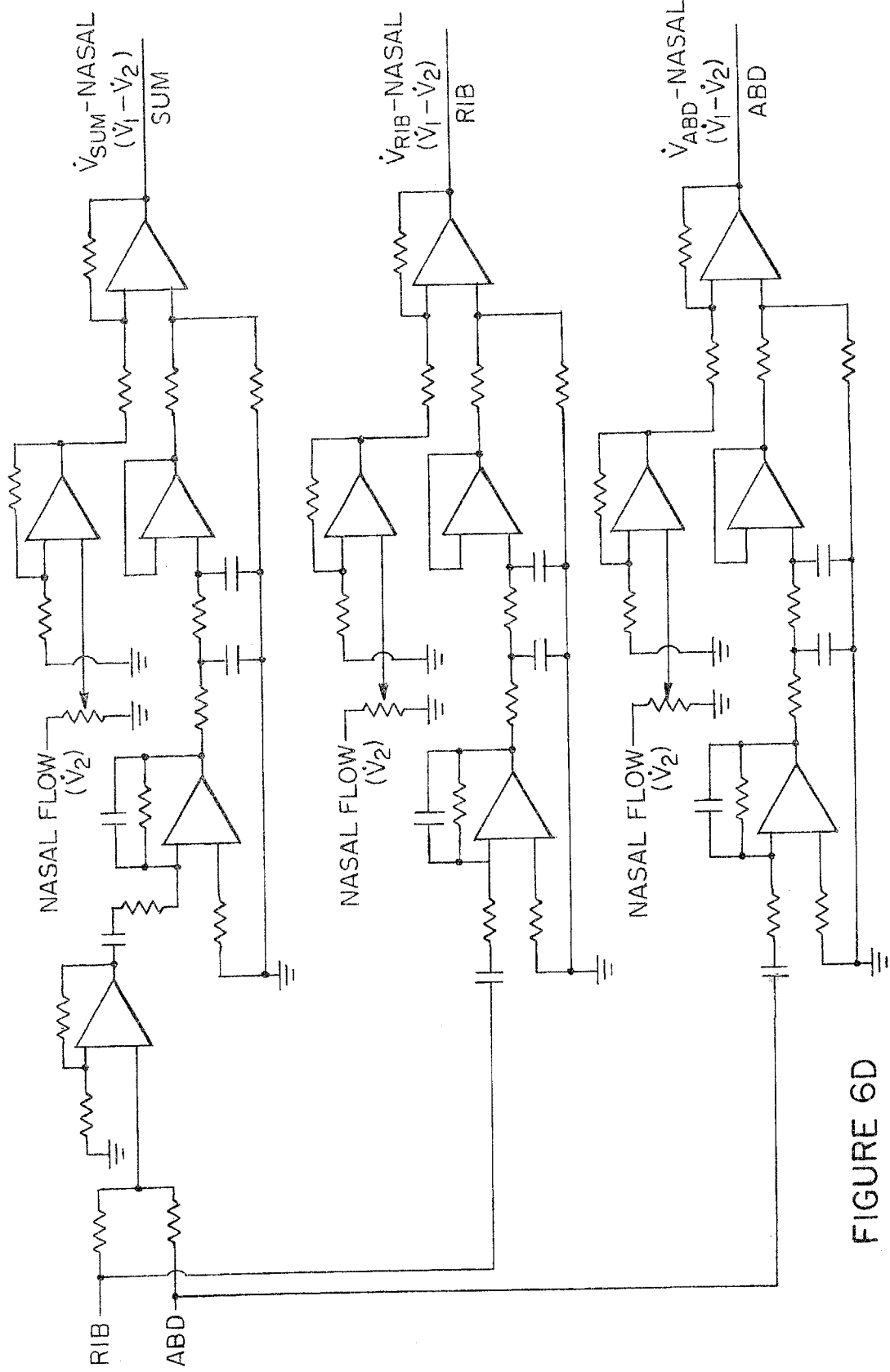
FIG. 6D is a schematic diagram of an exemplary circuit used for analog subtraction as described in FIG. 6C.

Referring to FIG. 6D, an exemplary circuit diagram for the analog subtractor described in FIG. 6C is illustrated. Essentially, the effort signal as measured from the rib cage is summed, with the effort signal as measured from the abdominal region to result in a sum signal. The nasal flow signal indicative of the airflow is then subtracted from the sum signal to result in the signal $V_{sum}$-NASAL. In addition, the nasal flow signal is subtracted from the effort signal as measured from the rib cage alone is subtracted from to result in the signal $V_{rib}$-NASAL. Further, the nasal flow signal is subtracted from the effort signal as measured from the abdominal region alone to result in the signal $V_{abd}$-NASAL.

Figure 7:
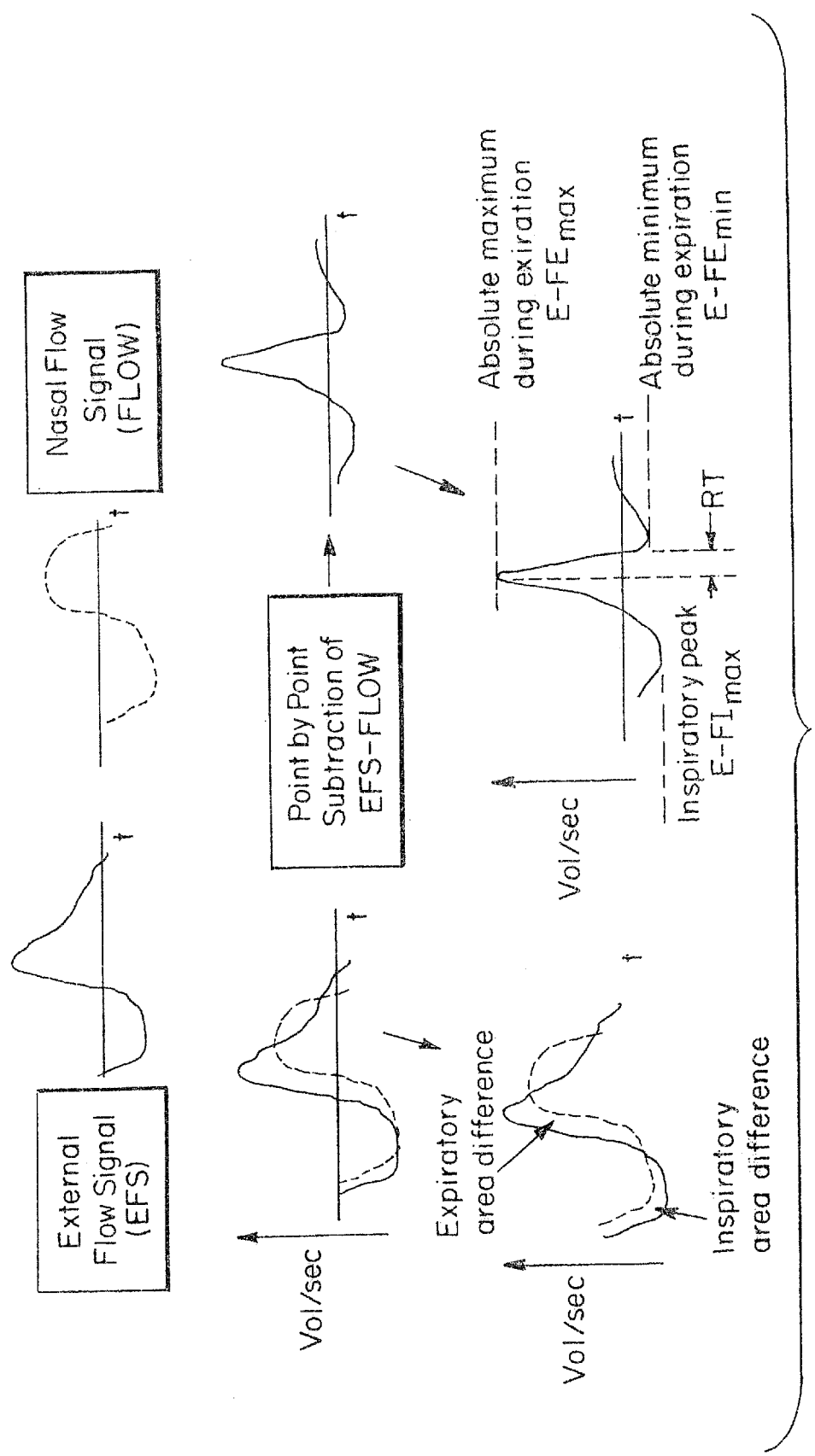
FIG. 7 illustrates graphically the signals that are processed in accordance with the present invention.

Referring to FIG. 7, the signals as measured, both the external flow signal (EFS) which represents the effort signal and the nasal flow signal which represents the true airflow signal, are graphically illustrated. The figure further illustrates the two methods that may be used to compare the differences between the effort and flow signals. A first method includes a point-by-point subtraction in the time domain of either analog or digital signals indicative of external flow and the flow which then results in a signal indicative of a composite waveform, from which the absolute maximum flow during expiration, and absolute minimum flow during expiration can be gauged. In addition, a second method includes the comparison of the waveforms by overlapping waveforms to result in a visual expiratory area difference or an inspiratory area difference. In the alternative preferred embodiment, Fourier analysis may be used to compare the signals indicative of external flow and the uncompressed airflow.

Figure 8A:
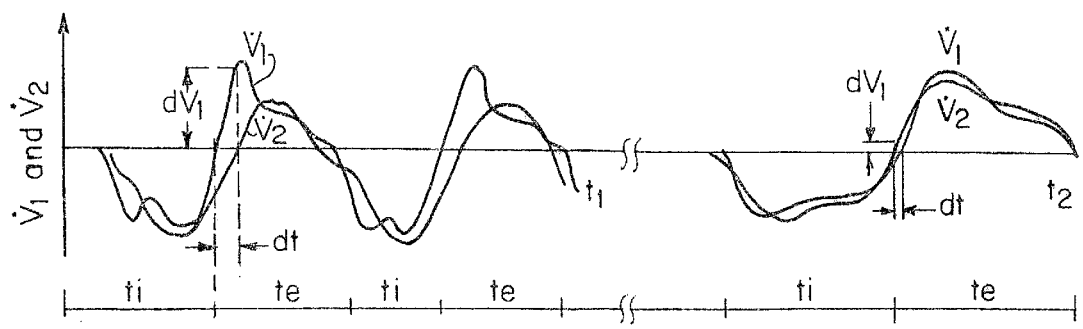
FIGS. 8A–8D graphically illustrate the effort and flow signals measured and processed and their comparison to pleural pressure.
Figure 8B:
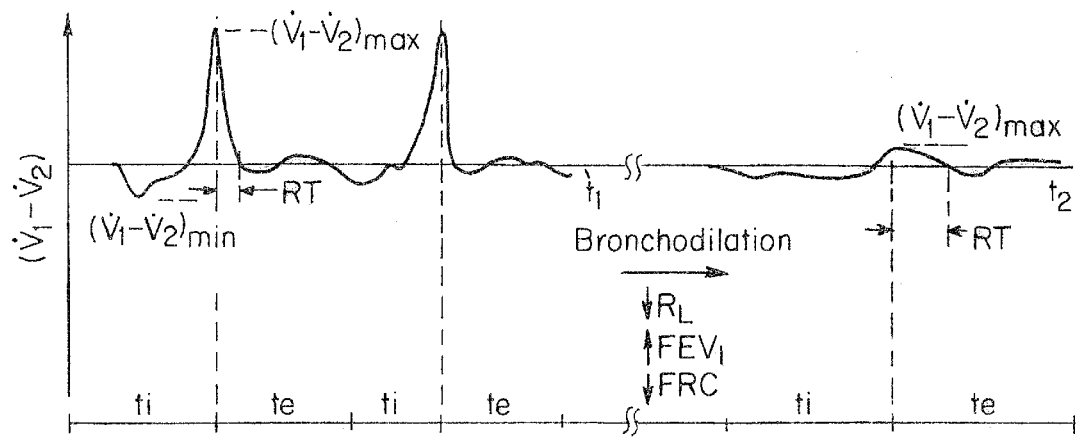
Figure 8C:
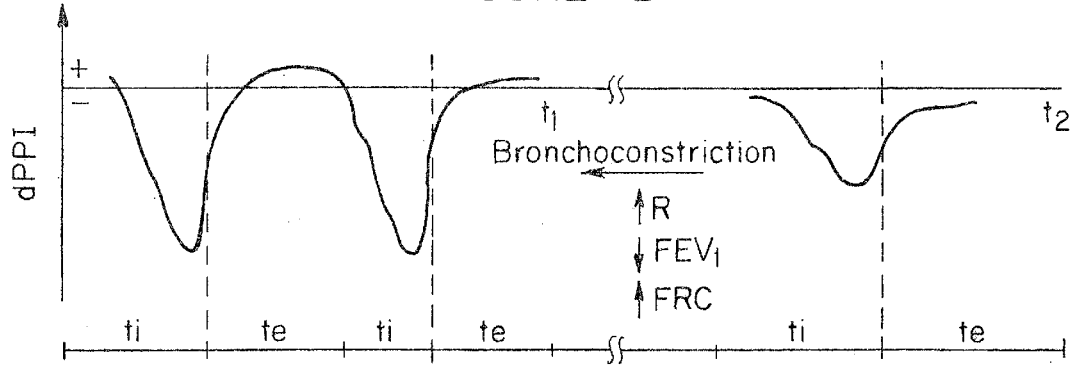
Figure 8D:
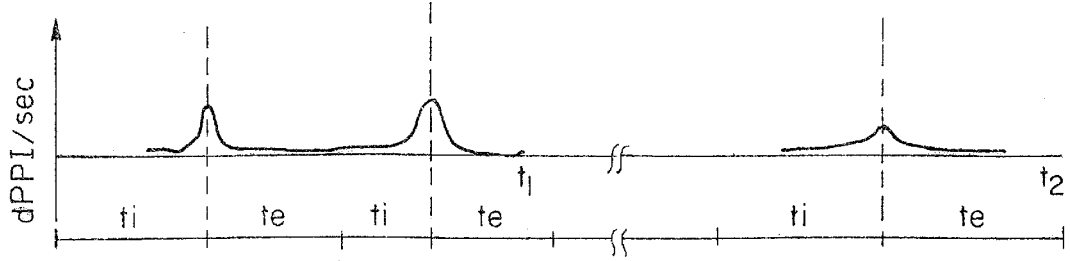

Referring to FIG. 8A, the graphical illustration is a visual comparison of the effort signal $Vdot_1$, and $Vdot_2$ which is the flow signal for a subject having an obstructive pulmonary disease. Upon administration of a bronchodilator the difference both in magnitude and phase between the effort and flow signal are reduced as represented by the later portions of FIGS. 8A and 8B. FIG. 8B graphically represents the composite signal or waveform that results from the point-by-point subtraction of flow from the effort signal achieved in the analog or digital domain. These are then compared to the transpulmonary pressure dPPI signals shown in FIG. 8C and the rate of change of the transpulmonary pressure signal shown in FIG. 8D which is a standard for measuring obstructive pulmonary disease. The peak acceleration of dPPI coincides with peak $Vdot_1-Vdot_2$ which shows that the latter is the result of gas compression and airway resistance in the chest. The system of the present invention may be used for monitoring obstructions, or monitoring relief of obstructions during bronchodilation and for monitoring bronchial challenge with a bronchoconstrictor agent as the composite waveform provides a visual indication of obstructions or changes in the physiology of the subject after administering bronchodilators or bronchoconstrictors.

Figure 9A:
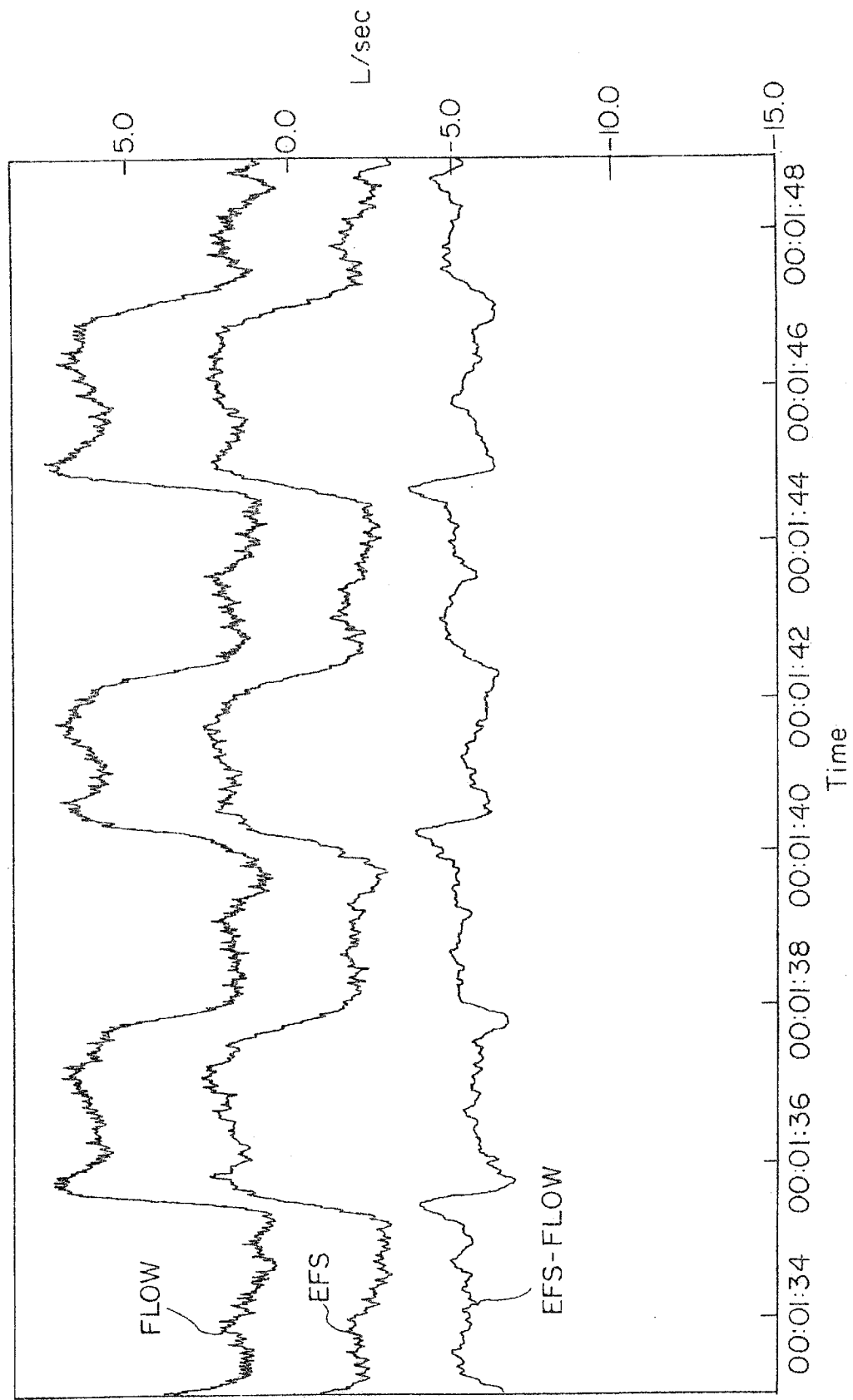
FIGS. 9A–9B graphically illustrate the effort, flow and comparative signals as measured and processed from an equine subject in accordance with the present invention.
Figure 9B:
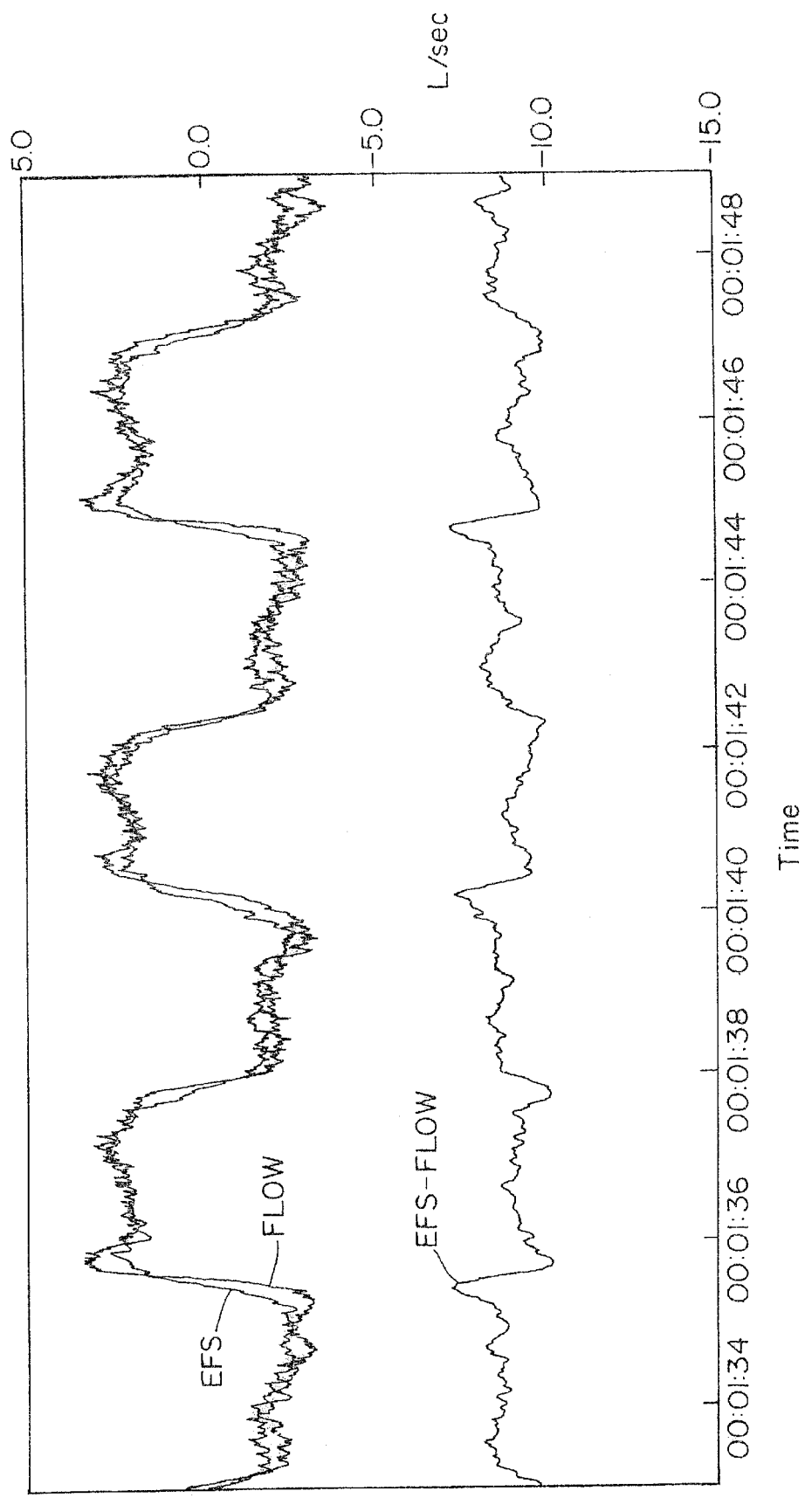
Figure 10A:
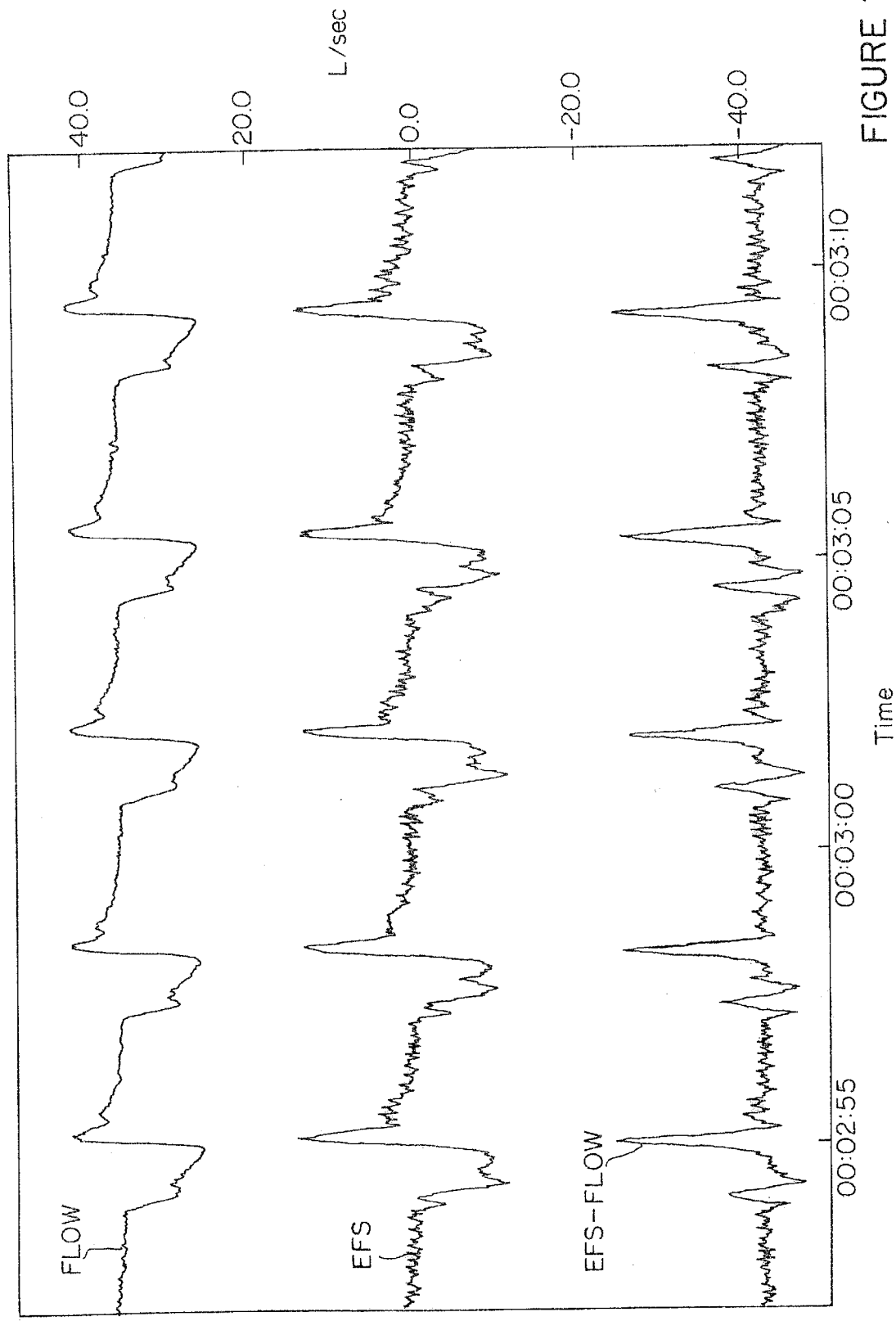
FIGS. 10A–10C graphically illustrate the effort, flow and comparative signals as measured and processed in accordance with the present invention from an equine subject with chronic obstructive pulmonary disease.
Figure 10B:
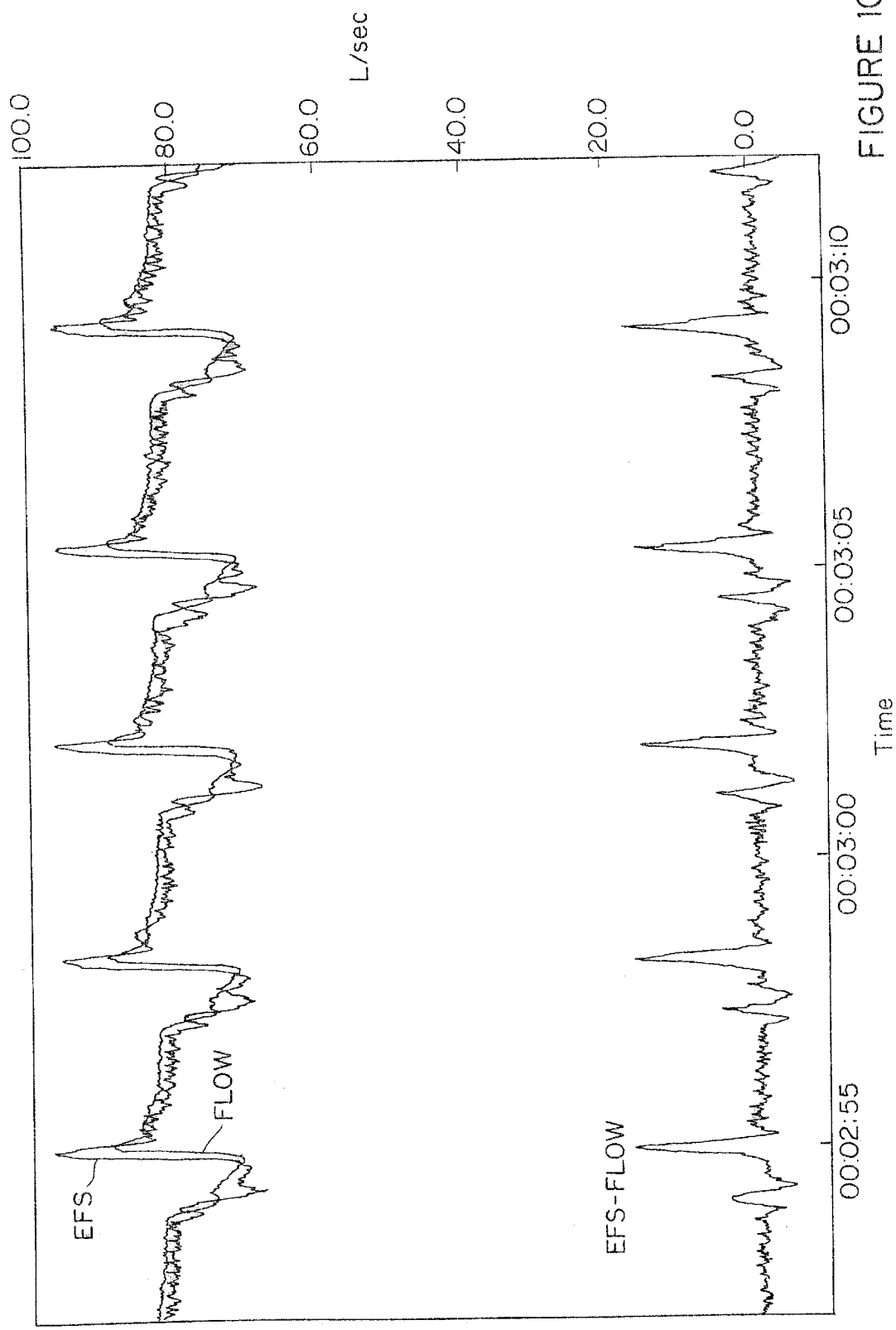

Referring to FIGS. 9A and 9B, lung dysfunction can be measured by comparing an external measurement of flow (EFS) with flow measured at the airway opening in exactly the same time domain. FIGS. 9A and 9B provide an example of the processing of signals in a normal equine subject without an airway obstruction. Flow closely matches the EFS signal in a normal horse in that there is no or minimal phase lag or magnitude difference. FIGS. 10A and 10B provide examples of the effort and flow waveforms of an equine subject with chronic obstructive pulmonary disease. The two component waveforms of effort and flow are compared by overlapping or by actually subtracting point-by-point, true flow from the external flow signal, to obtain a third composite waveform which is depicted in FIGS. 10A and 10B as the signal indicative of EFS-flow. The overlapping of waveforms allows quantitative comparisons based on the phase lag and magnitude differences between the signals. Aspects of the composite waveform (external flow signal-flow) can be measured directly using various dimensions and time related data that measure lung dysfunction. The individual component and composite waveforms provide signals for real time visual monitoring. The comparison of the two measures of flow, both external flow and true flow, in the same time domain is an important part of the present invention as both the magnitude and phase relationships are compared.

Figure 10C:
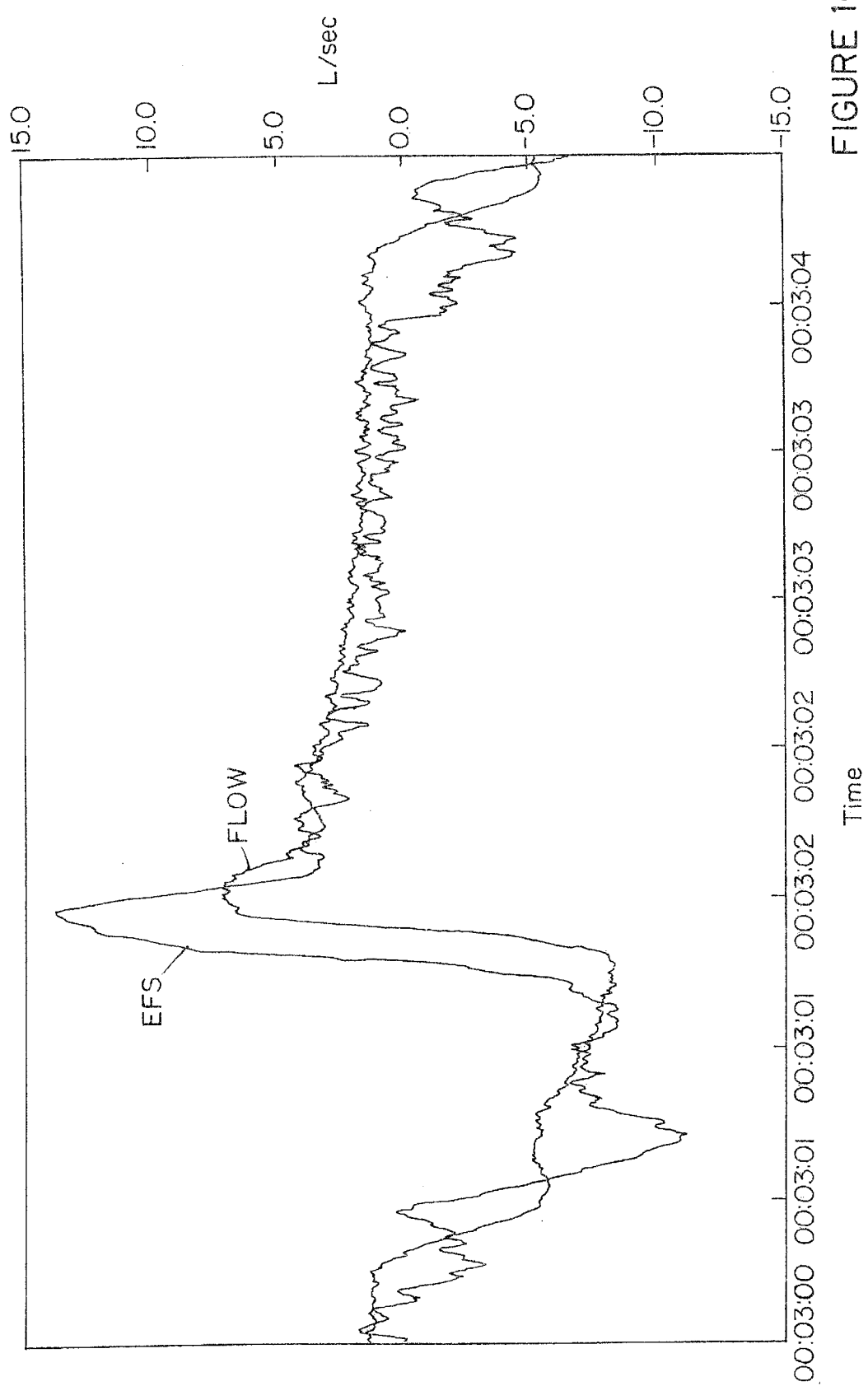

Referring to FIG. 10C, the phase lag between the external and flow signals in the horse with chronic obstructive pulmonary disease, is illustrated. The EFS signal leads the flow signal. An important feature of the methodology of the present invention therefore, is to examine the asynchrony of waveforms. The more asynchronous, i.e., the greater degree of phase lag observed for nasal flow, the greater is the airway obstruction. The difference in magnitude and phase between external and nasal flow correlates well with measures of pulmonary resistance and dynamic compliance. Asynchrony can be transient and instantaneous, but highly significant.

Differences in phase and magnitude between external and nasal flow measurements correlates with classical measurements of impedance. This suggests that the methodology of the present invention measures some combination of resistance, elastance, or inertance and the resultant gas compression in airways and lung tissue. Resistance is a component often used to measure the effects of bronchodilators and bronchoconstrictors. Elastance is a factor that describes the tendency of lung tissue to recoil during inflation. If small airways are obstructed, a smaller portion of the lung gets inflated, thus causing an increase in elastance. Inertance, is the force required to accelerate a column of air within the airways. Applying oscillatory mechanics theory, phase and magnitude differences at slow breathing frequencies are explained by the development of gas compression and resistance in small airways and tissues (i.e., changes in elastance and resistance). At higher breathing frequencies, the methodology of the present invention detects gas compression and resistance in larger airways (i.e., changes in inertance and resistance). As the present invention incorporates an external sensor of flow at the body surface, its output reflects respiratory drive and passive events, such as, lung elastic recoil and chest wall recoil and an effect on any of these components effects the external signal. It is emphasized that in the present invention external flow is compared with true flow. If one compares external flow or acceleration as measures of respiratory drive with ventilation also derived from the external sensor, the gas compressive effects will not be evident and a phase lag will not be measurable. This distinguishes the concepts of prior art which suggest the simultaneous use of external sensors for the measurement of respiratory drive and ventilation.

The methodology of the present invention, provides an indication whether the difference between external and nasal flow is occurring during the expiratory, as shown in FIGS. 10B and 10C, or during the inspiratory portions of the breath. This aids in determining the location of the obstruction. Differences in magnitude and phase of the two component waveforms during inspiration, suggest that a more proximal obstruction exists, and differences observed during expiration suggests a distal airway obstruction. External and nasal flow have to be compared in the same time domain, using both positive and negative scales to examine these phenomena real-time. This simplifies the monitoring of a patient by inspecting a single waveform.

Figure 10D:
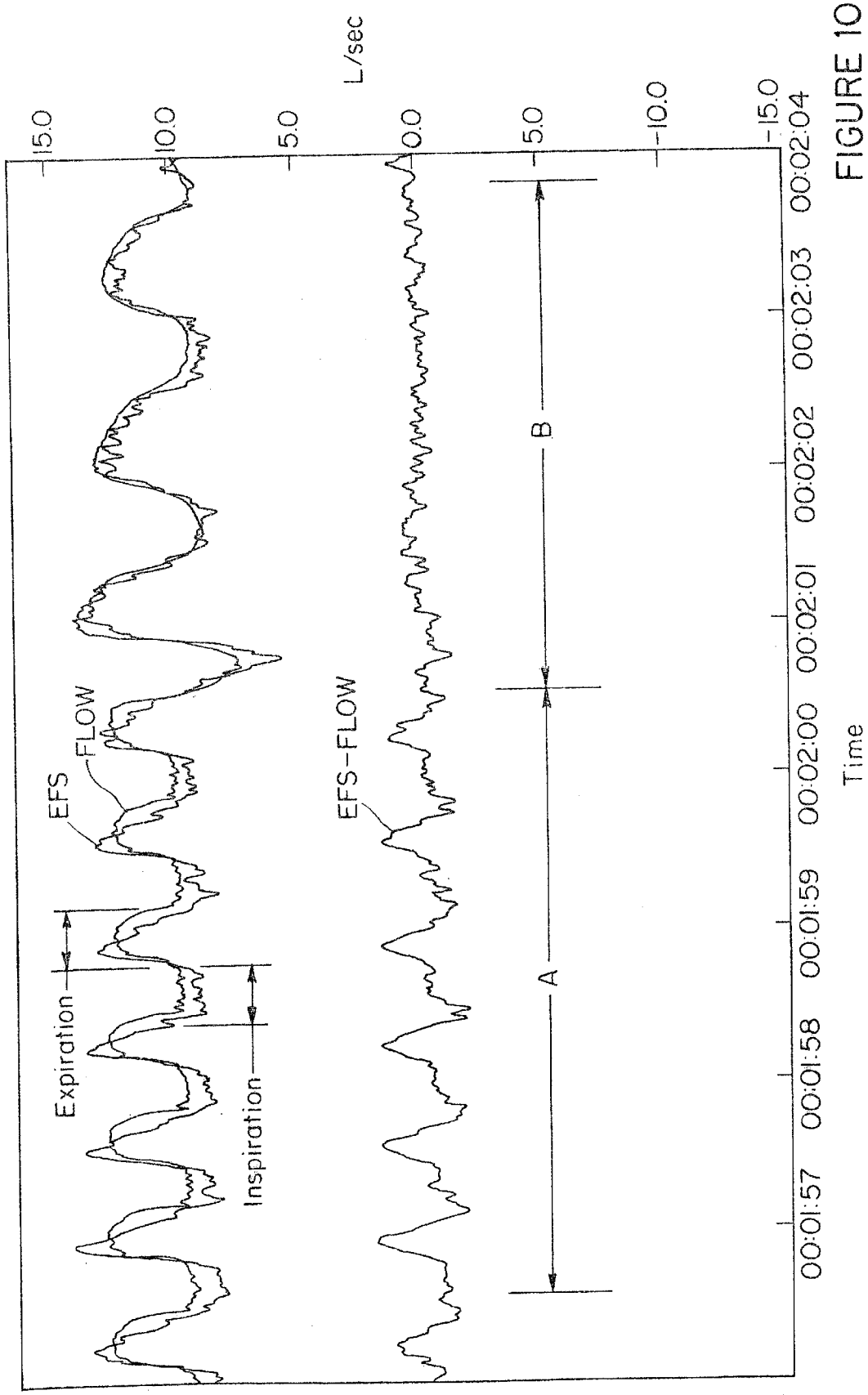
FIG. 10D graphically illustrates the effort, flow and comparative signals as measured and processed from a human subject.
Figure 11E:
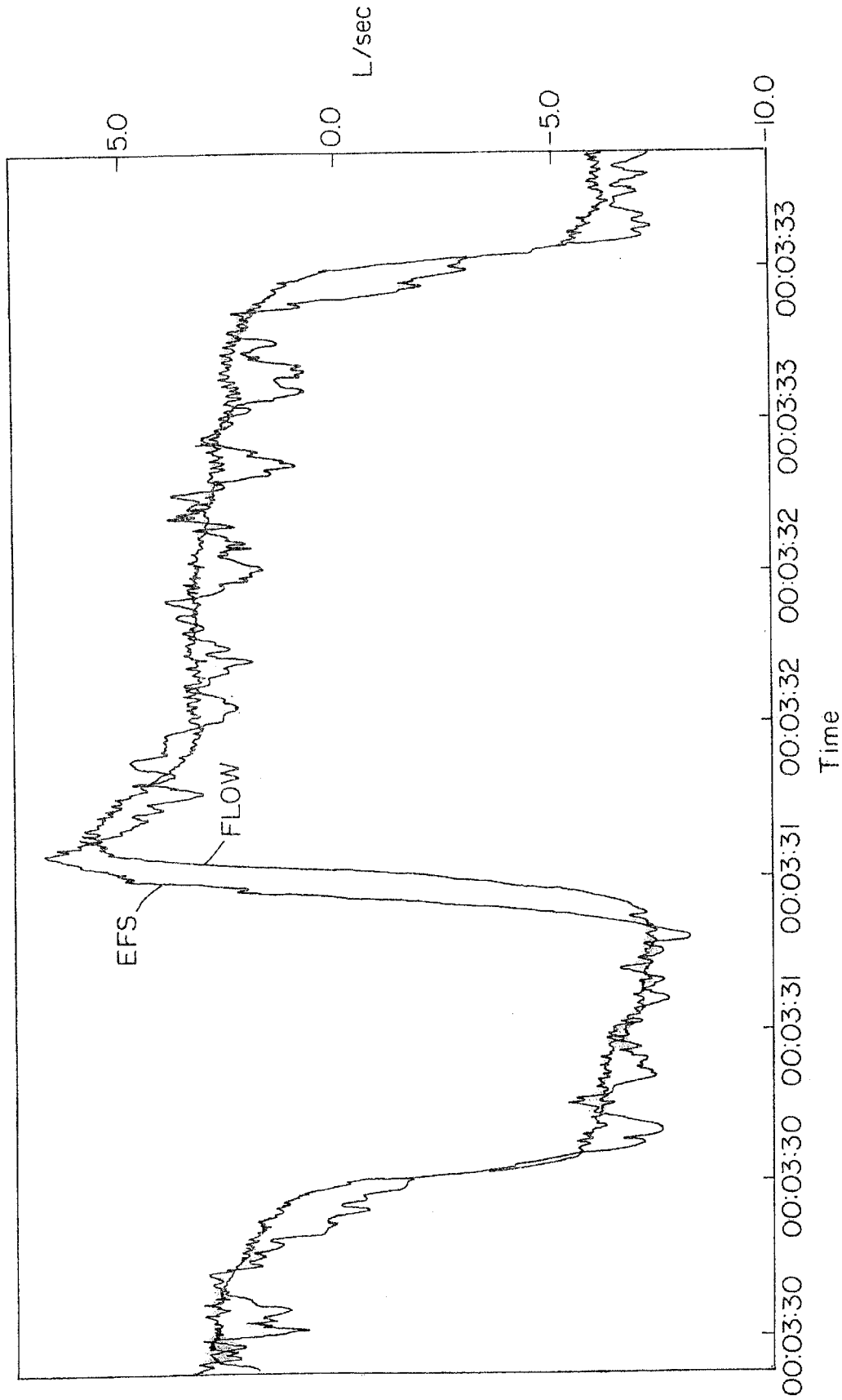

Referring to FIG. 10D, data from a human subject graphically illustrates the effort, flow and comparative waveforms as measured and processed in accordance with the present invention. Segment A is associated with a time period when the human subject had an airway obstruction. Differences in magnitude and phase of the two component waveforms of EFS and flow are relatively more pronounced during the inspiratory phase of the breath (which correlates with the valleys in the waveforms). This suggests that the obstruction is located in the upper airway or a more proximal obstruction exists. If the magnitude and phase differences of the two component waveforms of EFS and flow were relatively more pronounced during the expiratory phase of the breath, then the location of the obstruction would be located in the lungs and thus a distal airway obstruction is suggested. Therefore, the present invention provides an additional benefit of instantaneously providing location information regarding the airway obstruction. Segment B is associated with a time period when the human subject can breathe normally and is not influenced by an airway obstruction. The magnitude and the phase of the component waveforms track each other and there are no pronounced differences. The composite waveform (EFS-Flow) is relatively quiescent compared to the composite waveform segment representative of an airway obstruction.

The following tabulation for human subjects shows the correlation between a conventional measure of upper airway resistance to the composite waveform (EFS-Flow) peak amplitude as measured and processed in accordance with the present invention. The resistance of 1 cmH$_2$0/Liter/second corresponds to normal breathing without an airway obstruction. The peak amplitude of the composite waveform of 0.5–0.75 corresponds to a state of normal breathing without an airway obstruction in accordance with the present invention. As the resistance increases with increase in an obstruction of the upper airway, from 5 to 10 cmH$_2$0/Liter/second which relates to a moderate to severe obstruction, the peak amplitude of the composite waveform also increase from 3–4 to 5–7 Liters/second.

| Variable | | | |
| --- | --- | --- | --- |
| Resistance (cmH$_2$O/L/second) | 1 | 5 | 10 |
| EFS-Flow (peak amplitude) (Liters/second) | 0.5 | 3–4 | 5–7 |

The present invention can be used for monitoring the effects of various medications. As such, the respiration function signal provided after the processing of the input signals is measured before and after various challenges, or treatments are administered, such as, bronchodilators or bronchoconstrictors. The present invention uses bronchodilation response testing to evaluate the level of response of a horse with COPD as an indication for the initiation or continuation of therapy. It should be noted that airflow rates vary according to factors such as species, degree of illness, and body weight. Typically, a bronchodilator, such as albuterol, is administered by metered dose inhalers. In humans, the range of dose is 50 to 100 micrograms, in horses 450–900 micrograms. Bronchodilator treatments result in complete cessation of signs or partial cessation of signs of airway obstruction. In horses, there is typically a reduction in airway obstruction, measured in the form of lung resistance, of about 40 to 60% of a baseline. The composite waveform (EFS-Flow) peak amplitude, upon administering a bronchodilator to a horse, changes from 12.3 to 5.4 liters per second thus indicating a partial cessation of signs of airway obstruction.

Referring to FIGS. 11A–11E, following the administration of a bronchodilator, the patient with lower airway obstruction shows less magnitude and phase differences between external and nasal flow. The change in the waveform is visually obvious, and lends itself to a continuous visual monitoring of a display, similar to monitoring blood pressure or ECG. Following the administration of a bronchodilator to the patient with COPD (shown in FIGS. 10A, 10B and 10C), there is a greater overlap of external and nasal flow waveforms, and the resultant composite waveform synthesized by subtracting the nasal flow from the external flow signals has a smaller amplitude, especially during the expiratory portion of the breath. This indicates resolution of a lower airway obstruction and decreased amount of gas compression in the airways and lung tissue.

Figure 12A:
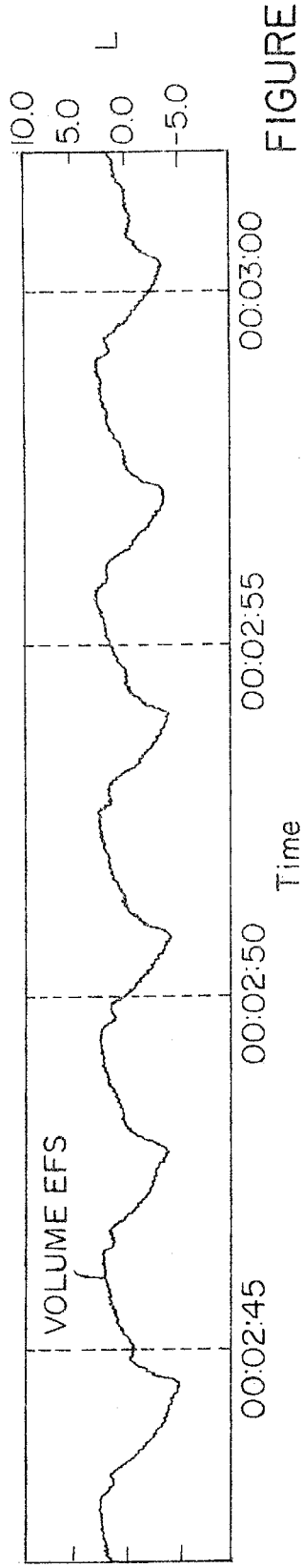
FIGS. 12A–12E graphically illustrate the effort, flow and comparative signals measured and processed from another equine subject having chronic obstructive pulmonary disease.
Figure 12B:
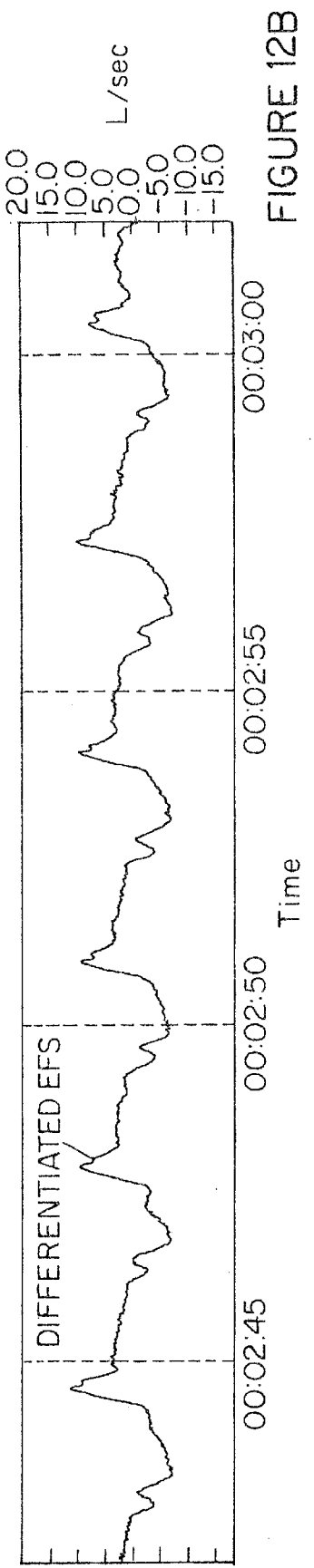
Figure 12C:
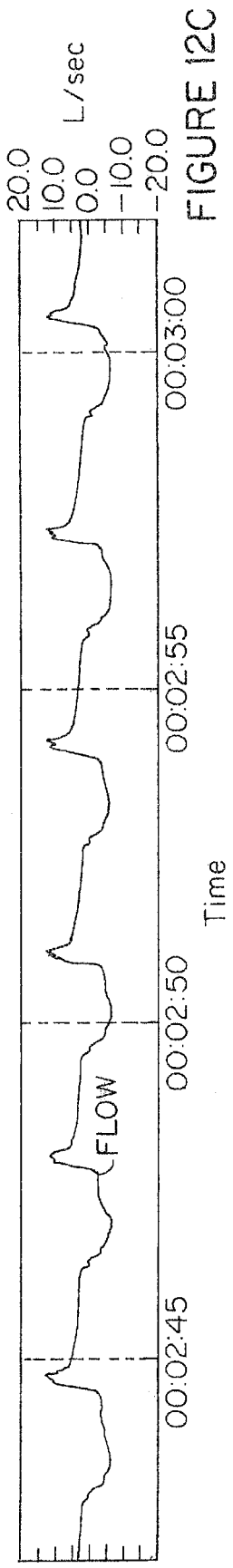
Figure 12D:
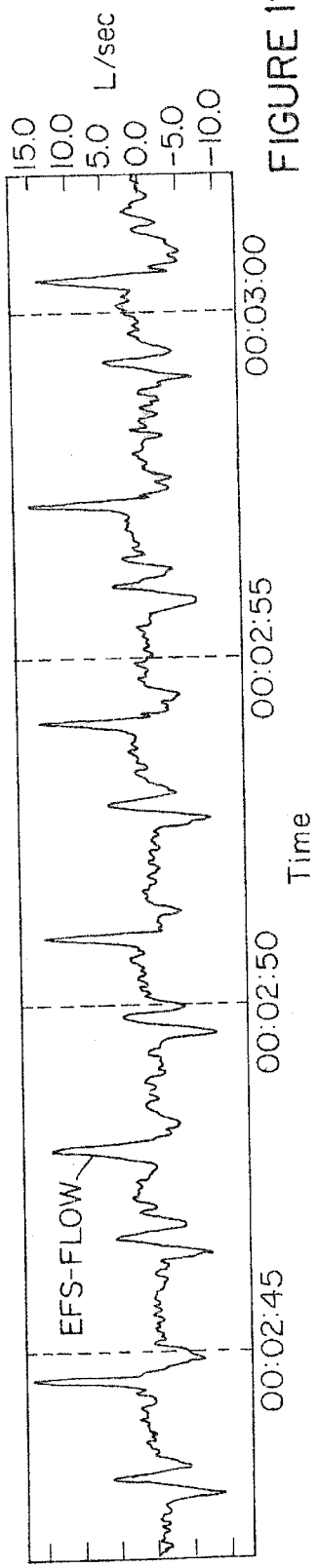
Figure 12E:
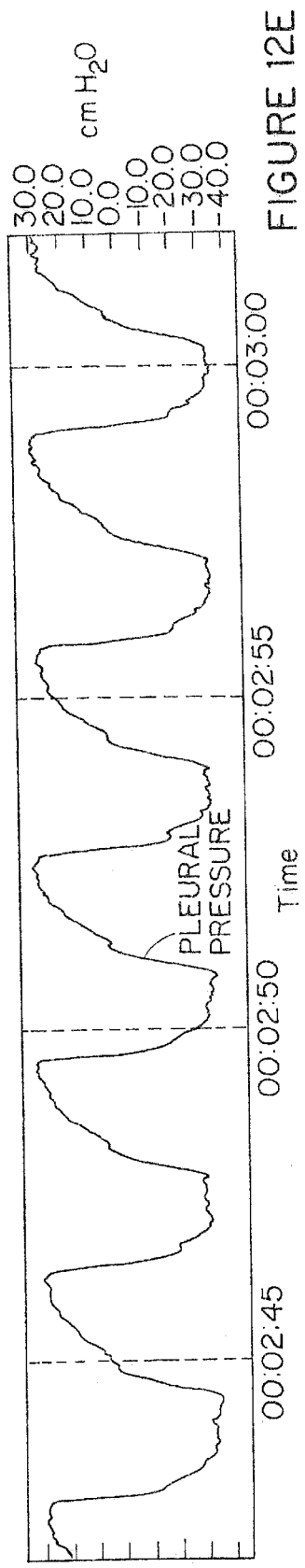
Figure 12F:
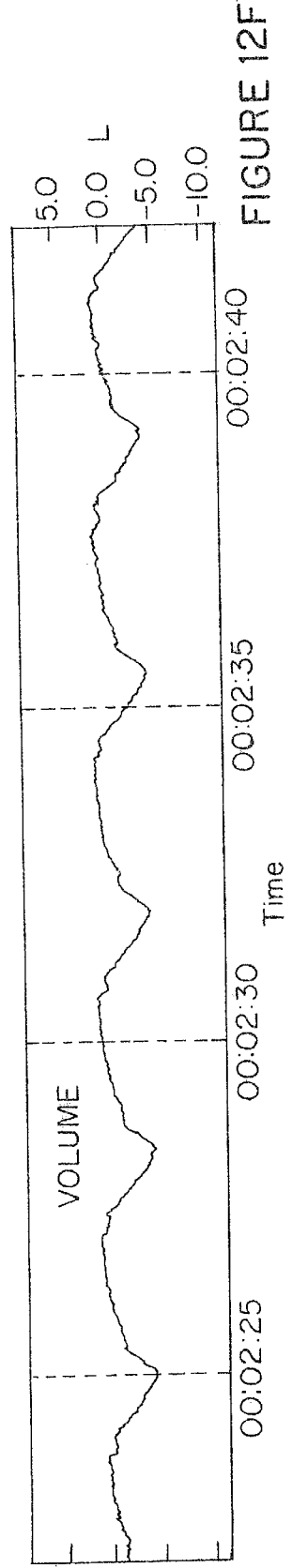
Figure 12J:
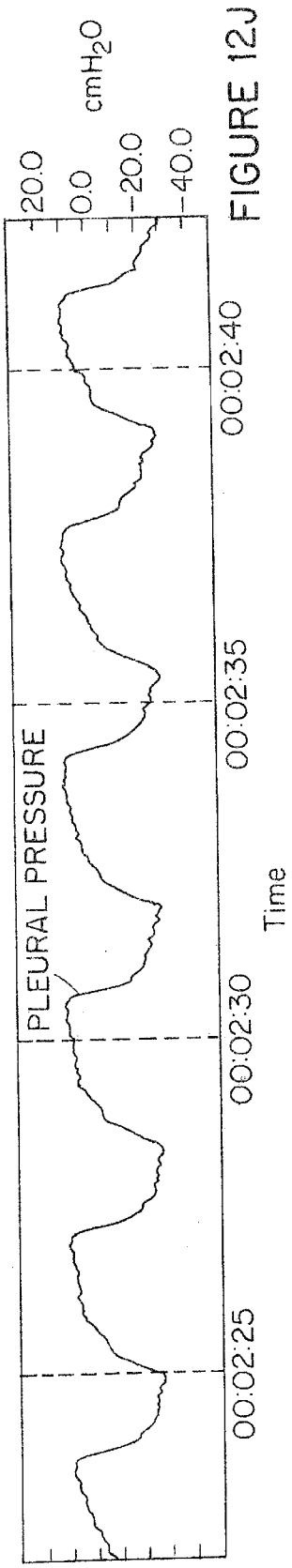
Figure 12K:
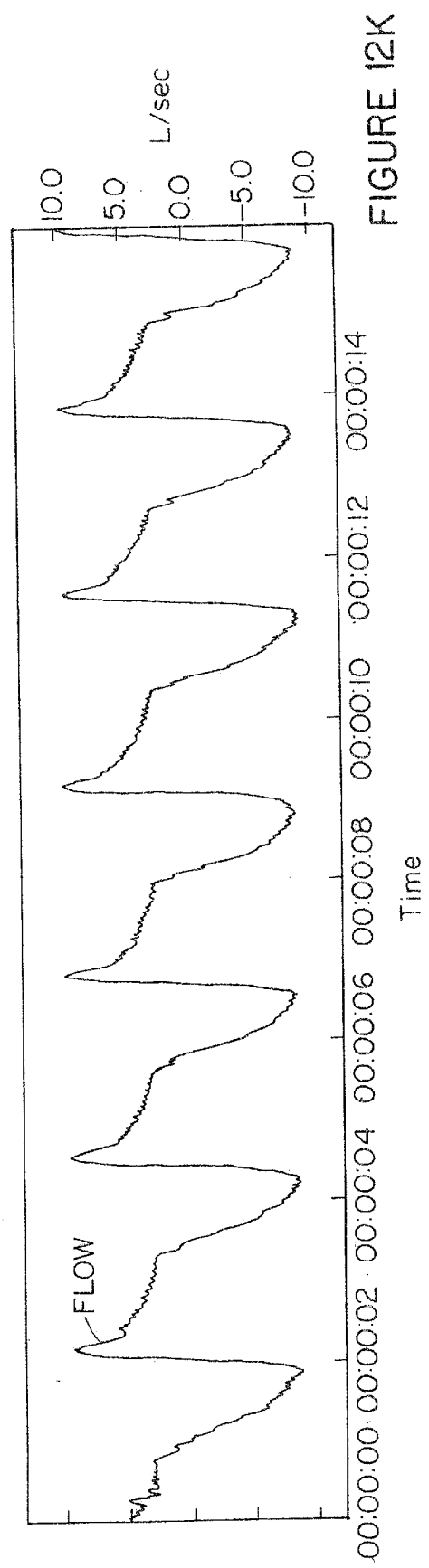

The methodology of the present invention to discern the phase difference between external and nasal flow is important. In some obstructed patients the external measurement of respiratory drive or respiratory drive versus ventilation as an indication of obstruction does not reflect phase difference. For example, there is a marked improvement in the relationship between external and nasal flow, i.e., decreased magnitude and phase differences in equine subjects with COPD after bronchodilation treatment, but only modest changes in the respiratory drive which is the peak of external flow. This is illustrated in FIGS. 12A–12J. There is a change in the appearance of the waveform after bronchodilation as seen in FIG. 12I, which is useful for a monitoring system. There is a characteristic large amplitude spike followed by a rapid descent to below baseline. This rapid descent reflects both an instantaneous phase and magnitude difference, and is used to measure obstruction. The improvements in the difference of the external and nasal flow correlate well (r=0.92) with improvements in transpulmonary pressure, pulmonary resistance and dynamic compliance studied in a group of horses (n=7) with COPD. Thus, the phase differences characterize a fundamental mechanical disturbance in the respiratory function of a patient.

Figure 13A:
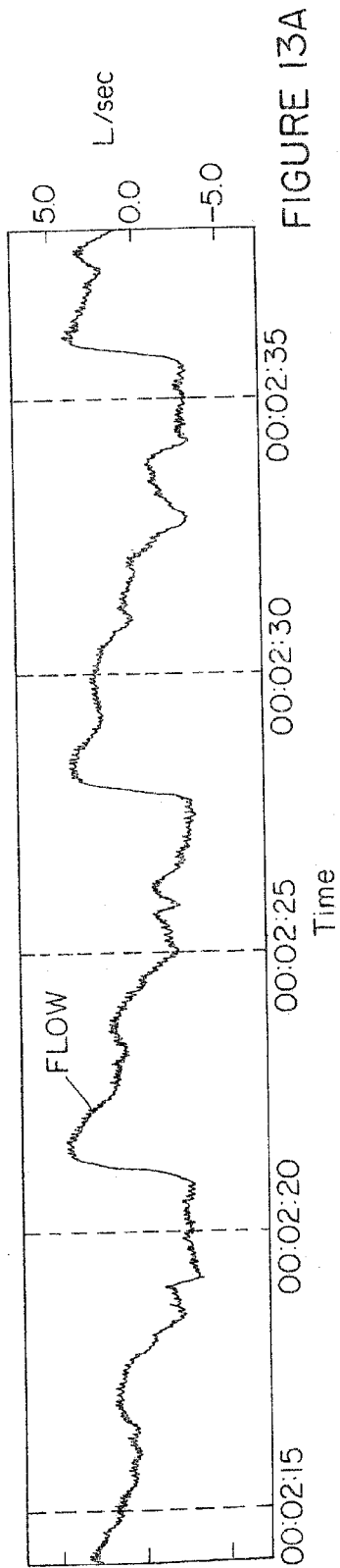
FIGS. 13A–13C graphically illustrates the effort signal measured only from the abdominal region of an equine subject without any airway obstructions, the flow signal and comparative signal determine after processing.
Figure 13B:
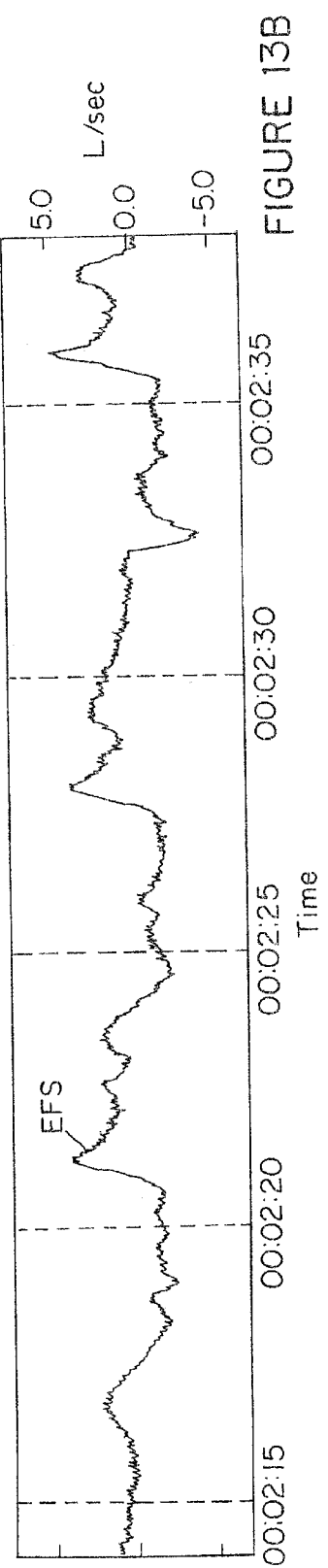
Figure 13C:
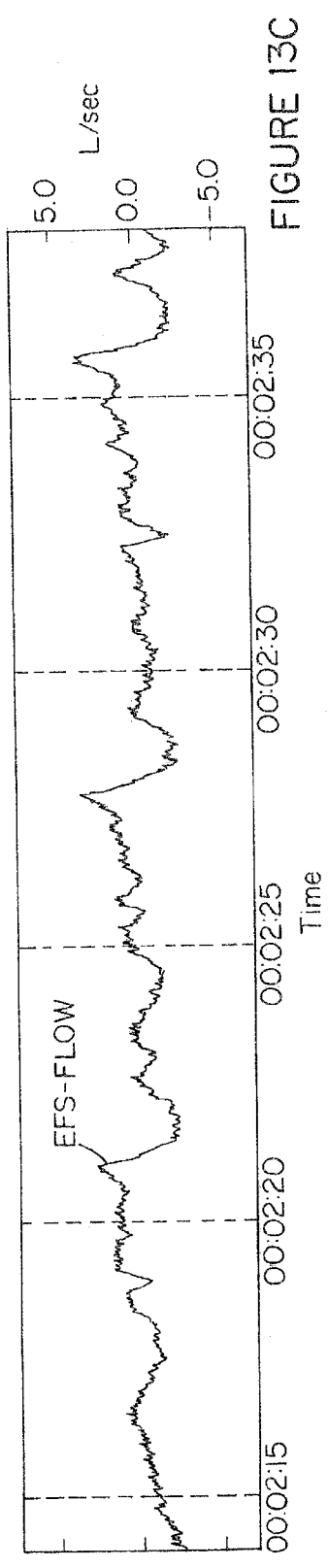
Figure 13F:
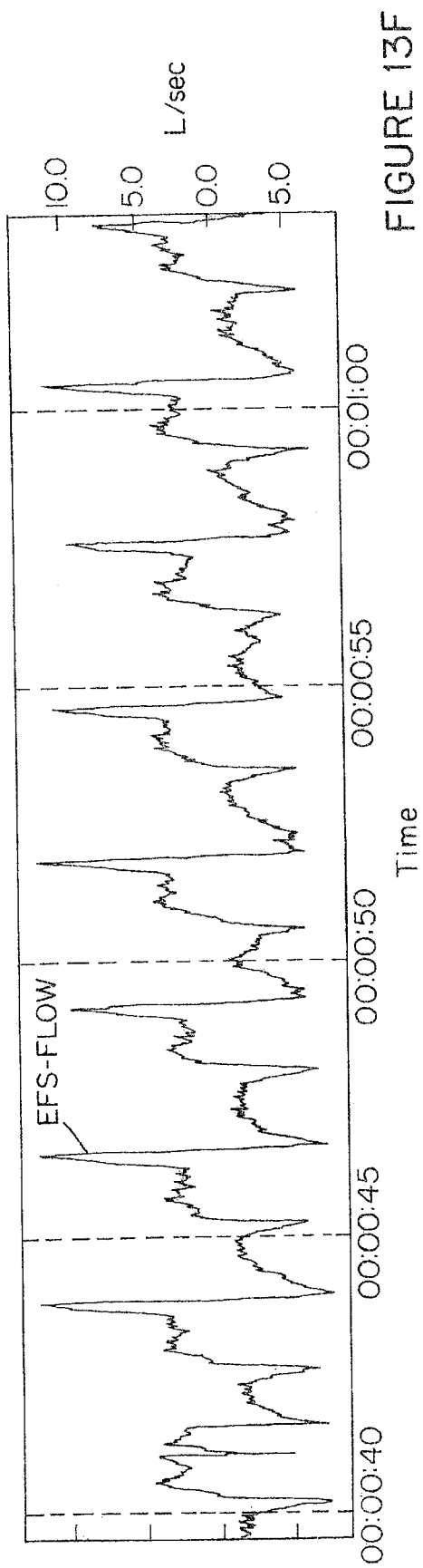

Referring to FIGS. 13A–13F, the administration of histamine to cause bronchoconstriction, on the other hand, results in increased differences in phase and magnitude for external and nasal flow measurements. This results in an increase in the composite waveform magnitude as shown in FIG. 13F. The waveforms from a normal horse before and after administration of histamine aerosol to the lung, as shown in FIGS. 13D–13F, shows an increase in the external minus nasal flow composite waveform (FIG. 13F) during expiration greater than during inspiration, illustrating the expected predominant effect of histamine on lower airways. These graphical illustrations also demonstrate that a single external sensor, placed around the abdomen, for example, could be used to measure bronchoconstriction. Alternatively, the combination of external sensors placed over the rib cage and abdomen can provide signals which can be electronically combined into a sum signal for comparison with flow, and the same results are obtained in the setting of a histamine challenge to the airways.

Figure 13G:
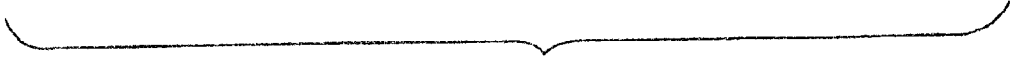
FIG. 13G is a tabulation of a classical measure of airway resistance as compared with a measure of airway resistance provided by the method for measuring respiratory function in accordance with the present invention.

Referring to FIG. 13G, a tabulation of a classical measure of airway reactivity LogPC65Cdyn, which is the provocative concentration of histamine that decreases dynamic compliance to 65% of a baseline, as compared with a measure of airway reactivity LogPC135SFEmax, which is the concentration of histamine that increases SFEmax to 135% of the baseline, as calculated by the method for measuring respiratory function in accordance with the present invention is provided. For subclinical lower airway obstruction, a test of airway reactivity includes bronchoprovocation of the subject using; a histamine (or other chemicals) to evoke bronchospasm as illustrated in FIGS. 13A–13F. A dose response curve is typically generated using a dose range from 1 mg/ml up to 32 mg/ml. The tabulation in FIG. 13G corresponds to data generated from the study of seven horses. A thirty five percentage (35%) increase in EFS-flow peak values (referred to as SFE max) correlated with a thirty five percentage (35%) drop in dynamic compliance, which is a classical measure of obstruction which decreases with airway obstruction. The correlations were greater than 0.9 ($p<0.05$) for Spearrmans rank correlation coefficient. This data illustrates that a simple point-by-point subtraction of the airflow signal from the effort signals provides evidence of transient gas compression and airway resistance during histamine challenge, and the methodology of the present invention can be employed effectively to measure airway reactivity.

Figure 14D:
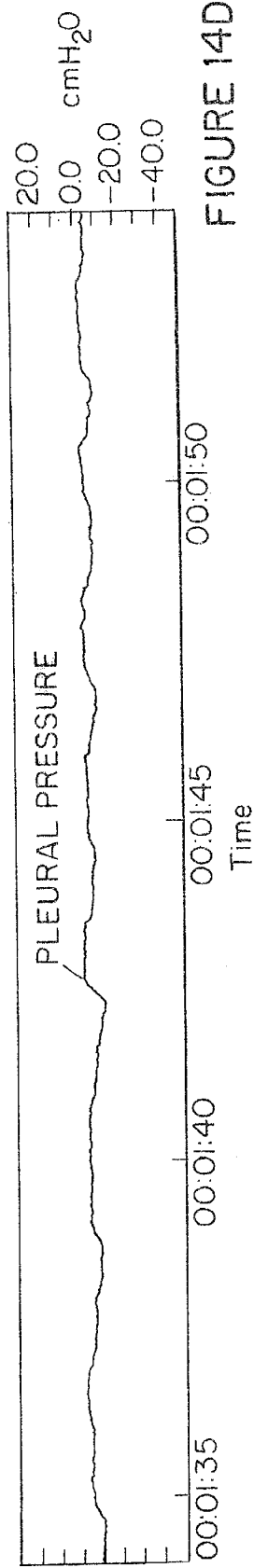
Figure 14E:
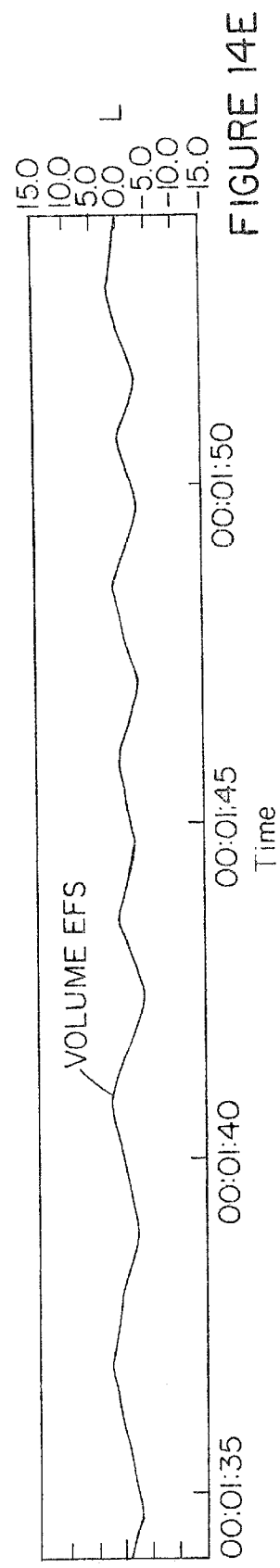
Figure 14F:
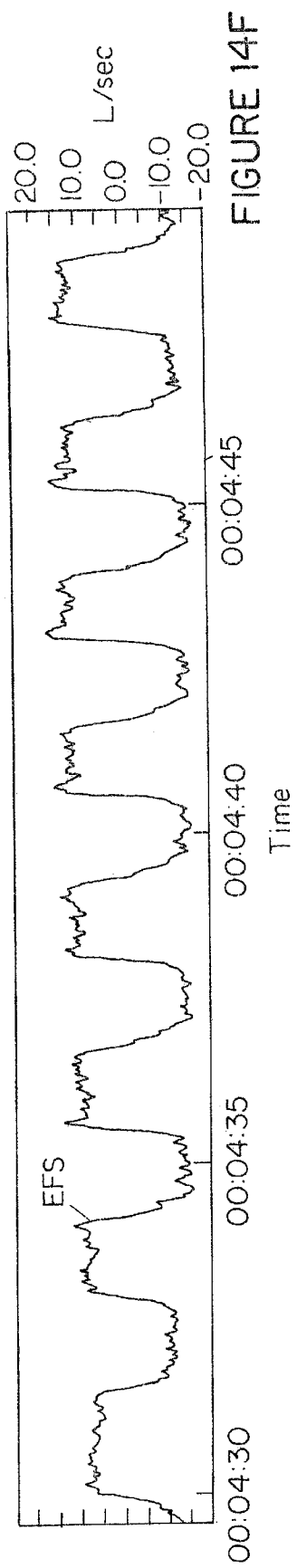
Figure 14I:
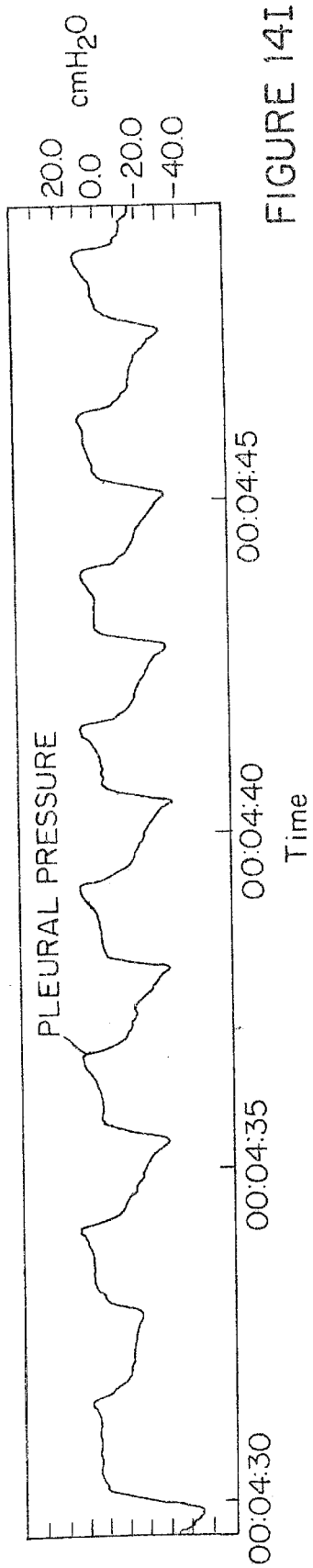
Figure 14J:
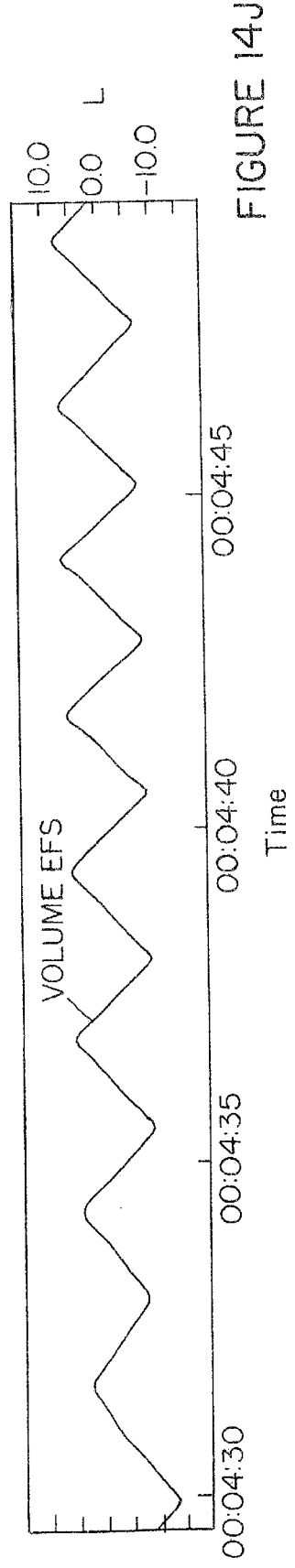
Figure 15D:
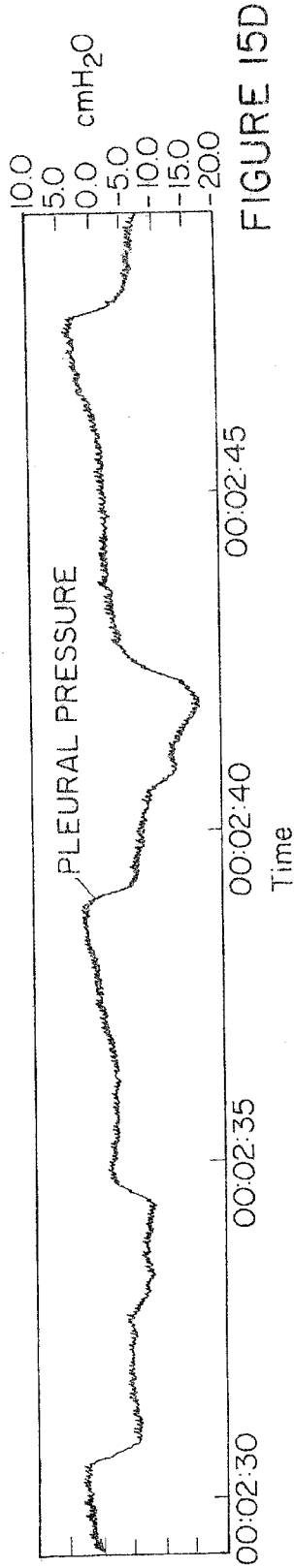
Figure 15E:
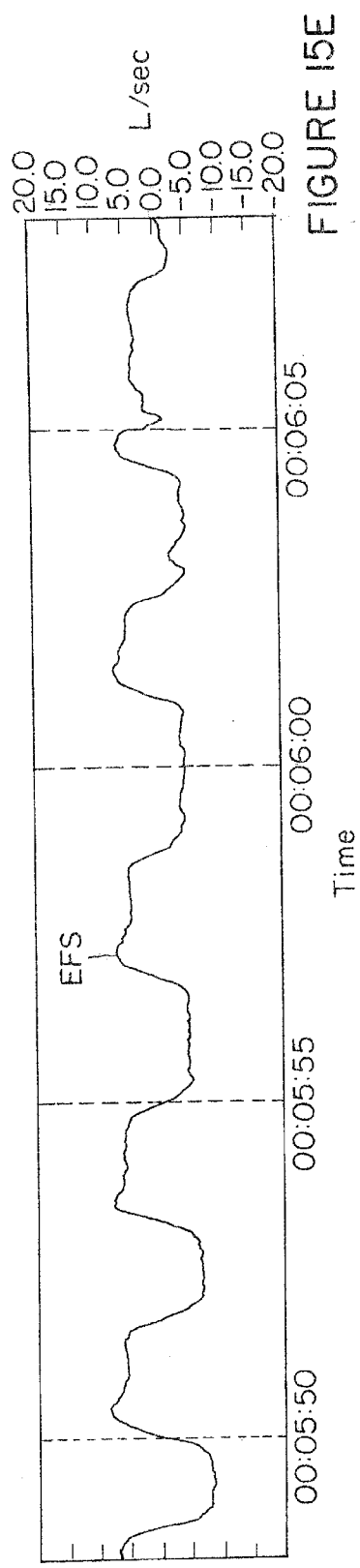
Figure 15F:
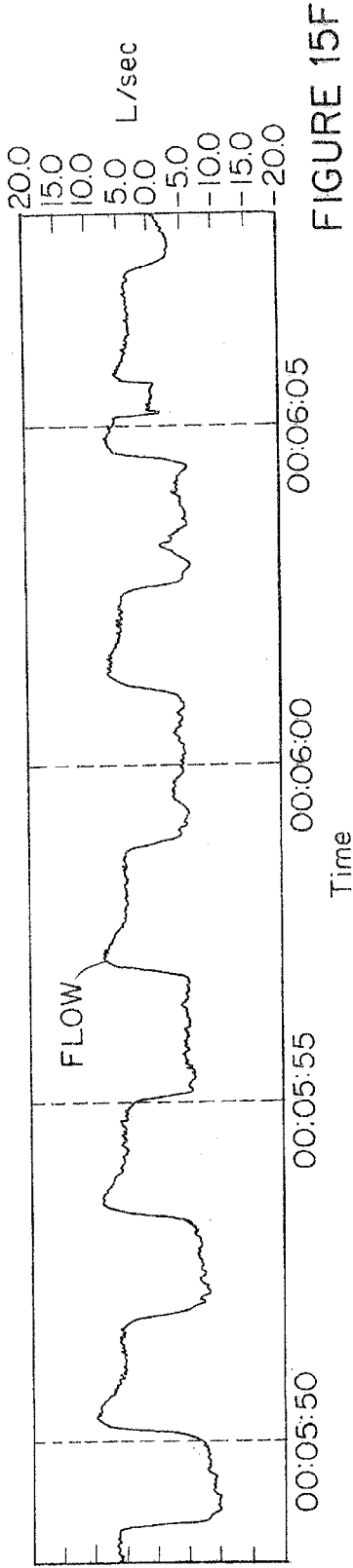
Figure 16C:
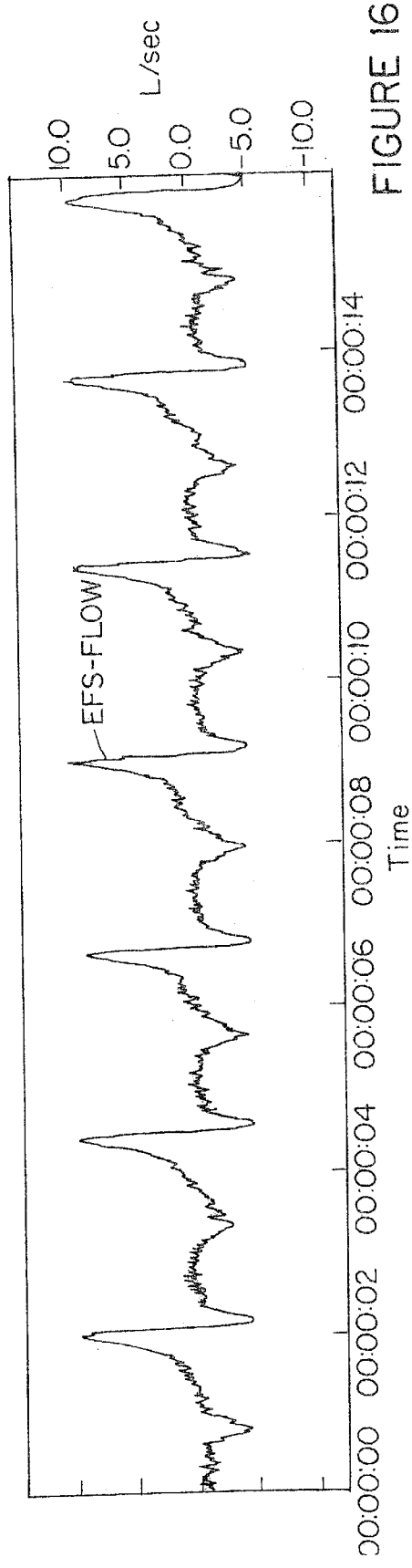
Figure 16D:
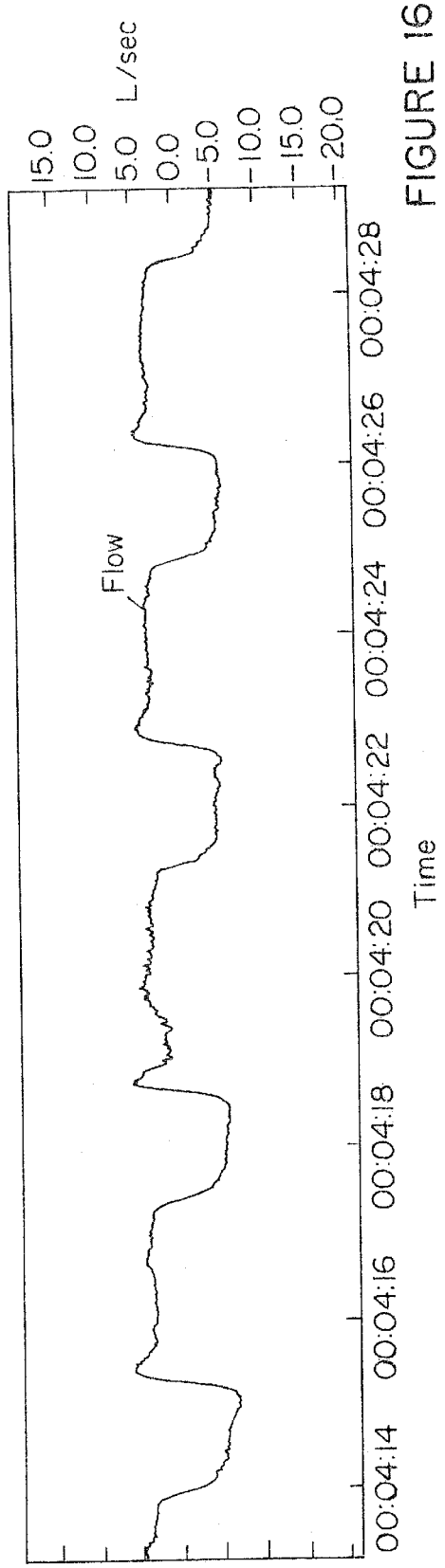
FIGS. 16D–16F graphically illustrate the uncalibrated flow, effort and comparative signals used in FIGS. 16A–16C after the administration of a bronchodilator.
Figure 16E:
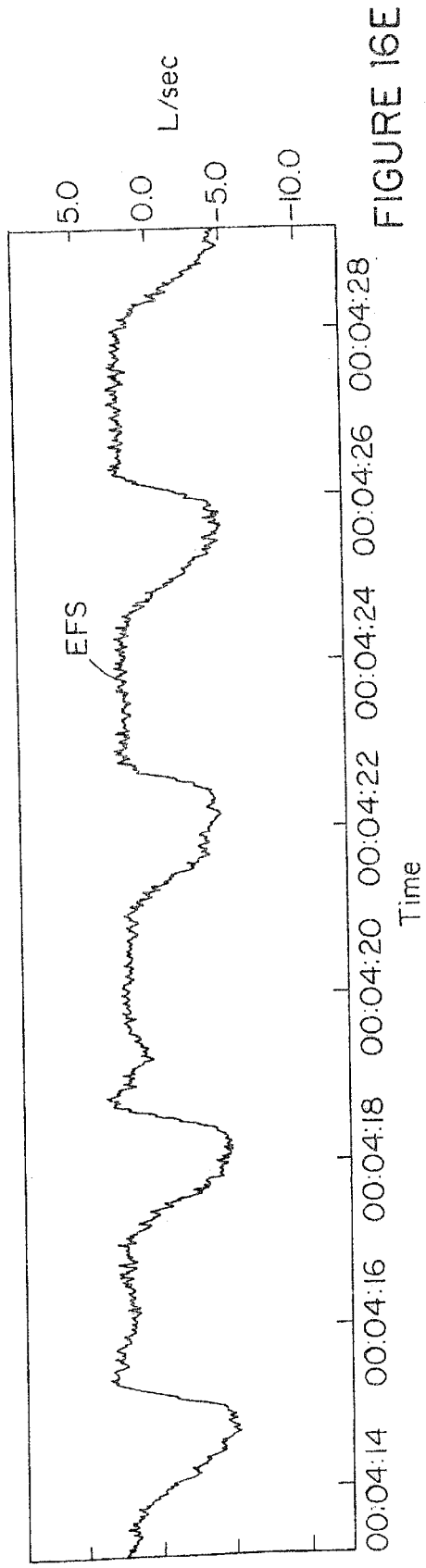
Figure 16F:
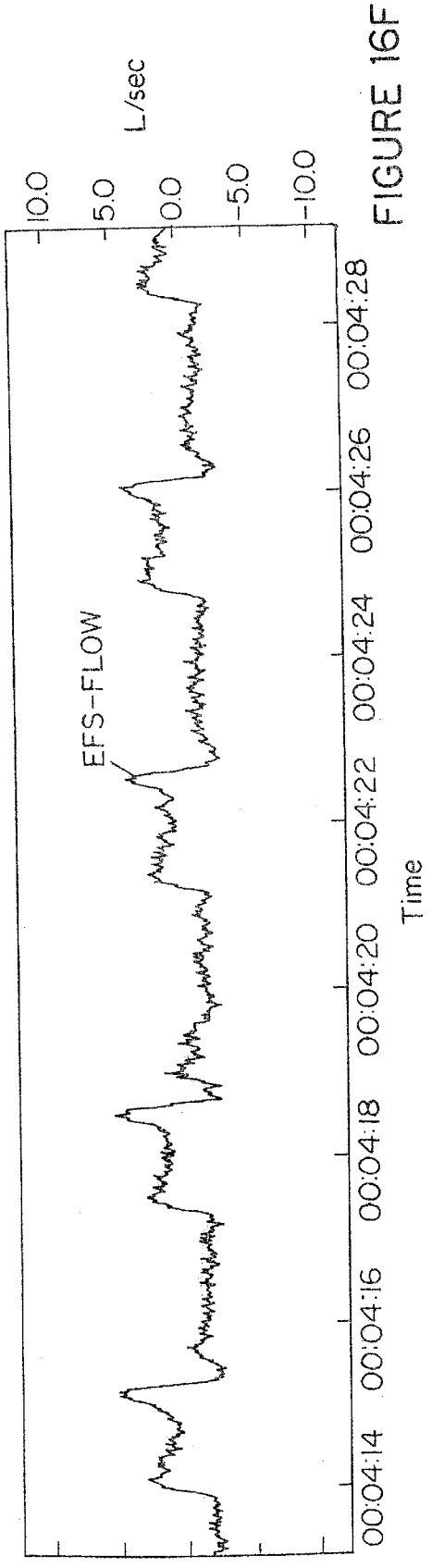

Referring to FIGS. 14A–14J and 15A–15H, examples of changes to the respiratory function during hyperventilation are illustrated. Hyperventilation is an increase in the rate of moving volume with respect to time or increased respiratory frequency and tidal volume product. It can manifest itself in the form of hyperpnea, where individuals take deeper breaths which correlates with increased tidal volume, tachypnea shown in FIGS. 15E–15H which is an increased rate, without increased tidal volume or some combination of hyperpnea and tachypnea as in the examples illustrated in 14F–14J. With hyperventilation, there is an increase in the magnitude and phase difference between external and nasal flow, but the differences are minor in comparison to an obstruction as illustrated in FIGS. 14A–14J. This suggests that the increase in the amplitude of the composite waveform as shown in FIG. 14I, is principally the result of gas compression and airway resistance in the airway, rather than a simple effect of respiratory drive. In fact, an increase in respiratory frequency alone, without a change in tidal volume, results in negligible effect on the composite waveform, as shown in FIGS. 15A–15H. Therefore, airway obstruction can be differentiated from increased respiratory drive and ventilation, without obstruction, using the methodology of the present invention.

Referring to FIGS. 12K–12P the external sensor signal is normalized to nasal flow for the purposes of calibration. In contrast, referring to FIGS. 16A–16F the external sensor is used without normalization to nasal flow. The results, in terms of the composite waveforms that results from the subtraction in the time domain between the external and the nasal flow signal, are similar with and without normalization for the purposes of calibration. An airway obstruction is apparent as is the response to bronchodilation. Thus, the methodology of the present invention has a further advantage as a system that incorporates a direct measure of phase differences, i.e., the use of any external sensor with high frequency response compared with any measure of true flow (for example, pneumotachography, breath sounds), can give meaningful results since the phase differences still persist. This allows some measure of airway obstruction with a number of sensors with or without conventional calibration.

The importance of comparing the external and flow signals in the same time domain is germane to the measurement of impedance during exercise or hyperventilation since phase mismatch is relevant. In the horse for example, inertance (the kinetic energy for acceleration of flow) is a major component of impedance (the ratio of driving pressure to flow) during exercise, and the continuous waveform analysis of the present invention allows one to visualize the phase delay during exercise and hyperventilation that in part reflects inertance. This appears as a very early spike in the composite waveform. Without a comparison of external and nasal flow signals in the same time domain, transient phenomena of gas compression or inertance cannot be visualized or analyzed. A measure of inertance is important as there are many obstructive or anatomical disorders or extrinsic devices that impose additional inertance on the respiratory system, altering lung function. During exercise, respiratory drive and ventilation are matched, but there is still the presence of inertance, reflected in a slight growing phase delay and differences in amplitude between the external and nasal flow signals, resulting in early spikes in the composite waveform, which may have diagnostic value.

In the instance where there is an increase in functional residual capacity (FRC) or residual volume (for example, air trapping during asthma or chronic obstructive pulmonary disease, emphysema, pneumothorax, positive end-expiratory pressure during ventilation), the subject's respiratory drive will be stimulated in most cases and respiratory drive to ventilation ratio will increase. However, in cases where respiratory drive does not increase to a significant extent due to physical limitations of the subject (for example, diaphragmatic muscle fatigue, weak muscles), a phase lag may persist between external and true flow and the composite and overlapping waveforms will reveal evidence of compressed gas in the thorax. The present invention may thus offer the advantage of detecting changes in FRC in instances where it was not possible to detect using prior art methodologies.

Figure 17:
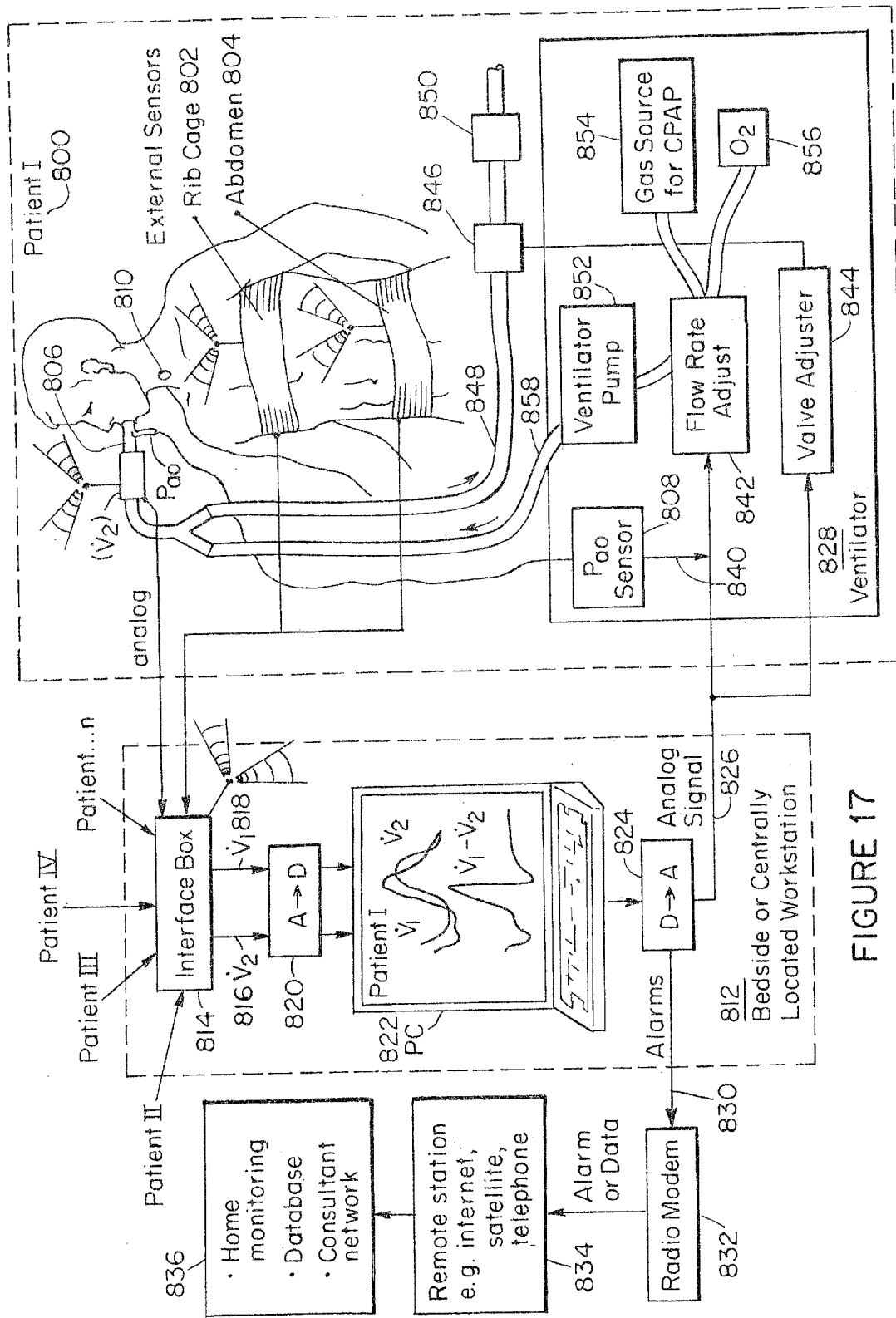
FIG. 17 is a schematic diagram of a monitoring system for a patient incorporating the method for measuring respiratory function in accordance with the present invention.
Figure 18:
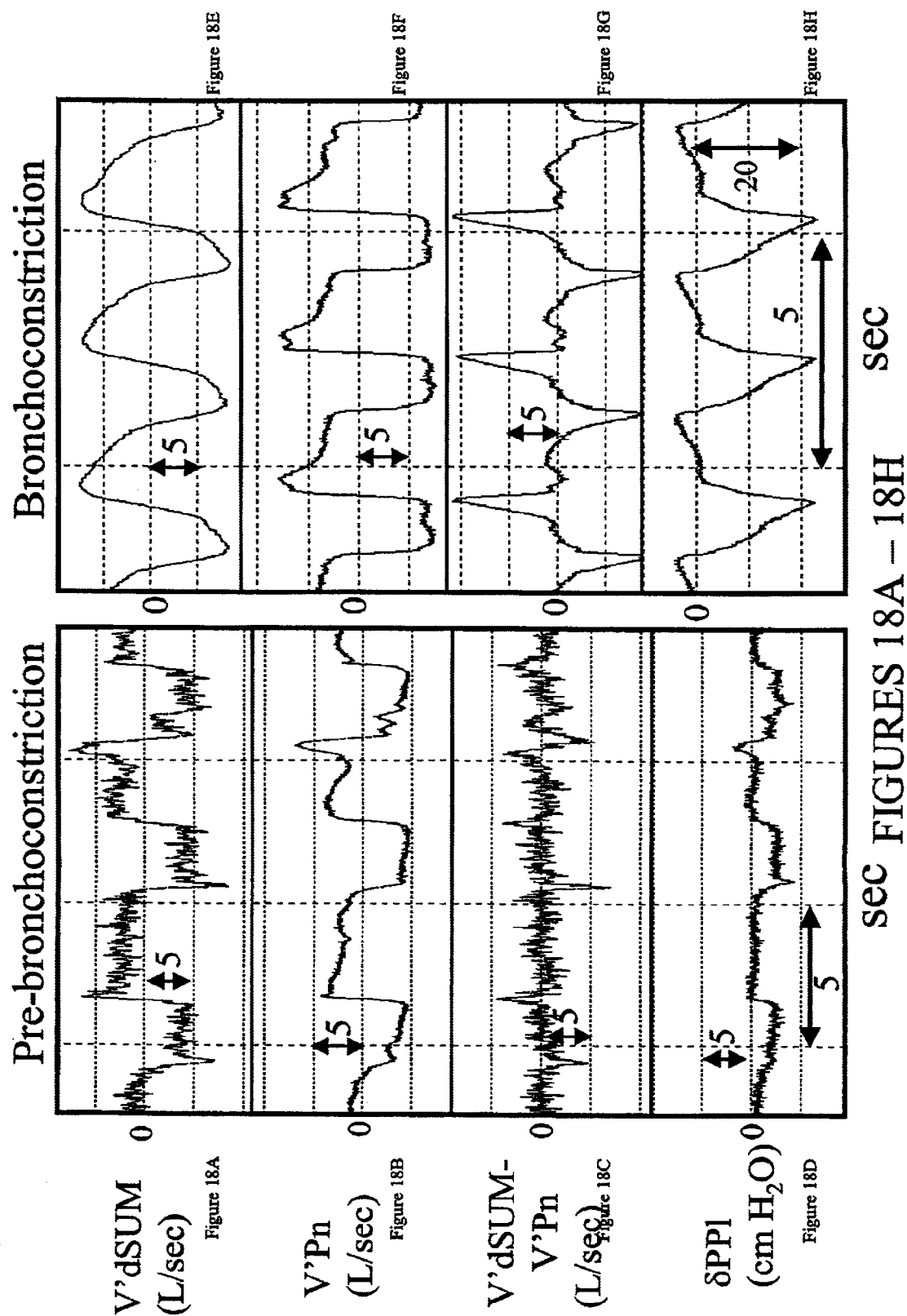
FIGS. 18A–18H graphically illustrate the summed and differential flow signal, the pneumotachographic flow, the waveforms created by the difference of the flow signals and changes in transpulmonary pressure compared to time for a pre-bronchoconstriction (baseline) and bronchoconstriction condition or administration of histamine aerosol.
Figure 19:
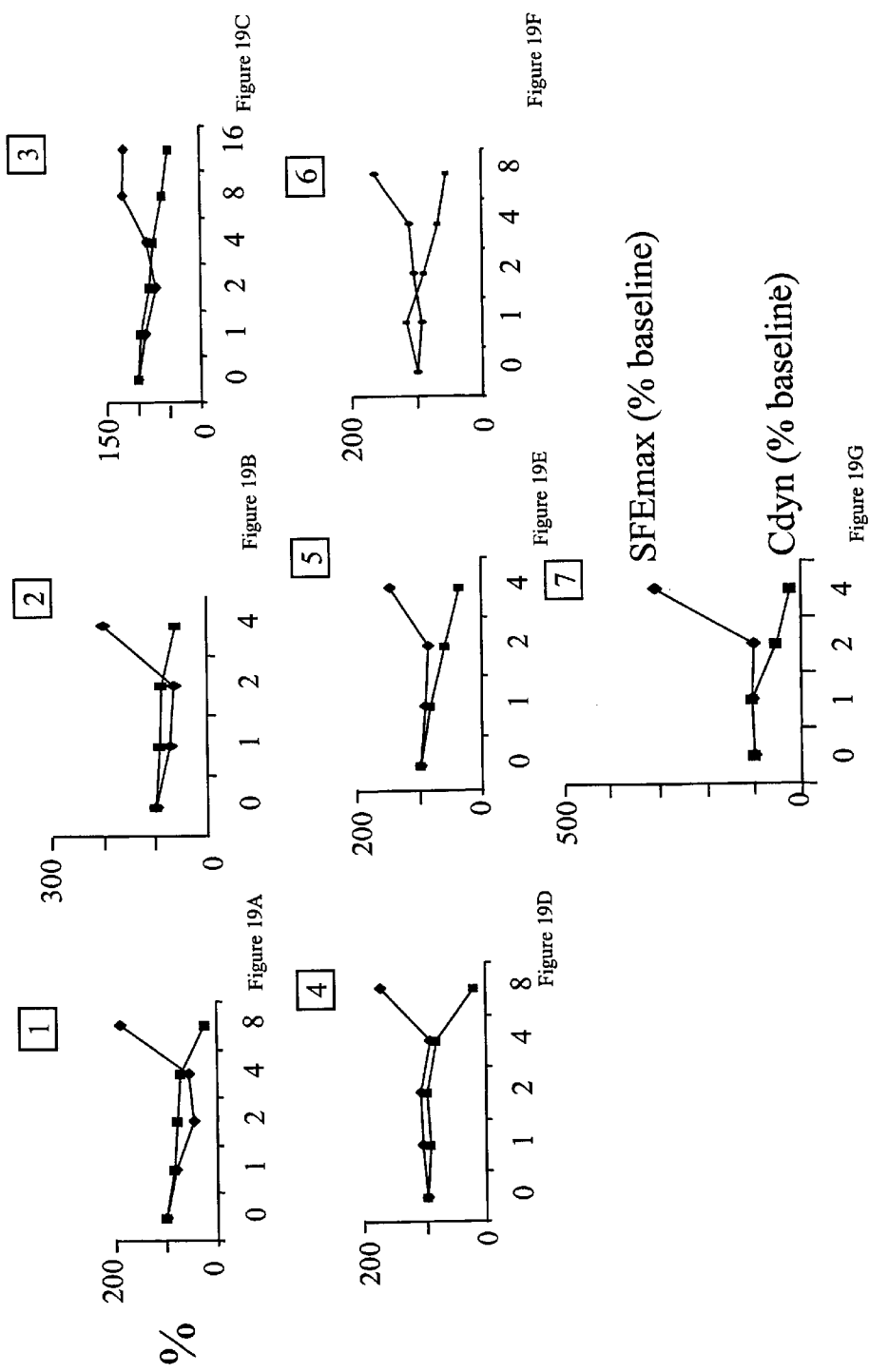
FIGS. 19A–19G graphically illustrate the response of seven subjects to a histamine aerosol challenge.

Referring to FIG. 17, a schematic diagram of a monitoring system for a human patient incorporating the method for measuring respiratory function in accordance with the present invention is illustrated. Humans breathe through their mouth and nose while some animals such as horses are solely nasal breathers, which simplifies flow collection and necessitates a different face mask for each category of subject. Humans voluntarily change breathing patterns. In animals data must be collected during tidal breathing or during physical pharmacological provocation to change the breathing pattern. Further, animals are quadrupeds and body posture in animals is not likely to change as drastically as in sitting or in the supine posture in humans. Animals in some cases have much greater abdominal contribution versus a rib or chest contribution, therefore signals emanating from the abdomen may be useful to compare with flow. A signal collected from the abdomen in horses represents a total effort required for breathing and reflects diaphragmatic movement and elastic recoil. In humans, data collected from the abdomen and rib may be similar or one signal may predominate over the other. The human patient, patient I 800, has external sensors to measure effort applied to the rib cage 802 and abdomen 804. The patient I 800 is also equipped with an endotracheal tube 806 or other patient and ventilator interface such as a continuous positive airway pressure (CPAP) mask. The airway flow of the patient is measured by a sensor 808 positioned at the airway opening such as a pneumotachograph that is coupled to the endotracheal tube 806. The sensor 808 may also be integral with the CPAP mask. In the alternative, a breath sound sensor 810, may be used to record sound as a surrogate for a measure of flow at the airway opening. This is another unobtrusive method to measure airway flow. Sound measured in decibels at a prescribed frequency versus time resembles flow. Since the output variables of interest for the present invention are principally kinetic (phase related), any measure of flow may be used such as sound, with post-hoc calibration or no calibration. Sound could be recorded using a small microphone in contact with the skin surface overlaying the trachea, lung or any segment of the respiratory system or by placing a directional microphone in the stream of air flow. Appropriate amplification, analog to digital conversion and waveform production is required for comparison with effort.

The signals indicative of effort as measured by, for example RIP bands at the rib cage 802 and abdomen 804, and the signal indicative of airflow form inputs into a bedside or centrally located workstation 812, in particular into an interface box 814 of the workstation. The interface box 814 may receive data indicative of effort and airflow from a plurality of patients whose respiration is being controlled from the bedside or centrally located workstation 812. The interface box, upon receiving the effort and flow signals from the patient then amplifies and transmits the signals. The outputs 816, 818 of the interface box then form inputs into an analog to digital converter 820. Processing of the effort and flow signals then occurs in the processor/display 822 in accordance with the present invention as described hereinbefore. Essentially a comparison of the effort and flow signals is performed by either overlapping the signals and studying the waveform differences visually or by generating a composite waveform indicative of the analog or digital point-by-point subtraction of the flow signal from the effort signal. The displayed overlapped and composite waveforms provide for efficient monitoring of the respiratory function by a health care provider as they need only to visually monitor the state of the respiratory function of the patient by either inspecting the overlapped or composite waveform or a combination of both.

The output of the processor/display 822 is then converted to an analog signal in a digital to analog converter 824 which supplies an analog signal 826 to a ventilator 828 or an alarm signal 830 via a radio modem 832 to a remote station 834. The remote station may be coupled to a network 836 which may be used for home monitoring of a patient, to a database system for storing of data and any post-acquisition analysis or trending, or to a network used by consultants also for further analytical processing.

The analog signal 826 that is outputted from the bedside or centrally located workstation 812 incorporating the system to measure respiratory function, in conjunction with the output 840 of the airflow sensor 808, form inputs to a flow rate adjuster 842 of the ventilator 828. The analog signal also forms an input into a ventilator valve adjuster 844 which in turn adjusts an exhalation valve 846 located on the exhalation segment 848 of the ventilator tubing. An exhalation flowmeter or volume sensor 850 is located downstream of the exhalation valve. The exhalation flowmeter 850 provides a check of the ventilation system against system leaks by checking if the amount of gas inputted by the ventilator is equivalent to the amount exhaled. The analog signal 826 indicative of the difference between the effort and airflow signal affects the CPAP flow rate and the resistance of the exhalation valve 846 to increase or decrease CPAP or change the oxygen percentage supplied to the patient requiring assisted ventilation. Thus, the ventilator pump 852 provides, using the continuous fresh gas source for CPAP 854 and an oxygen source 856, the required amount of oxygen to the patient via the inhalation segment 858 of the ventilation tubing.

The present invention lends itself to many applications. It can be used as a treadmill exercise monitoring system which requires hard wiring of the subject. Alternatively, a remote telemetric system can use radio waves to transmit effort-flow data to a workstation for real-time monitoring, display, data recording or processing. This application during an exercise regiment pertains to both animals and humans. The advantage of the present invention effort-flow system is the lack of obtrusiveness and allowing the subject to adopt natural body posture for exercise and sports. For example, in racehorses, body posture and breathing coordination, and head-neck angle are critical in optimizing respiratory and hence athletic performance.

A second application of the present invention is continuous or intermittent home or hospital monitoring for adults, children, infants and animal subjects as illustrated in FIG. 17. For example, patients on ventilators who require CPAP, assisted ventilation or synchronized/spontaneous intermittent mandatory ventilation SIMV, where effort is involved can use the present invention. Further, persons at home with severe respiratory disease and/or episodic disease which requires continuous or intermittent monitoring and alarm feedback for conditions such as emphysema, asthma, COPD, cystic fibrosis etc. The apparatus of the present invention may be tied in with an oxygen delivery system. The present invention provides a good effort to flow indication which can be correlated to the demand for oxygen thus making it attractive to tie the present invention to an oxygen delivery system. Further, an alarm system, utilizing preset thresholds and criteria can be optionally incorporated into the present invention. In patients on ventilators, inspiratory pressures are monitored and the present invention may allow monitoring of expiratory effort which is a good reflection of small airway flow limitations during ventilation. In patients with dynamic hyperinflation and growing FRC, the present invention may detect increased gas compression without change or before worsening airway obstruction, for example, in emphysema, asthma or COPD.

The present invention also provides a test to replace the peak-flow meter since the effort-flow kinetics during forced maneuvers requires a maximum or submaximum expulsion of air. Many severely effected patients cannot perform maximal forced maneuvers due to chest wall disease or dyspnea. An example of the value of the present invention in this regard is in the setting of a pneumothorax which occurs naturally or subsequent to surgery that is invasive to the lung and chest wall; the present invention compliments blood gas analysis, imaging, radiology and can cut costs of these procedures.

A bedside system with RIP or other bands, pneumotachograph, transducers, preamplifiers and simple liquid crystal displays (LCD) provides specific hospital needs. This introduces a greater degree of hardware uniqueness since all electrical components are housed in one unit and connected together on a circuit board.

The system of the present invention to measure respiratory function can use optoelectronic plethysmography to measure the signal indicative of change in lung volume. An optoelectronic plethysmography system analyzes the movement of a plurality of retro-reflective markers using television cameras connected to an automatic motion analyzer. The plurality of markers are simultaneously visible to at least two television cameras so that their three-dimensional positions and displacements can be constructed using stereo-photogrammetric methods. The markers can be placed in order to define at least three chest wall regions, for example, upper thorax, lower thorax and abdomen. An optoelectronic plethysmograph apparatus which can be used in a preferred embodiment of the present invention system to measure respiratory function is described in an article by A. Aliverti et al., entitled "Optoelectronic Plethysmography in Intensive Care Patients" published in the Am J Respir Crit Care Med, 2000 May, 161(5): 1546–52, the entire teachings of which are incorporated herein by reference. With respect to the system to measure respiratory function in accordance with the present invention, the signals representative of the movement of the upper thorax and the abdomen can be summed to result in a signal indicative of the change in lung volume or effort.

In yet another preferred embodiment, the system to measure respiratory function includes the use of a fiber optic respiratory plethysmograph such as one described in an article by C. Davis et al., entitled "A New Sensor for Monitoring Chest Wall Motion During High Frequency Oscillatory Ventilation," published in Med Eng Phys, 1999 Nov, 21(9): 619–23. The entire teachings of which are incorporated herein by reference. The fiber optic respiratory plethysmograph uses the chest and abdomen bands. These bands are composed of fiber optic material wherein bending movements due to change in chest or abdominal curvature results in macrobending losses of any light transmitted through the fiber which are proportional to the chest or abdominal perimeter.

FIGS. 18A–18H graphically illustrate waveforms derived from respiratory inductance plethysmography (RIP) and pneumotachography in a normal horse showing the effects of histamine induced bronchoconstriction of horses. None of the horses reacted adversely to placement of the inductance bands, either before or after sedation with xylazine. Histamine aerosols altered the waveforms of flow derived from Respitrace® V'dSUM in relation to pneumotach V'pn, in that the peak V'dSUM increased in relation to V'pn during the early portion of expiration, resulting in large increases in the waveform derived from their subtraction (V'dSUM–V'pn). The waveforms are derived from a baseline and post administration of histamine aerosol at a dose of approximately 4 mg/ml that evoked a clinical response.

FIGS. 19A–19G graphically illustrate histamine aerosol induced changes in flowmetric variable SFEmax compared to dynamic compliance $C_{dyn}$ expressed as a percentage of a baseline in seven healthy horses. The flowmetric variables, for example, peak during exhalation (SFEmax), peak during inhalation (SFImax) and integral of the subtracted waveform during the first 25% of exhaled and inhaled volume (SFEint and SFIint) are altered in relation to histamine dose. Seven horses given histamine aerosol responded with a decrease in $C_{dyn}$, and increases in pulmonary resistance ($R_L$) and transpulmonary pressure (δPplmax). In the seven horses, SFEmax increased with increased histamine dose. In six of the seven horses, there was an increase in SFEint, but in one horse with a tachypneic response, SFEint decreased at the highest histamine dose, after initially increasing as in the other horses. There were highly inconsistent changes observed for SFImax or SFIint, with increases and decreases as a result of histamine exposure.

Figure 20:
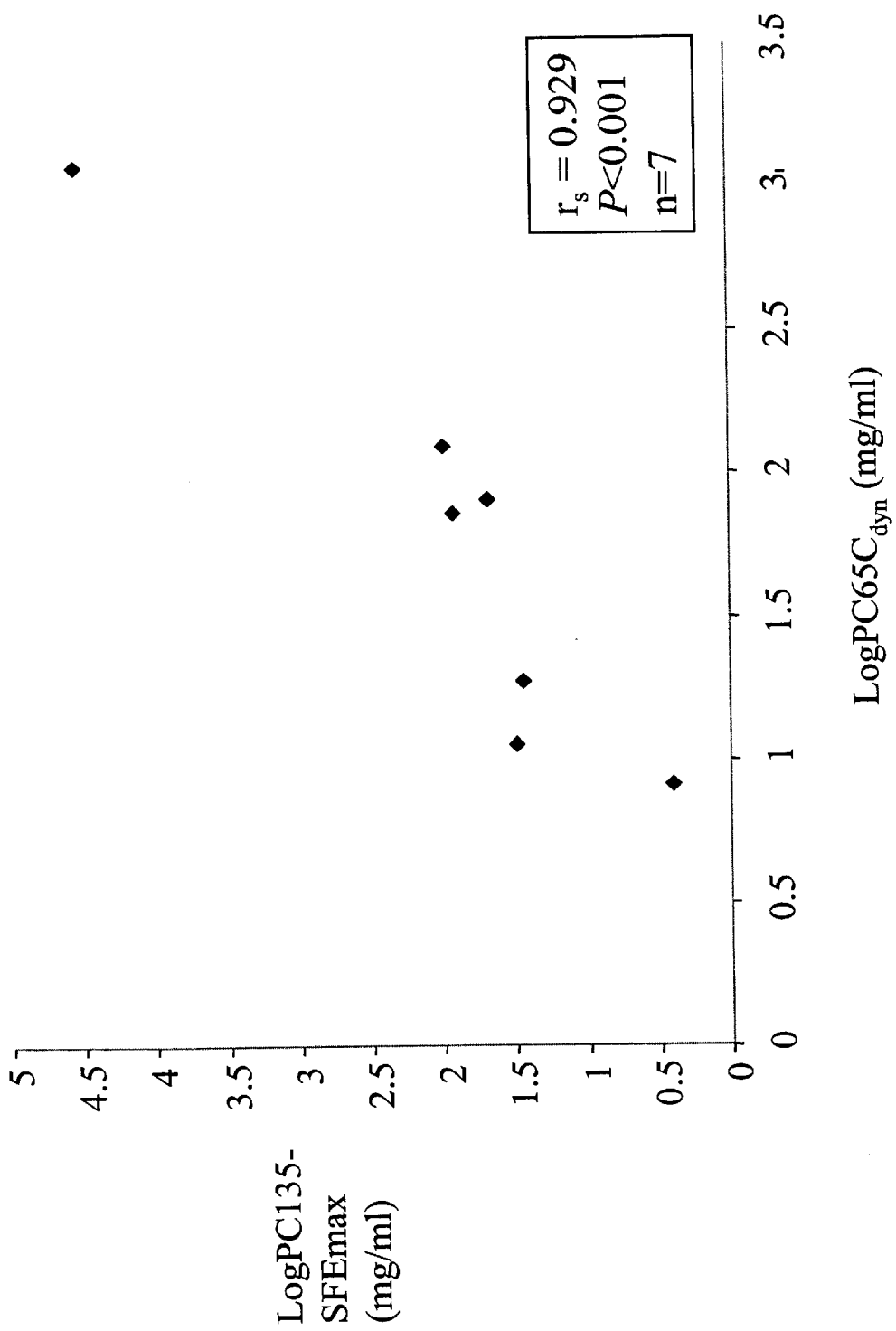
FIG. 20 graphically illustrates the change in peak difference during exhalation ($SFE_{MAX}$) with the highest dose of histamine.

FIG. 20 graphically illustrates a correlation between the provocative dose of histamine aerosol that evoked a 35% increase in the flowmetric test variable with the dose that caused a 35% decrease in dynamic compliance ($C_{dyn}$). Values for each variable is interpolated from their respective dose-response curves. There was a significant correlation in these tests of airway reactivity ($r_s$=0.93, P<0.001) between the logPC65Cdyn which is the log dose of histamine that decreased $C_{dyn}$ by 35% and logPC135SFEmax which is the log dose of histamine that increased SFEmax by 35%.

Figure 21:
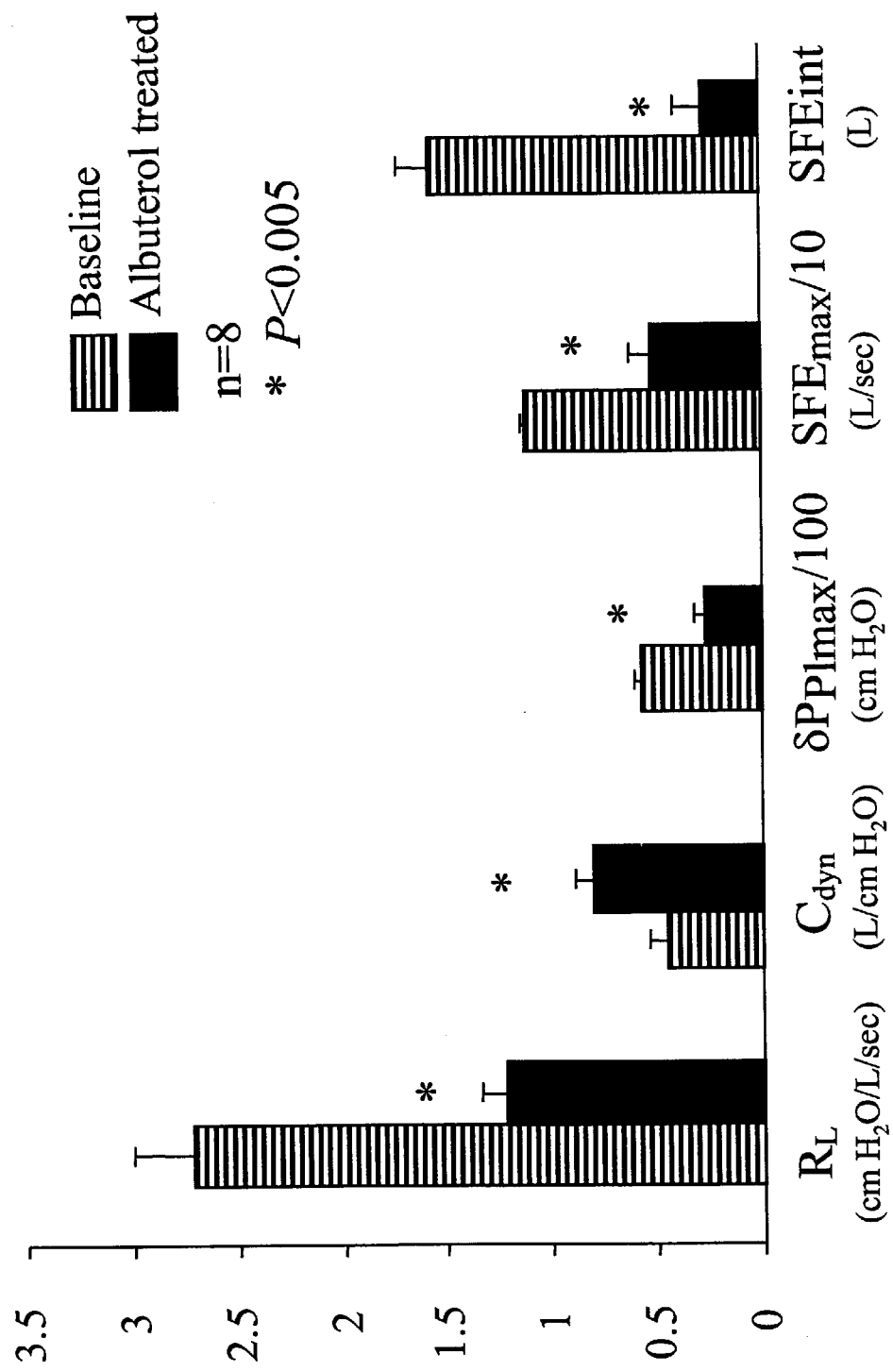
FIG. 21 graphically illustrates a comparison or effect of a baseline condition versus a bronchodilator (albuterol) treated condition for pulmonary resistance, dynamic compliance, changes in transpulmonary pressure, and peak difference during exhalation and inhalation.
Figures 22A, 22B, 22C, 22D, 22E, 22F, 22G, 22H:
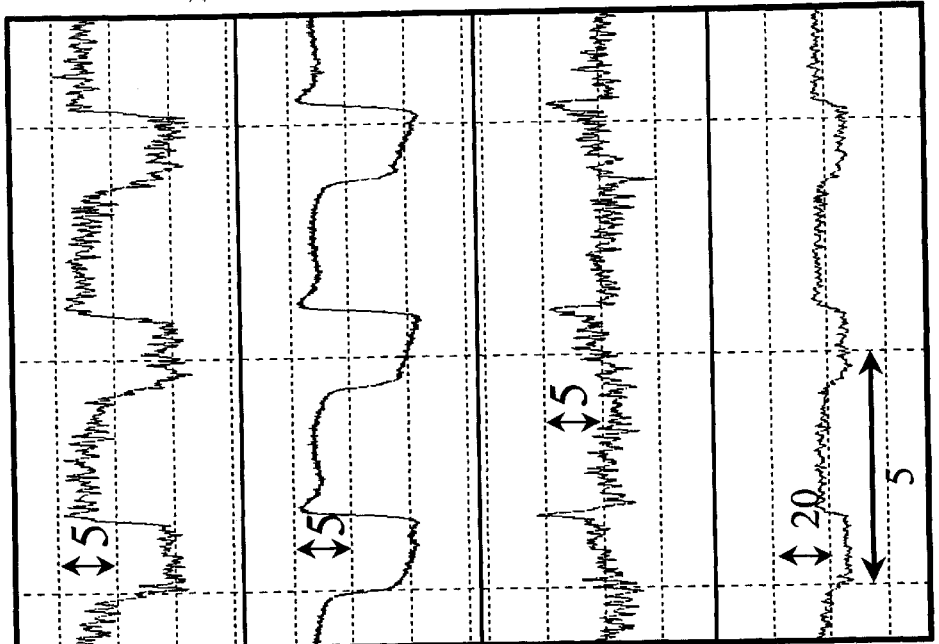
FIGS. 22A–22H graphically illustrate the waveforms of the summed and differentiated flow signals, the pneumotachographic flow, the waveforms created by the difference of the flow signals and changes in transpulmonary pressure as compared to time for a pre-bronchodilator and post-bronchodilator condition.

FIG. 21 graphically illustrates the effects of bronchodilators on conventional variables ($C_{dyn}$, $R_L$, $\delta P_{PL}$) and flowmetric variables (SFEmax, SFEint) measured using the system in accordance with a preferred embodiment of the present invention in horses with naturally occurring recurrent air obstruction, also known as 'heaves'. All subjects were exposed to a bronchodilator such as, for example, albuterol, pMDI, 450 μg. The administration of albuterol aerosol caused significant decreases in $R_L$, δPPlmax, and an increase in Cdyn within 5 minutes. Prior to bronchodilation, horses with heaves showed marked differences between V'dSUM and V'pn, particularly in the early portion of expiration.

FIGS. 22A–22H graphically illustrate waveforms derived from respiratory inductance plethysmography (RIP) and pneumotachography in a horse with naturally occurring recurrent airway obstruction before (baseline) and after treatment with a bronchodilator. The bronchodilator can be, for example, albuterol pMDI, 450 μg. The flow traces were derived from RIP (V'dSUM), pneumotach (V'pn) or their difference (V'dSUM–V'pn). The subtracted waveform is characterized by large positive expiratory spikes and smaller inspiratory spikes in the negative direction.

FIGS. 23A–23F graphically illustrate the correlations between conventional measures with flowmetric measures in accordance with preferred embodiment methods of the present invention in horses with naturally occurring recurrent airway obstruction before and after administration of a bronchodilator. The bronchodilator is, for example, albuterol, pMDI, 450 μg. Bronchodilation reversed the qualitative changes, accompanied by significant (P<0.005) decreases in SFEmax and SFEint. There are highly significant (P<0.005) correlations between the flowmetric variables and $R_L$ or δPplmax when pre and post bronchodilator values were compared. However, there is only a trend for the correlation between Cdyn and SFEint (r=−0.49, P=0.054) and no significant correlation between Cdyn with SFEmax (r=−0.38, P=0.14). Furthermore, there were no significant correlations between the flowmetric variables and tidal volume versus SFEmax: r=−0.3, P=0.25; versus SFEint: r=0.1, P=0.71 or frequency versus SFEmax: r=0.26, P=0.32; versus SFEint: r=0.02, P=0.95. Bronchodilation did not significantly alter the inspiratory flowmetric variables SFImax of SFIint. None of the inspiratory flowmetric variables correlated with any of the conventional variables, with the exception that SFImax showed a trend toward correlation with δPplmax (r=0.47, P=0.067) and $R_L$ (r=0.46, P=0.074).

Figure 24:
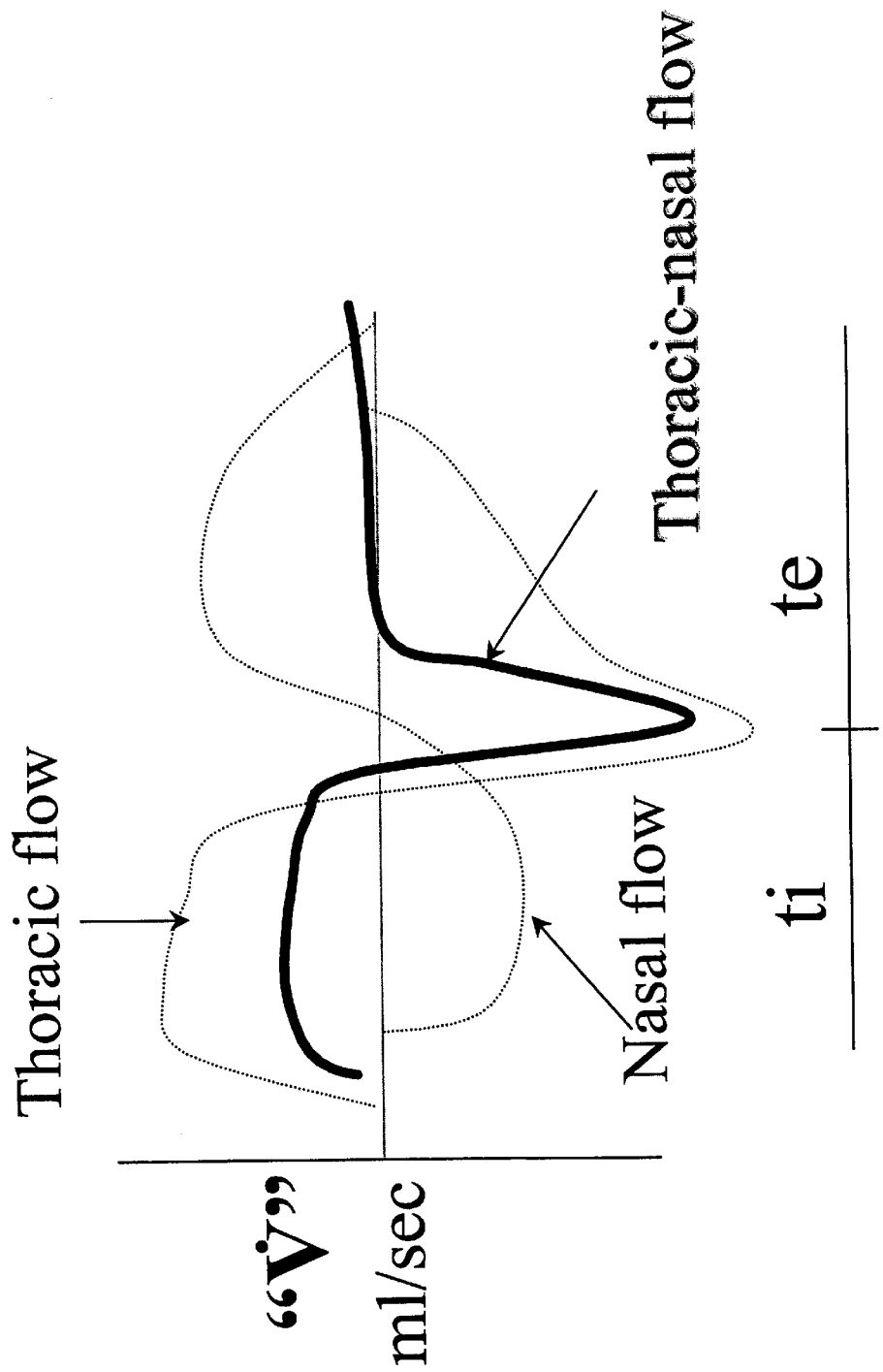
FIG. 24 graphically illustrates the difference between the plethysmographic measurement indicative of external flow and the uncompressed airflow or nasal flow in accordance with a preferred embodiment of the present invention.

FIG. 24 graphically reiterates the difference between the signal indicative of change in lung volume and the uncompressed airflow signal. The difference between these two signals represented by thoracic flow minus nasal flow reflects the severity of a lower airway obstruction.

Figure 25:
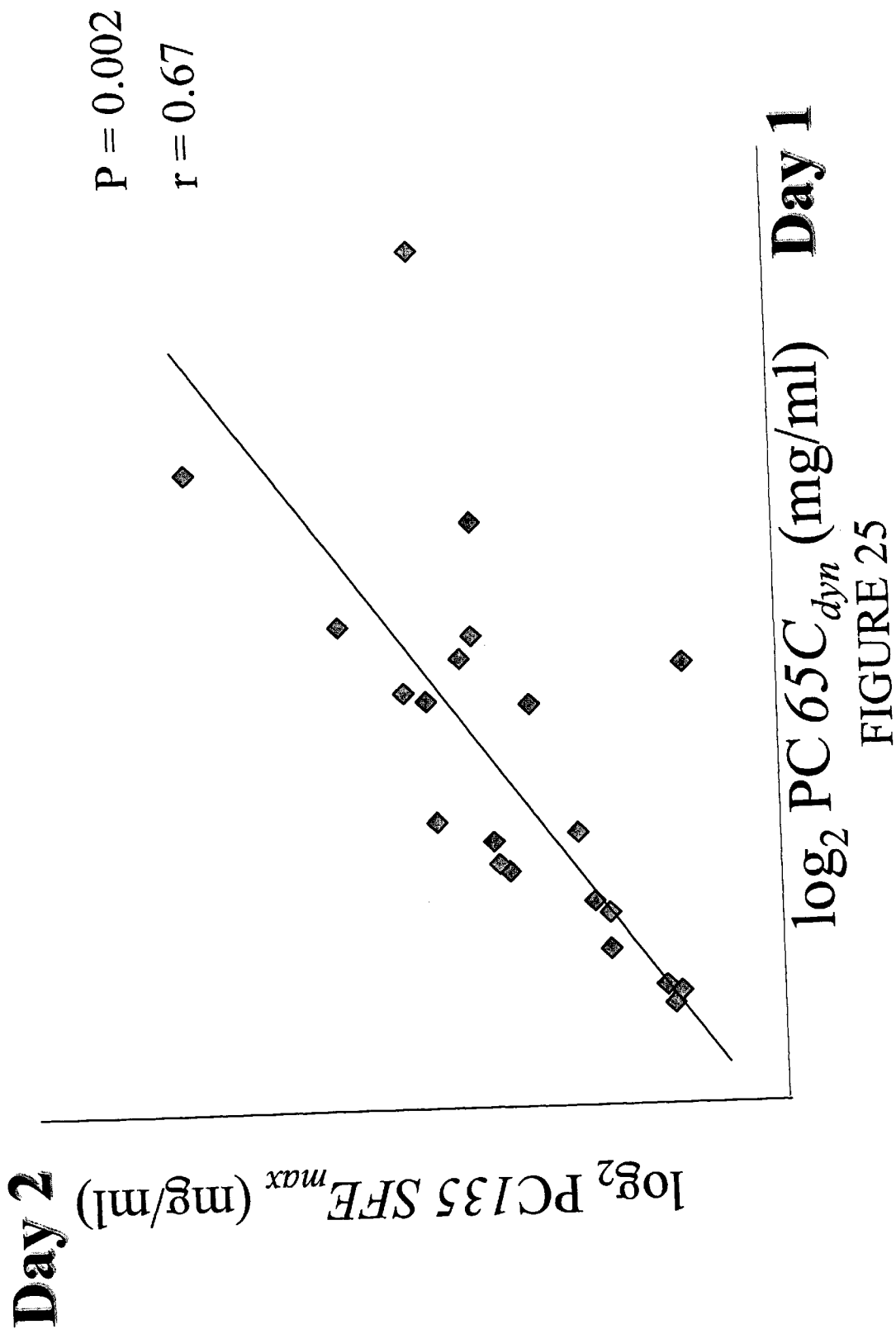
FIG. 25 graphically illustrates the repeatability of the measurement of airway reactivity in 21 horses (subjects) using the flowmetric system in accordance with a preferred embodiment of the present invention.

FIG. 25 graphically illustrates the repeatability of the measurement of airway reactivity using a preferred embodiment of the system to measure respiratory function in accordance with the present invention in a plurality of subjects, in particular, 21 horses. The outcome variable is the histamine dose that increased the peak difference in the signal indicative of change in lung volume and the signal indicative of airflow during expiration to 150% baseline or a 50% increase. The flowmetric variable is repeatable to a high level, with all horses that were hyperreactive were reactive on both test times, Day 1 and Day 2. It should be noted that Day 2 was spaced apart from Day 1 by a duration, for example, of three weeks. The repeatability is greater in more reactive animals. Thus, the measurement and the condition are stable over the short period of measurements. The measurements were repeated one year later and identical results were obtained.

There currently exists no acceptable way to perform pulmonary function tests in veterinary clinics. The unacceptable aspects of the currently available tests include invasive devices, for example, esophageal balloon catheters, insertion of pleural pressure catheters or needles, requirement for anesthesia and intubation, long duration of measurements, poor sensitivity or repeatability of noninvasive tests, for example, pneumotachography, i.e., measurement of nasal flow alone, the intolerance of certain species to complete enclosure in a plethysmograph while conscious, the interference of the nasal passages with measurements of lower airway status, for example, by oscillatory mechanics, and the interrupter method of measuring resistance. The result is a complete absence of pulmonary function testing in veterinary hospitals, and the lack of a sub-specialty in veterinary pulmonology, despite subspecialties in most other areas, for example, but not limited to cardiology, dermatology, neurology, ophthalmology, emergency and critical care, nutrition, and pathology.

The embodiments described herein before are systems for measuring respiratory function that are better for either large animals and/or humans. There is also a need for diagnosing airway reactivity and related diseases in small animals, in particular conscious small animals.

The measurement of resistance in awake animals requires that the measurements are made during tidal breathing or during short occlusions tolerated by animals. Humans on the other hand can be coaxed into forced maneuvers, breath-holds, and controlled inspiratory or expiratory efforts against a closed shutter.

Another aspect of a system to measure respiratory function of some small mammals, in particular dogs, is that they frequently pant. Panting complicates measurements of lung function because it requires very fast sensors. Furthermore, limited information is obtained from flow signals alone from a panting animal. Flow signals need to be compared with the effort to generate them that is the driving pressure. On the other hand, there are advantages of panting to some measurement such as the glottis is usually open during panting in humans and animals, allowing measurement of airway events without interruption or obstruction from normal structures, and panting promotes the equilibration of alveolar and airway gas, for example, oxygen and carbon dioxide tensions, temperature, and humidity, with the gas in/around the facemask. The normal heating and humidification plus expulsion of carbon dioxide changes the gas composition of inhaled gas, confounding normal measurements of flow.

With respect to airflow resistance in humans, whole body plethysmography is still the gold standard to use. Alternatives include the airway interrupter method.

The interrupter method has not been evaluated in animals. This system measures alveolar pressure by short occlusions of flow, and measurement of pressure at the mouth or airway opening upon equilibration. Comparison of airway opening pressure (Pao) and the flow that preceded, provides the basis for measurement of pulmonary resistance (Pao/V'). The patient must not "react" to the occlusion by closure of the glottis, which is common, and there remain questions about how representative Pao is of alveolar pressure. Another method to measure resistance is the insertion of an esophageal balloon for measurement of pleural pressure, coupled with measurements of flow at the airway opening. This is not tolerated in small animals, but is a well-established method in horses.

Functional Residual Capacity (FRC) can be measured using steady state or rebreathing methods that employ a tracer gas which are poorly absorbed such as helium or nitrogen. The dilution of this tracer is measured during breathing. However, these systems require quiet breathing, and excellent mixing of the tracer gas with alveolar gas. If the subject does not take a deep breath, for example, the subject pants, there is poor mixing of the tracer gas with the volume of air (FRC) for which dilution is possible. These systems are also confounded when the subject has airway obstruction, which impedes the mixing of the tracer gas with the alveolar gas. FRC can also be estimated from X-rays, however this is an inaccurate method. A rapid plethysmographic method for measuring thoracic gas volume and a comparison with a nitrogen washout method for measuring function residual capacity in normal subjects i.e., is described by A. B. Dubois et al. in J Clin Invest 35:322–326, 1956, the entire teachings of which are incorporated herein by reference.

Figure 26A:
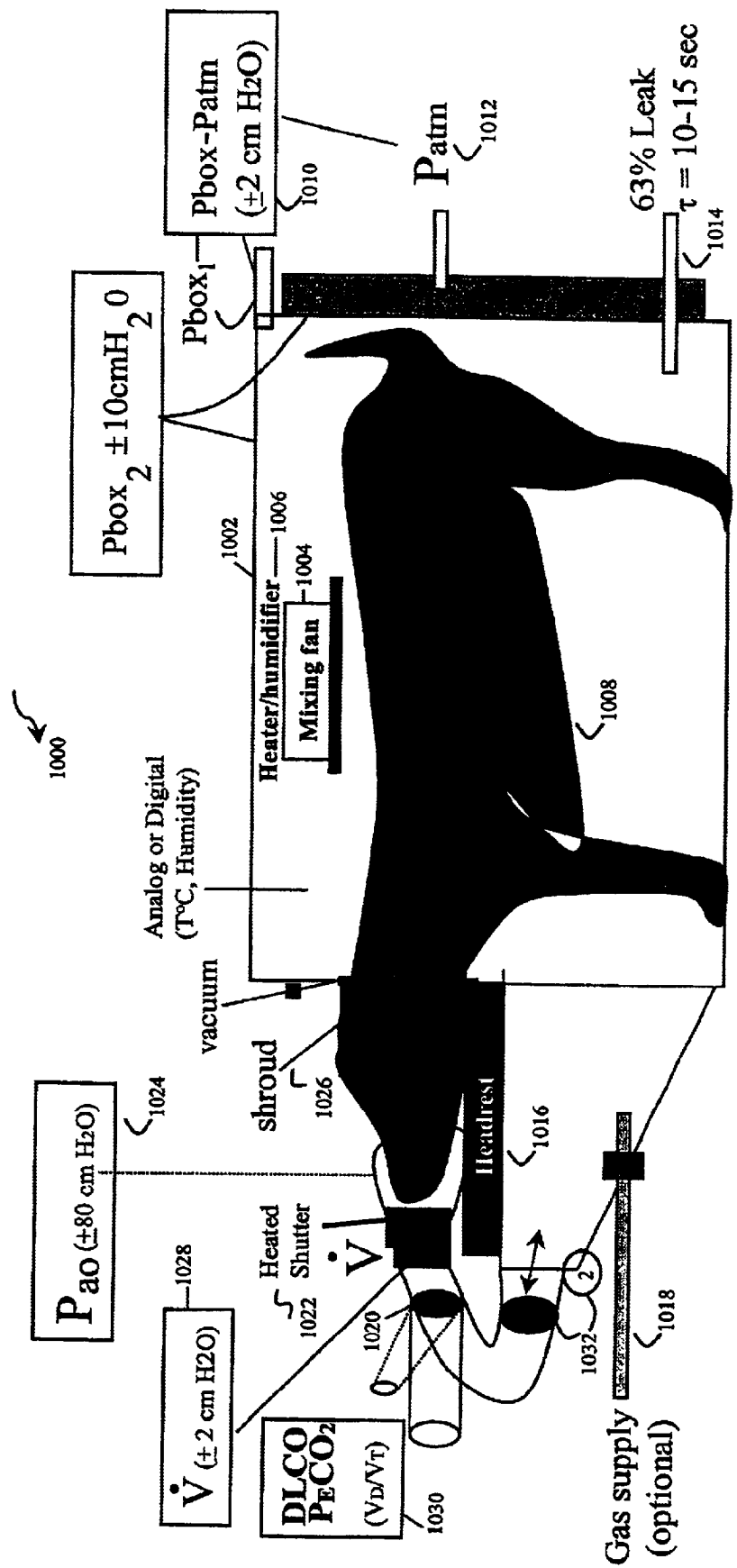
FIGS. 26A–26C are schematic diagrams of a preferred embodiment of the system for measuring respiratory function in conscious animals in accordance with the present invention.

FIG. 26A, is a schematic diagram of a preferred embodiment of the system for measuring respiratory function in conscious animals in accordance with the present invention. The system 1000 includes a plethysmograph 1002 which may be characterized as a constant volume plethysmograph wherein the subject positions their head outside the chamber but breathes into the chamber. This plethysmograph 1002 is distinguishable from a system for whole body plethysmographs in which the whole body is located within a single chamber but the subject's breath is vented to the outside. Other plethysmographs that are distinguishable from the system 1000 include a double chamber plethysmograph in which the subject's head is located in a different enclosure than the body, and a whole body barometric plethysmograph, in which the whole body is enclosed and breathing within a single chamber. The constant volume breath in, plethysmograph 1002 is particularly suited to small animals, for example, dogs. As discussed before, dogs exhibit panting which adversely affects measurements from other prior art systems. The plethysmograph 1002 has the advantage of maintaining the subject's glottis in the open position. Further, dogs are tractable if restrained by leash or voice communication or alternatively handling around the head. Dogs also tolerate face masks, unlike cats, for example.

The system 1000 to measure respiratory function allows the positioning of the head of the subject outside of the box and provides an environmental seal around the box, yet the subject breathes back into the chamber through a low resistance/inertance tube 1033. Panting is allowable and actually preferable for some measurements. The system 1000 can be used for flowmetric measurements such as measuring airway obstructions during inspiration and expiration. It further permits double chamber plethysmographic measurements without the large deadspace around the head of a subject. The use of a facemask 1035 provides access to other attachable devices for measuring gas exchange, for example, but is not limited to, diffusion capacity (DLCO) 1030, functional residual capacity (FRC), and dead space/tidal volume ratios and other pulmonary function variables. The system 1000 in accordance with the present invention gives actual measurements of airway resistance and FRC, unlike the estimations obtained from double chamber and whole body barometric plethysmography.

The chamber or box 1002 can be made in a variety of sizes or made adjustable in terms of volume with adjustable internal dimensions. Dogs in particular vary in size. If the volume of the animal is too small relative to that of the box, the sensitivity of the signal, i.e, the signal to noise ratio is lowered. For research purposes, where beagles, for example, are used, the size considerations are insignificant. However, in clinical applications such as the use of the system 1000 to measure respiratory function, dog subjects can range from 3 to 50 kg in weight requiring an adjustable size box to satisfy all sizes. A plurality of chambers may also be used if necessary. However, downstream devices from the box remain identical. In a preferred embodiment, the system 1000 of the present invention has the ability to switch hardware for data collection between boxes. This interchangeability of data collection hardware can be achieved by using universal connectors, and by transferring transducers between boxes, for example. In addition, a series of facemasks are necessary as well, and are found commercially in the field of anesthesia. A facemask with low dead-space is preferable. In accordance with a preferred embodiment, it is preferable to produce molds of different types of noses in the case of dogs, to provide an optimal fit.

Figure 26C:
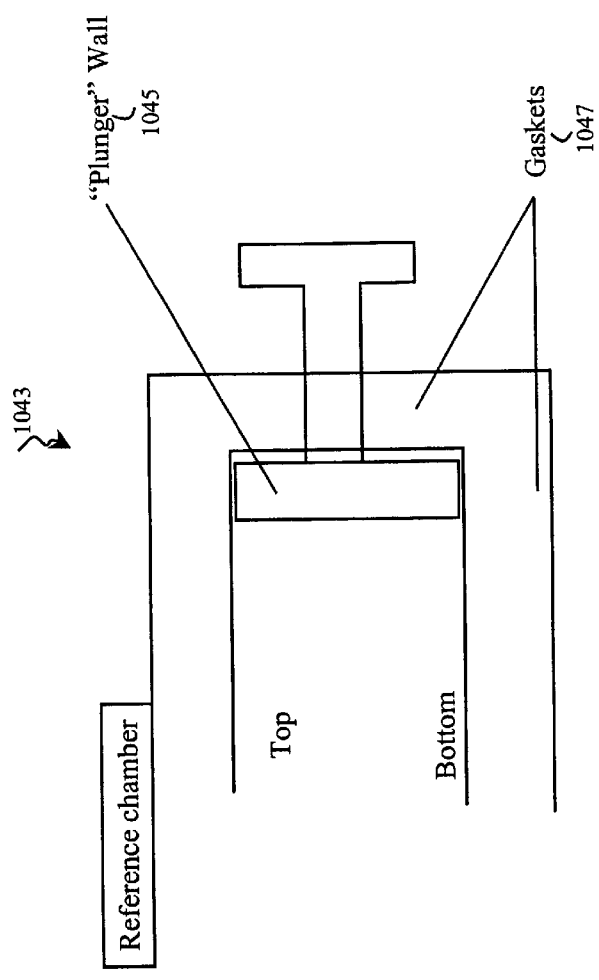

The volume adjustable aspect of each box is important to accommodate a range of size animals/humans that can be tested within each box. FIG. 26C illustrates a preferred embodiment of the chamber 1002 with a volume adjustment assembly 1045. The volume adjustment assembly 1045 can be a wall opposite the wall of the head seal that acts like a plunger device, reducing the volume of the box. The change in volume is achieved from the inward movement of the plunger but there remains an external wall for physical support of the box. The seal of the plunger, once in its new position, provides an environmental seal. An expandable gasket 1047 can be used to achieve the hermetic seal.

The subject length is premeasured before placement of the subject in the box, so that the plunger wall is preset. The premeasured volume aids in restraint and acclimation of the subject. It also permits calibration to be performed at this appropriate box volume, which is necessary. In a preferred embodiment, the box transducers are located on the top of the box preferably, which is an appropriate location due to the thermal volume of the main chamber better equilibrating with the reference chamber if the latter is located on the top.

In an alternative preferred embodiment, the volume adjustment wall 1045 could be porous, with large holes in it. In this embodiment, there is no expectation that the wall 1045 is sealed. Rather, it acts only as a mechanical assist to push the dog forward. To be space efficient any space-occupying devices such as non-compliant blocks of plexi-glass or wooden cubes are placed behind the volume adjustment door, prior to the outer door accessed by the user is shut. The non-porous volume adjustment or plunger wall allows for quick adjustments to box volume and avoids the possibility of that the main chamber acts like two distinct compartments in terms of the distribution of box pressure. In a preferred embodiment, the non-porous wall requires a siliconized gasket, and a gasket seal for the plunger pole itself as it rides through the stationary wall.

The chamber 1002 is small enough to be quickly heated, and therefore is more thermally stable than large whole body systems. A thermal sink for example, but not limited to a coil is present in the chamber 1002 in a preferred embodiment of the present invention. Thermal drifts are minimized by providing a shunt 1014 to the ambient environment. The time constant for the plethysmograph, system 1002 that buffers a thermal drift is preferably in the range of 10 to 15 seconds which provides approximately 63% of a leak to ambient. The environment in the chamber 1002 is controlled using a heater/humidifier 1006 and a mixing fan 1004. An analog or digital measurement provides a measure of the temperature and humidity in the chamber.

The system 1000 of the present invention permits serial sampling over the short-term or long-term as it is non-invasive, and measurements can be made quickly. Data acquisition is computer based, using computations that are well-established in the field of physiology. This increases acceptance of the system 1000 since this is not a surrogate measure of respiratory physiology requiring inordinate tests of validity.

The commercial market for this item includes veterinary hospitals that specialize in internal medicine, emergency and critical care, oncology, referral hospitals, biotechnology or pharmaceutical companies, or physiology laboratories. There are many applications for the study of respiratory system disease, whether upper or lower airway, parenchymal (lung tissue), or chest wall disease.

Measurements that are useful for assessing the respiratory system of subjects include measurement of diffusion capacity of carbon monoxide (DLCO), dead space to tidal volume ratio, and capnography. All these measurements can be made with the subject positioned in or out of the box. The facemask 1035 and a 3-way valve 1020 is needed at the airway opening. Attachment to appropriate gas sources 1018, and outlets to either atmosphere or gas collection bags is also needed. A specific advantage of coupling the head-out breath-in measurements and of functional residual capacity (FRC) with DLCO is the correction of DLCO. In general, the interpretation of all the pulmonary function tests are enhanced by knowledge of the others. The system 1000 of the present invention is capable of measuring these parameters in awake animals, in particularly dogs and small ruminants to provide important clinical and research information. In addition, this system serves as a basis for a comprehensive pulmonary diagnosis.

Figure 26B:
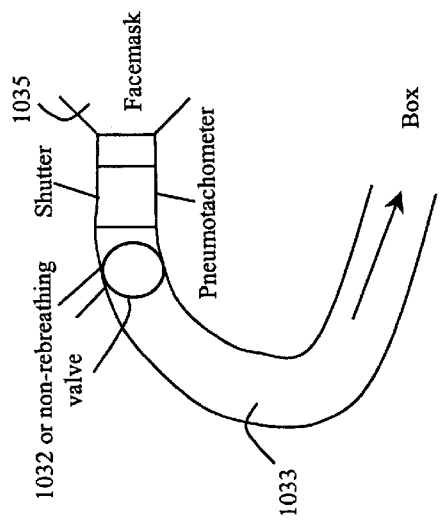

The chamber 1002 has multiple pressure transducers such as, for example, but not limited to an ambient pressure transducer Patm, a box low pressure differential pressure transducer $Pbox_1$ and a higher pressure differential pressure transducer $Pbox_2$. Both $Pbox_1$ and $Pbox_2$ are referenced to ambient. $Pbox_1$ is in the range of approximately ±2 cm $H_2O$ while $Pbox_2$ is in the range of approximately ±10 cm $H_2O$. A pressure transducer Pao 1024 is in the range of approximately 50 to 100 cm $H_2O$ and measures airway pressure. Further a pneumotach 1028 measures airflow V using a pressure transducer in the range of approximately ±2 cm $H_2O$. Airflows range widely depending on the size of the animal and disease state, but typical flows for large (40–50 kg)dogs are in the following ranges: peak expiratory flow approximately 800 mL/sec and peak inspiratory flow approximately 750 mL/sec. The types of pneumotach 1028 that may be used are, without limitation, for example, screen-type, Fleisch, ultrasonic and turbine pneumotach. A detailed view of the extension tube 1033 is provided in FIG. 26B.

Figure 28:
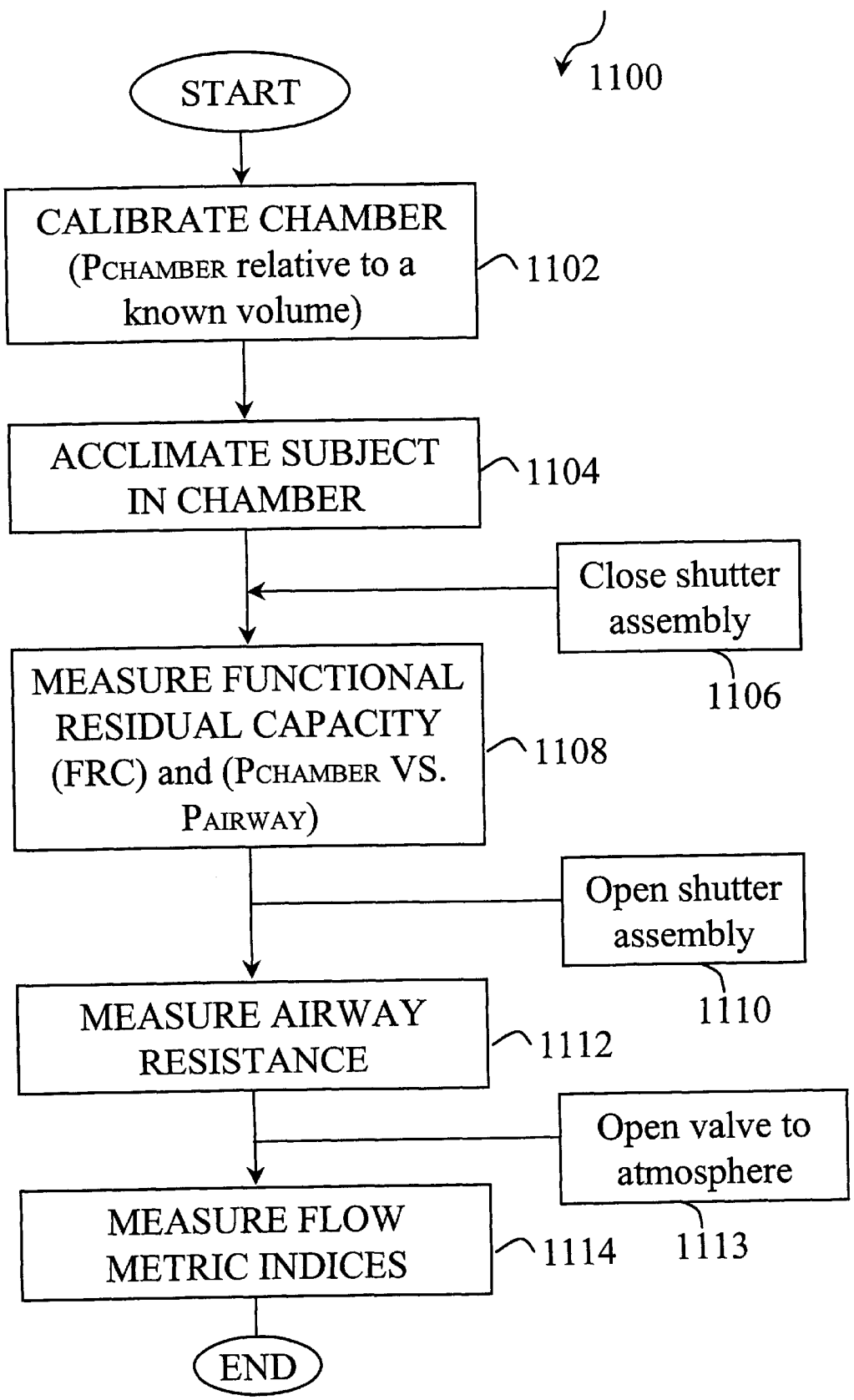
FIG. 28 is a flow chart illustrating a preferred embodiment of a method to measure lung function in conscious animals in accordance with the present invention.
Figure 29:
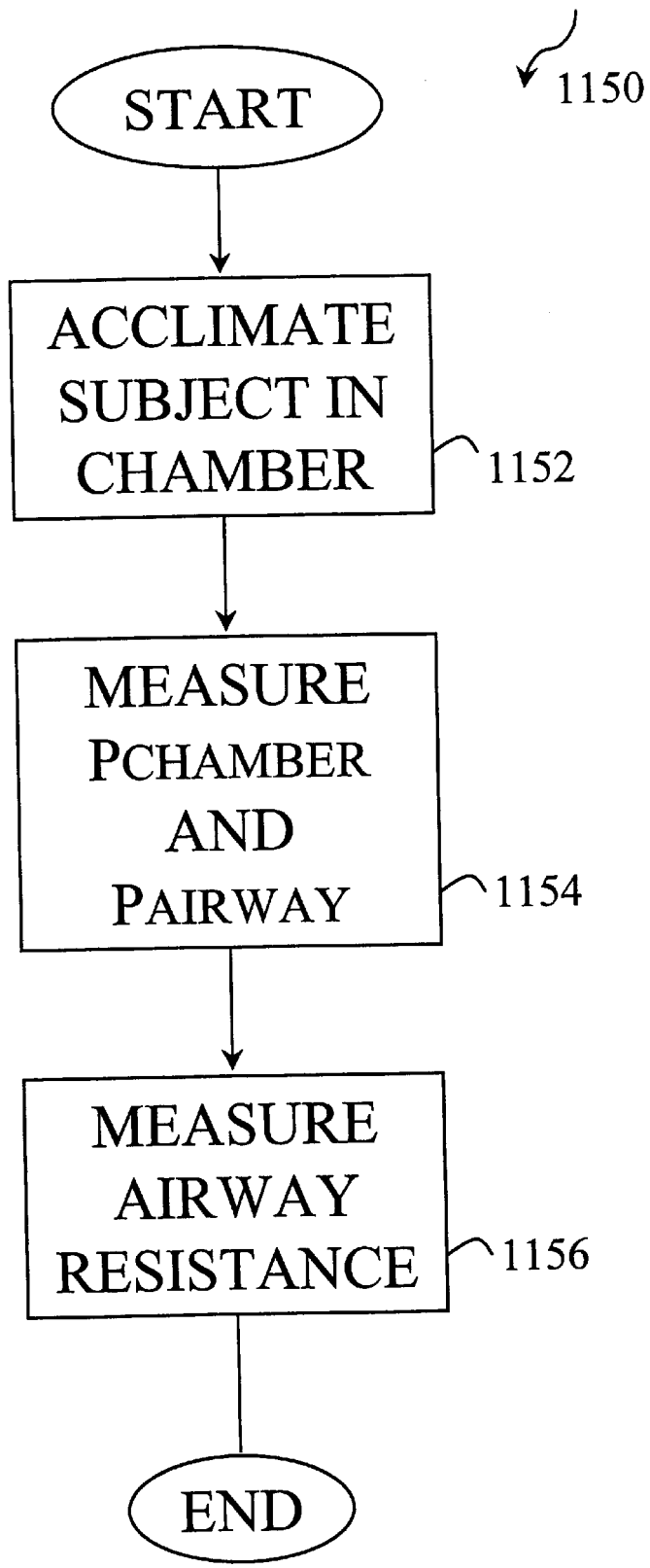
FIG. 29 is a flow chart illustrating another preferred embodiment of a method to measure lung function in conscious animals in accordance with the present invention.

FIGS. 28 and 29 are top-level flow charts illustrating preferred methods 1100, 1150 of measuring respiratory function in conscious animals in the system 1000 in accordance with the present invention. The methods 1100, 1150 start by the preparation of the box prior to placement of animal or human. An option of a preferred embodiment includes a duration to prewarm and/or pre-humidify the box. In another preferred embodiment, a prewarm or humidification of the box is not provided. Temperature, humidity, and barometric pressure in the box is monitored using digital or analog sensors. It should be noted that an alternative embodiment of the system design for anesthetized animals uses an endotracheal tube through the wall of the box. A shutter is attached to the external portion, and an extension tube is coupled back through a port in the wall of the box. This effectively allows breathing-back into the box, and the control of the movable shutter from the outside.

Per step 1102, the chamber is calibrated with the box sealed to atmosphere, the gains of amplifier (Pbox) and adjusted. The maximum voltage deflections expected during airway occlusions fall within an acceptable range, for example, +/−5 V. To produce these deflections, physiologic volumes expected during occlusion are used such as 0.25 ml/kg body weight.

Per step 1104, acclimation of the subject and thermal equilibration of the box is performed. The subject is placed in the box, standing with its head out through a vacuum sealed or latex/rubber shroud/seal to prevent air-leak. The subject can be restrained according to conventional methods. For example, the dog can be handled gently about the head, or a leash can be maintained around the neck. The dog is left in the box for up to five minutes to permit better equilibration of the box temperature.

The calibration of the box is performed with the subject being attached to the facemask with the shutter open. The subject is allowed to acclimate to the mask, which may or may not be necessary based on their behavior. Panting is acceptable and in fact promotes more rapid thermal equilibration and equilibration of expired with inspired gases in the tubing.

Figures 27A, 27B:
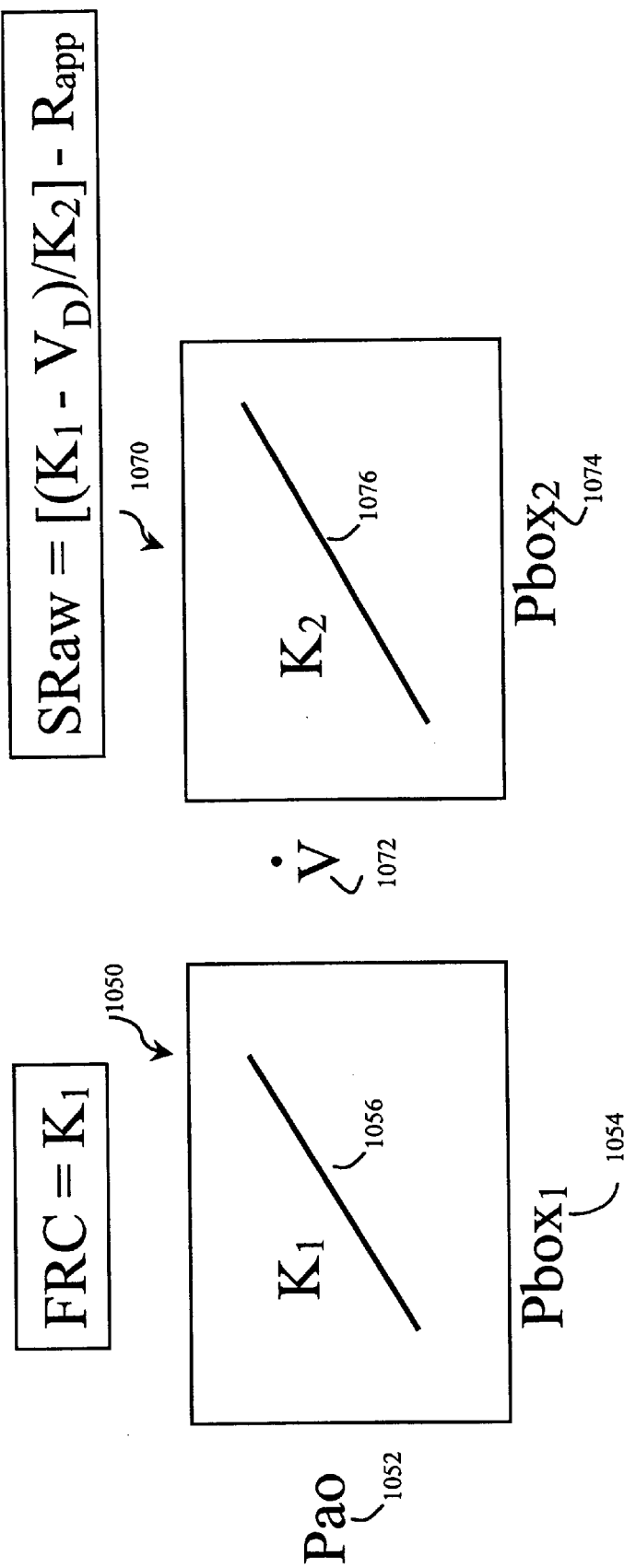
FIGS. 27A and 27B graphically illustrate the relationship of airway pressure with respect to chamber pressure and flow in relation to chamber pressure respectively.

The shutter is closed per step 1106 at end-expiration of the subject, and while the subject continues to make small efforts against the closed shutter, an X-Y plot of Pbox 1054 and Pao 1052 which is indicative of the pressure in the facemask is generated. The slope of this X-Y plot 1056 is employed as a correction factor in the measurement of airway resistance. The X-Y slope is recorded using, for example, an oscilloscope or commercial data acquisition system such as Buxco XA Biosystem for Windows, provided by Buxco Electronics of Sharon, Conn. The Pbox (Pboxi) is plotted on the X and the Pao on the Y axis for this purpose. FIG. 27A illustrates this curve.

The other purpose of measuring this slope is for the measurement of functional residual capacity (FRC). However, the $Pbox_1$ must first be calibrated relative to a known volume. This can be readily achieved by injecting a known volume into the box, and measuring the pressure change. The calculation of FRC uses Boyle's law. During occlusion, the subject makes efforts to breathe. The calculation can be made as follows:

$$\text{delta}V \text{ (in ml)/delta}Pbox \text{ (in cm H2O)} \times (Patm - PH_2O)/1000;$$

units being liters (L).

The next step 1112 includes the measurement of specific airway resistance (sRaw). For this step, the shutter is opened per step 1110. The subject breathes through the extension back into the box. The Pbox is now a reflection of alveolar pressure which is the average pressure within the alveolar space. The measurement of resistance is generally defined as pressure divided by flow. In this case, instantaneous flow is measured at the airway opening (V'ao) 1072 with a pneumotachometer, and this flow is plotted against Pbox 1074 real-time as shown in FIG. 27B. The slope of this line 1076 is multiplied by the slope of the Vbox/Pbox$_1$ line generated during calibration. This provides a measure of specific airway resistance sRaw, a resistance that pertains to the compartment of airways proximal to the alveoli as opposed to pulmonary resistance, which includes the lung tissue pleura. sRaw is an important clinical measurement in any subject suspected of airway disease. Previous studies have shown that sRaw is a strong indicator of the level of bronchomotor tone in the lower airways. Because flow is measured at the airway opening, sRaw is a reflection of resistance of all the airways, including the upper and lower airways, and this measurement does not distinguish the location of the obstruction.

Per step 1114, flowmetric indices can be measured using the methods 1100, 1150 of the present invention. The box extension is capped off using a stopcock or shutter on both ends, and the subject continues to breath via facemask to the atmosphere per step 1113. The instantaneous flow or nasal flow is compared to the volume displacement at the body surface measured and previously calibrated with a known volume as pressure changes in the box, and characterized as thoracic flow. Instantaneous nasal and thoracic flows are compared to obtain indices of airway obstruction. The advantage of coupling flowmetric measurements with plethysmography is that additional information is obtained. The flowmetric indices allow a clinician to distinguish airway obstruction that is evidenced during the inspiratory as opposed to the expiratory phase of breathing. This helps to localize a lesion, since many upper airway obstructions cause dynamic inspiratory resistance, and lower airway obstructions result in dynamic obstruction principally during expiration. Some lesions result in both upper and lower, or both inspiratory and expiratory abnormalities in resistance.

The system 1000 in accordance with the present invention is useful to specialists but in no way restricts the operation to specialists in the field of pulmonology. Since the application is friendly enough, a technician can be trained to perform all the tests, leaving the interpretation of the data to the clinician, specialist, or researcher. In a preferred embodiment, a data port for remote real-time or post-hoc or acquisition analysis over the internet is provided.

The preferred embodiments of systems of the present invention may find applications in specialized veterinary hospitals, and research laboratories. The system 1000 can be constructed at different levels of complexity, particularly in the user interface. For example, a data acquisition system can be provided per a preferred embodiment which is user-friendly, involving an automated and four point calibration of pneumotachograph flow, pressure of the box for FRC, pressure of the box for sRaw, pressure of the airway with automatic recording of box temperature, pressure, and humidity. In yet another embodiment, a more sophisticated calibration that stores data in a format that is compatible with good laboratory practices is provided. The former system is a touch screen, the latter computer based. Although these user interfaces and software used to acquire data are not necessary to define the embodiments of the present invention, it is relevant perhaps to consider that a full array of user-interfaces would make the system of the present invention more marketable.

A preferred embodiment of the system 1000 of the present invention is directed to providing measurements in larger animals. The preferred embodiment of the system 1000 in accordance with the present invention can be assembled on-site by a specialist, and tested for accuracy on-site using a mechanical model of the respiratory system, and by measuring sRaw and FRC in a sampling of healthy subjects. Once assembled, the system 1000 weighs less than approximately 30 lbs and may be placed on a moveable cart. The cart may have an hydraulic lift if the user wants to elevate the subject off the ground to a desirable height and has wheels to be easily moveable. The hardware components, for example, the amplifier interface and power unit can be attached to the cart or kept separate as a second cart or reside on a stationary piece of office furniture. Mobility is an advantage for some users, since the system can be used in multiple areas of a pharmaceutical campus, for instance.

Figure 30:
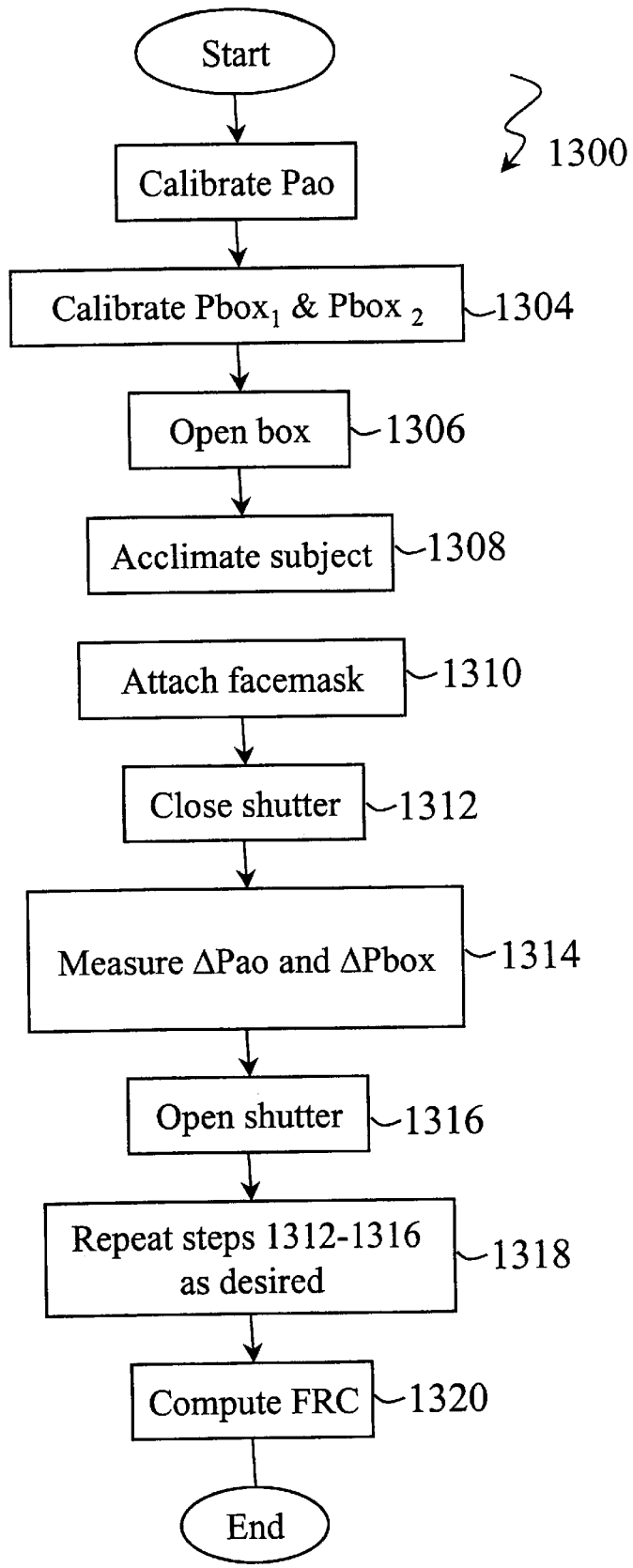
FIG. 30 is a flow chart illustrating the details of the functional residual capacity (FRC) measurement in accordance with a preferred embodiment as illustrated in FIG. 28.

FIG. 30 is a flowchart that provides the details of a preferred embodiment of the method 1300 of computing the functional residual capacity (FRC) using the system described in FIGS. 26A–C, 28, and 29. The method 1300 begins by calibrating Pao indicative of the airway flow at the facemask of the subject using a manometer per step 1302. The pressure transducers Pbox$_1$ and Pbox$_2$ are then calibrated separately using know volumes injected into the box or chamber per step 1304. Thus, Pbox$_1$ and Pbox$_2$ are calibrated and correlated to a differential volume measure (Pbox$_1$ and Pbox$_2$=KV$_{1\ or\ 2}$).

The chamber is then opened per step 1306 and subject is introducted into the chamber. Per step 1308, the subject acclimates to the chamber for approximately 1 to 5 minutes. The chamber is then closed. The facemask is then attached per step 1310. The shutter of the movable shutter assembly is then closed at the end of the exhalation per step 1312 which correlates to FRC. The differential airway pressure ΔPao and differential box pressure ΔPbox$_1$ are then measured per step 1314. The airway measure (Pao) is inversely proportional to the pressure in the chamber. The box pressure is converted to a volume measure per the earlier calibration. The shutter assembly is then opened per step 1316. Step 1318 includes the repetition of steps 1312–1315 as desired.

The FRC parameter is measured per step 1320. The change in volume is divided by a change in airway pressure.

$$FRC = \frac{\Delta V_{1\max}}{\Delta Pao_{\max}}(P_{atm} - P_{H2O})$$

Thus, pressure changes in the chamber are calibrated with known volume measures and provide an absolute measure of thoracic volume or change in lung volume. The units of FRC are typically in liters.

Figure 31:
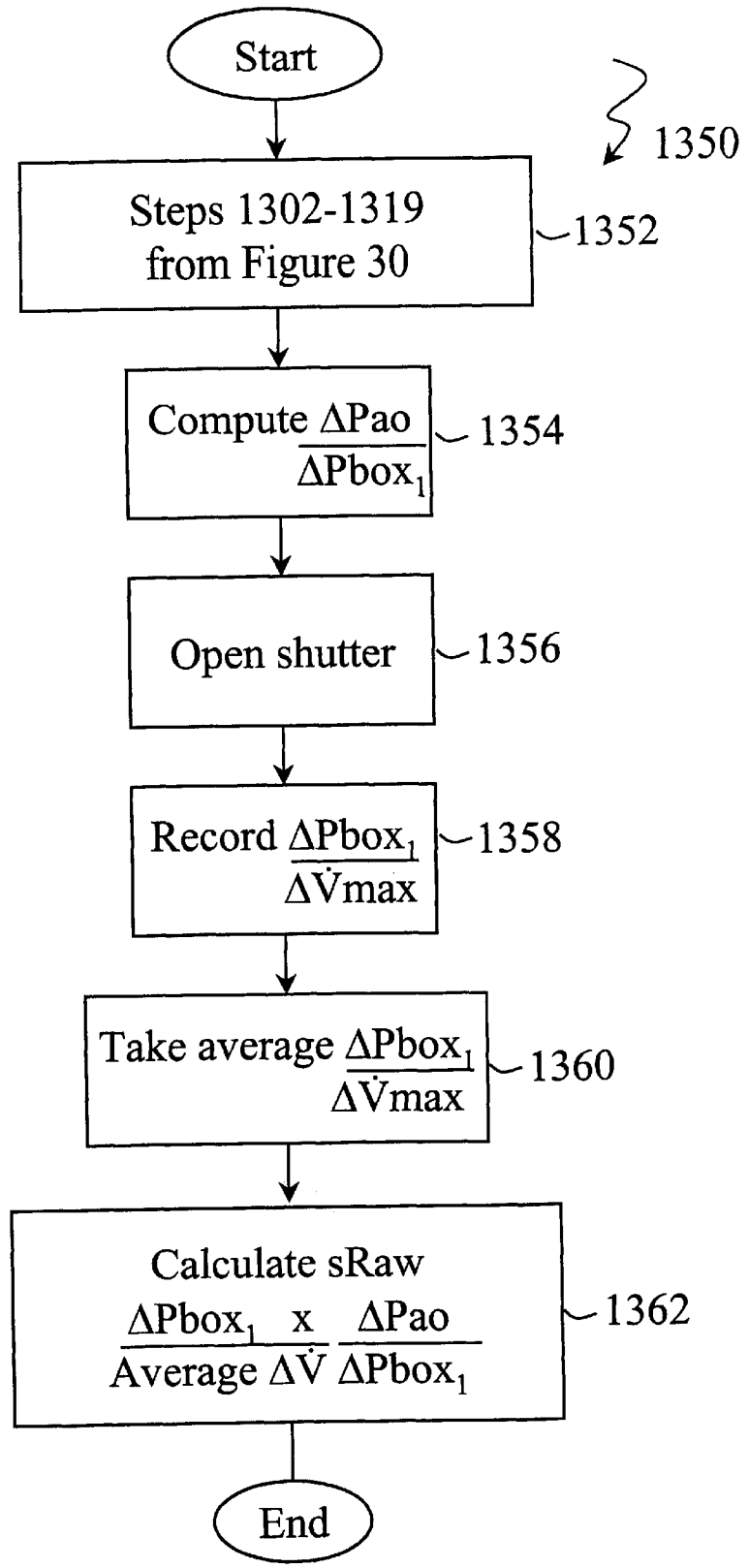
FIG. 31 is a flow chart illustrating the details of the airway resistance measurement in accordance with a preferred embodiment of the present invention as illustrated in FIGS. 28 and 29.

FIG. 31 is a flow chart that provides the details of a preferred embodiment of the method 1350 to compute airway resistance (sRaw) using the system described in FIGS. 26A–C, 28 and 29. The method 1350 begins after the steps 1302 through 1318 as detailed in the FIG. 30. The method 1350 then includes the computation of the ratio of the differential box pressure and differential airflow measure per step 1354, $$\left(\frac{\Delta Pao}{\Delta Pbox_1}\right).$$

The shutter assembly is then opened per step 1356 and the subject now is breathing back into the box. The ratio of the differential airflow measure and the differential box pressure are measured and recorded $$\left(\frac{\Delta Pbox_1}{\Delta \dot{V} \max}\right).$$

Per step 1358 an average value is determined for the ratio $$\left(\frac{\Delta Pbox_1}{\Delta \dot{V} \max}\right)$$

over several breaths.

The value of the airway resistance sRaw is then computed in step 1360 by multiplying the average value calculated in step 1358 with the correction factor calculated in step 1314 of FIG. 30. Thus, $$SRaw = \frac{\Delta Pbox_1}{\Delta \dot{V}} \times \frac{\Delta Pao}{\Delta Pbox_1}.$$

Figure 32:
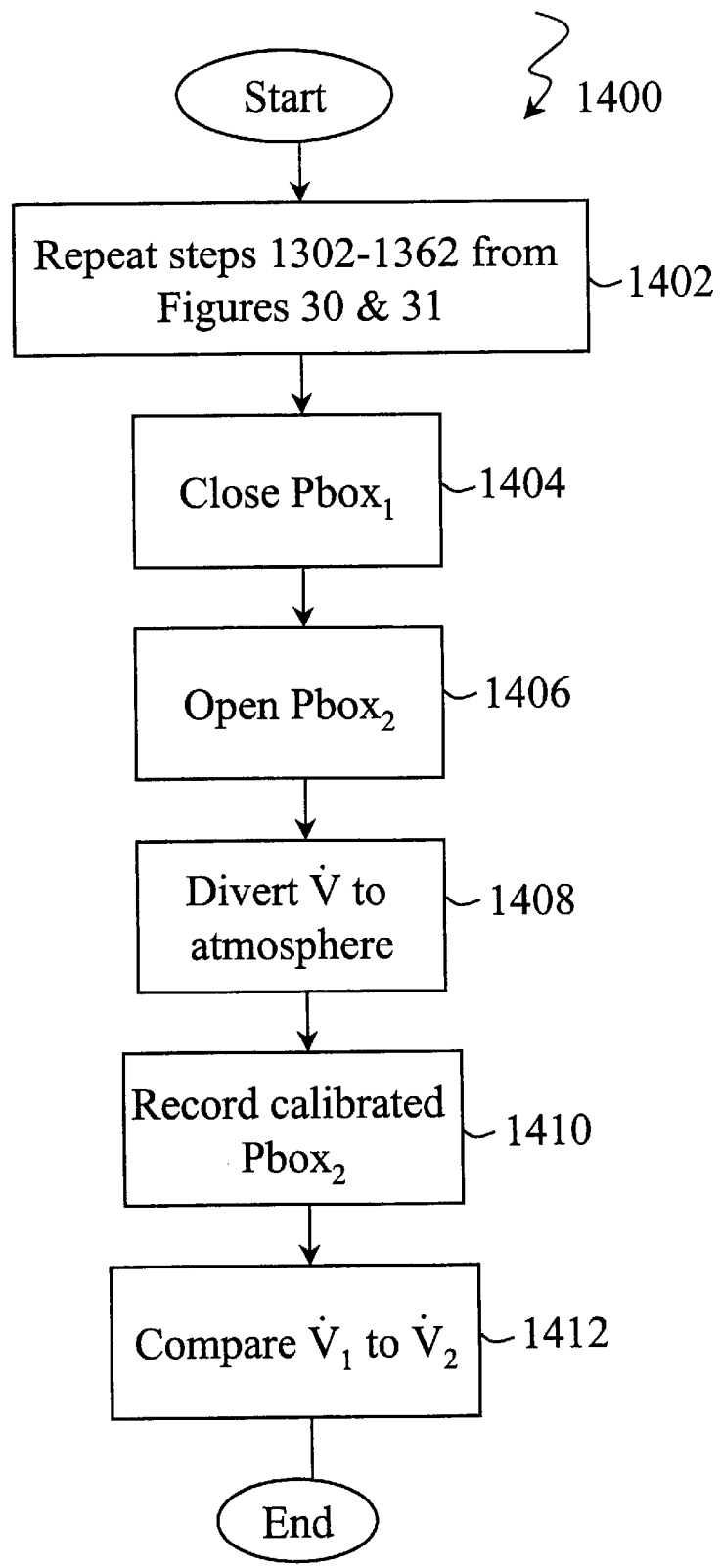
FIG. 32 is a flow chart illustrating the details of the flowmetric variables in accordance with a preferred embodiment of the present invention as illustrated in FIG. 28.

FIG. 32 is a flowchart detailing the methods to measure and calculate flowmetric variables in accordance with preferred embodiments of the present invention as described with respect to FIGS. 226A–C, 28 and 29. The method 1400 begins after the steps detailed in FIGS. 30 and 31. In step 1404 $Pbox_1$ is closed using a stopcock mechanism. Per step 1406, $Pbox_2$ is opened and allows a measure of flow at the airway opening. The method 1400 then proceeds to step 1408 wherein the flow is diverted to atmosphere and thus no expired gas is introduced into the chamber. In step 1410, calibrated $Pbox_2$ values as differentiated into volume ($\dot{V}_2$) is recorded. The flows ($\dot{V}_1$ and $\dot{V}_2$) derived from the two pressure transducers is then compared per step 1412 to derive flowmetric variables. Thus, the system 1000 is accordance to a preferred embodiment of the present invention allows the correlation of pressure changes to volume, which in turn are differentiated to provide signals indicative of flow at the mouth and thorax. The dynamic comparison of these flows provides a characterization of airway obstructions.

Figure 33:
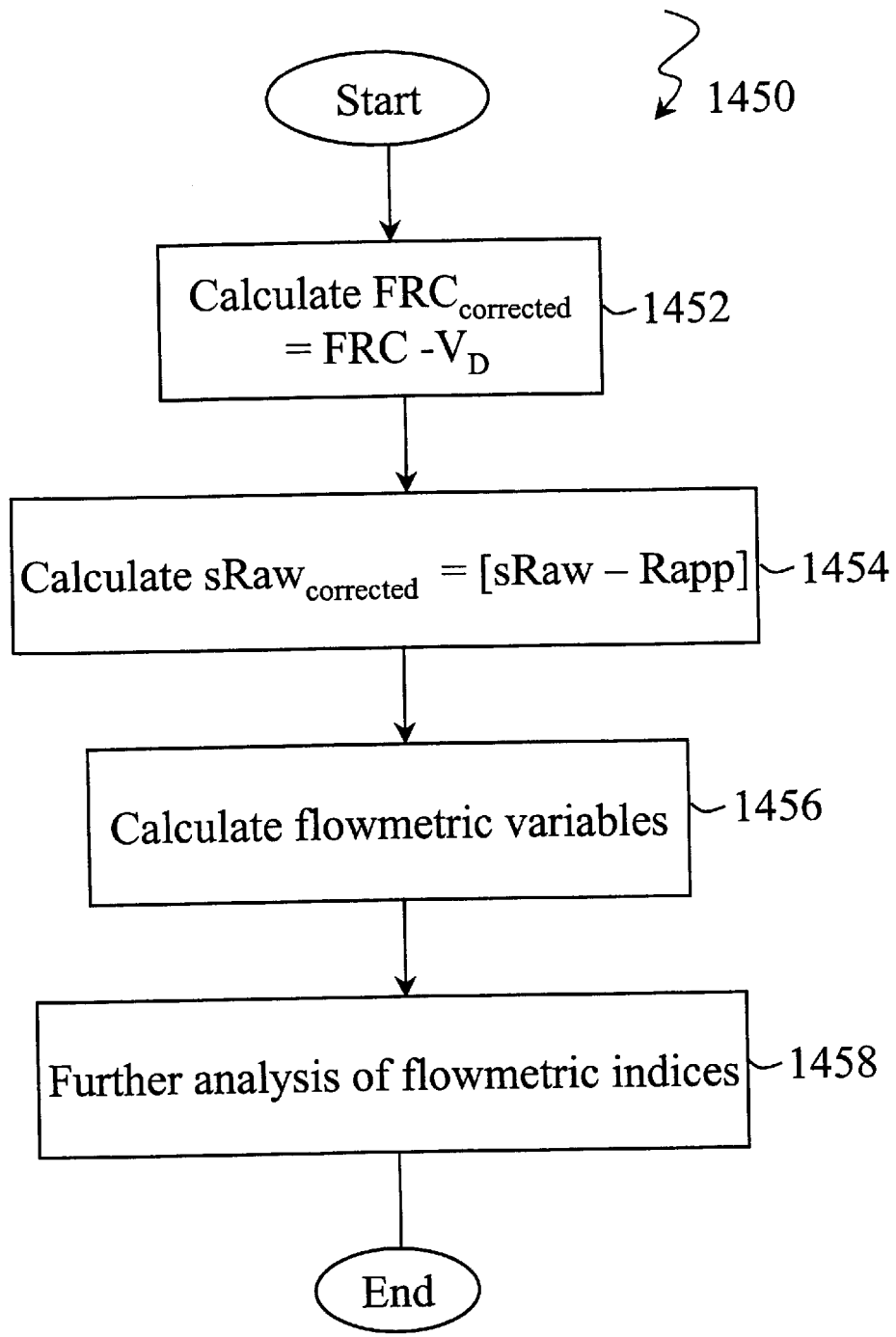
FIG. 33 is a flow chart illustrating the post-aquisition analysis performed in accordance with a preferred embodiment of the present invention.

FIG. 33 is a flow chart that details post-acquisition analysis that may be performed in accordance with a method 1450 of measuring respiratory function as described with respect to FIGS. 26A–C, 28 and 29 of the present invention. The method 1450 includes step 1452 wherein the FRC measurement is corrected for aberration added by the apparatus ($V_D$) such as, for example, subtracting the dead space of the shutter assembly, facemask and the subject's upper airway. Thus, $FRC_{corrected} = FRC - V_D$. The FRC measurement is corrected for body weight, FRC/kg bodyweight. Typically a range of approximately 30 to 40 ml/kg bodyweight is corrected for any test subject.

The method 1450 then proceeds to step 1454 for correcting the resistance measure: $sRaw_{corrected} = [sRaw - Rapp]$ wherein the resistance of the apparatus such as, for example, the flowmeter and plumbing tubing, is subtracted from the measured sRaw. In step 1456, the flowmetric variables are then computed and corrected. The variables associated with the expiratory phase of breathing ($SFE_{max}$ and $SFE_{intx}$) which are the area difference between $\dot{V}_1$ and $\dot{V}_2$ during prescribed portions of expiration as defined by the $\dot{V}_2$ signal are corrected for bodyweight. Similarly the variable associated with the inspiratory phase of breathing ($SFI_{max}$, $SFI_{Intx}$) are corrected. Further, flowmetric variable that may be corrected include, for example, but are not limited to respiratory frequency tidal volume, peak flows and minute ventilation.

The method 1450 may include the step of 1458 which comprises further analysis of these flowmetric indices such as, for example, the use of Fourier analysis such as Fast Fourier Transforms. This provides for a study of frequency dependent respiratory function characteristics.

Further, since the head-out plethysmograph system affords a variety of measurements, these measurements can be packaged as a pulmonary function testing panel by an operator, for reporting by the interpreter be it a specialist, a clinician, or a researcher. New variables from the flowmetric variable analysis of the system of the present invention may include, for example, peak and area differences between nasal and thoracic volumes and flows in selected segments of the breath, such as inspiratory and expiratory measurements, and measurements in the first portion of inspiration or expiration. Further, X-Y plots of nasal and thoracic signals (flow-volume measurements) may provide insights into thoracic flow as related to nasal volume, and nasal flow in relation to nasal volume. The corrected values of peak and area differences above—i.e., normalized for body weight, lung volume as measured by the pneumotach (nasal), and/or FRC may also be generated. In addition, Fast Fourier Transformations (FFT) and transfer function analysis of the nasal versus thoracic volume or flow signals, classic variables also measured with plethysmography, specific airway resistance, and functional residual capacity (FRC) may be generated.

Further data that may be generated using the methods of the present invention include FRC corrected for body weight (FRC/kg bwt) compatible measurements not requiring the plethysmograph, but requiring additional equipment such as, for example, a three way non-rebreathing valve or rebreathing bags, fast-frequency gas analyzers (He, CO, $O_2$, $CO_2$), non-diffusible gas collection bags, and a capnograph, venturi tube or other methods for indirect calorimetry, with appropriate sampling ports. The subject can remain in the plethysmograph during tests and provide the following additional data: end-tidal $CO_2$, mixed expired $CO_2$, inspired gas fractions, dead space to tidal volume ratio, diffusion capacity for carbon monoxide by steady state or rebreathing methods (DLCO), indirect calorimetry such as resting energy requirements (RER), respiratory quotient, (RQ), V'O2, V'CO2 and FRC by Helium dilution if occlusions are unsuccessful. Specific tests may be selected depending upon the test subject and the diagnosis. A report is then generated including an interpretation by the specialist/clinician/researcher.

The systems and methods in accordance with the preferred embodiment of the present invention address clinical respiratory disease which is highly prevalent in animals and humans. Respiratory diseases are generally divided up into those that involve the airways (upper or lower), the lung tissue (alveoli), the breathing pump (chest wall, diaphragm) and neuromuscular connections and the brain. In addition there are neuromuscular diseases, for example, botulism, myasthenia gravis that are considered. The plethysmographic system in accordance with the present invention is relevant to all causes of respiratory disease. These diseases appear similar, that is as an animal in apparent respiratory distress or intolerant of exercise or movement. To sort out the location of the lesion, one needs specific prescribed tests. Since the subjects are typically compromised or sick it is important that the tests do not exacerbate the illness due to excessive movements or stress or anesthesia. The ancillary tests, such as radiography, endoscopy, and arterial blood gases are important, but do not consistently localize the disease, especially if the lung (lower airways and alveoli) are involved. In addition, the ancillary tests do not quantify the extent or severity of the pathology in many circumstances.

The plethysmograph system in accordance with the preferred embodiments of the present invention, if used to measure flowmetric data and classical measures of sRaw and FRC, allows for the specific localization of the problem. For example, in the case of dogs with idiopathic lung fibrosis, where the alveoli are diseased but the airways are spared of pathology, there are marked changes in FRC, without changes in sRaw. The opposite is true in cases of asthma or bronchitis. In emphysema, there are increases in FRC and minor increases or no change in sRaw. The flowmetric data further allows one to distinguish if abnormalities of the airways are localized in the upper airways or lower airways, and if they are fixed or dynamic obstructions. For example, an intrathoracic collapsing trachea, would result in abnormalities principally in the expiratory flowmetric data (increased peak and area differences between thoracic and nasal volumes and flows during expiration), with little or no change in inspiratory data. This enhances the measure of sRaw, which is more or less an average of inspiratory and expiratory resistance. Although there are prior art methods for computing inspiratory versus expiratory resistance using plethysmography, these do not allow one to visualize these differences, and are complicated requiring specific algorithms that are untested. Therefore, the combination of flowmetric data and classical measures of sRaw and FRC as derived from the preferred embodiments of the present invention reveal important characteristics and further the diagnosis of specific respiratory problems. The addition of compatible measurements, especially DLCO, dead-space to tidal volume ratio, and indirect calorimetry allows even further understanding of complex processes, such as pulmonary vascular disease, that lowers DLCO and increases dead-space/tidal volume ratio without changing flowmetric data or classical measures of sRaw and FRC, in most cases. The subject with dyspnea may have an underlying airway, alveolar, vascular, or breathing pump problem, each of which requires a specific treatment. The preferred embodiment systems in accordance to the present invention are non-invasive, comprehensive, and based in credible physiologic theory.

While this invention has been particularly shown and described with references to preferred embodiments thereof, it will be understood by those skilled in the art that various changes in form and details may be made therein without departing from the spirit and scope of the invention as defined by the appended claims.

What is claimed:

1. A method for characterizing airway obstruction of a conscious living organism, comprising the steps of:
   obtaining a first input signal using a constant volume plethysmograph system having a head-out, breath-in chamber, the first input signal being a pressure differential signal indicative of alveolar pressure during breathing by said living organism in a chamber;
   obtaining a second input signal from a second sensor indicative of nasal airflow of said living organism; and
   processing said first input signal and said second input signal to calculate at least a third signal indicative of airway resistance; and
   characterizing airway obstructions of said living organism using the at least third signal.

2. The method according to claim 1, wherein the processing step comprises the step of comparing said first input signal to said second input signal.

3. The method according to claim 2, wherein the step of comparing said first and second input signals comprises analyzing phase and magnitude differences between said first and second signals in the same time domain.

4. The method according to claim 3, wherein the step of comparing said first and second input signals further comprises the step of subtracting said second input signal from said first input signal.

5. The method according to claim 1, further comprising of obtaining the first input signal through use of at least one of respiratory induction plethysmography, an optoelectronic plethysmograph and a fiber optic respiration plethysmograph.

6. The method according to claim 1, further comprising of obtaining the first input signal through use of impedance plethysmography.

7. The method according to claim 1, further comprising of obtaining the second input signal through use of a pneumotachographic measurement device.

8. The method according to claim 1, further comprising of obtaining the second input signal through use of an ultrasonic device.

9. The method according to claim 1, further comprising of obtaining the second input signal through use of a thermistor.

10. The method according to claim 1, further comprising of obtaining the second input signal through use of a breath-sound intensity device.

11. The method according to claim 1, further comprising the step of calibrating first input signal.

12. The method according to claim 1, further comprising the step of administering a medication to the living organism to alter the respiratory function.

13. The method according to claim 1, further comprising of administering a bronchodilators medication.

14. The method according to claim 1, further comprising calculating a plurality of signals indicative of respiratory function comprising at least one of functional residual capacity, airway resistance, diffusion capacity peak and area differences during expiration, peak and area differences during inspiration and corrected values thereof.

15. The method according to claim 1, further comprising measuring airway obstructions during inspiration and expiration.

16. The method of claim 1, wherein the constant volume plethysmograph comprises at least one adjustable volume chamber.

17. The method of claim 16, further comprising a data collection system in communication with the chamber.

18. The method of claim 16, further comprises controlling the environment of the chamber.

19. A method for characterizing airway obstruction of a conscious living organism comprising the steps of:
   obtaining a first input signal indicative of a change in lung volume as related to a pressure change in a constant volume, head out, breath in plethysmograph chamber;
   converting said first input signal from an analog signal to a digital signal;
   taking the derivative of said digital first input signal to generate a signal indicative of thoracic flow;
   converting the second input signal from an analog to a digital signal;
   taking the derivative of the second input signal to generate a signal indicative of nasal airflow; and
   dynamically comparing the signals indicative of thoracic flow and nasal airflow.

20. The method according to claim 19, further comprising measuring airway obstructions during inspiration and expiration.

21. The method according to claim 19, wherein the constant volume plethysmograph comprises at least one adjustable volume chamber.

22. The method according to claim 19, further comprising controlling the environment of the chamber.

23. The method according to claim 19, wherein the living organism is a canine.

24. The method according to claim 19, further comprising further processing the first input signal and second input signal to calculate a plurality of signals indicative of respiratory function.

25. A system for characterizing airway obstruction of a conscious mammal, comprising:
   a constant volume plethysmograph having at least one head out, breath in chamber having a plurality of sensors disposed therein, and
   a data collection and processing system in communication with the constant volume plethysmograph.

26. A system of claim 25 wherein the constant volume plethysmograph further comprises at least one pressure sensor to obtain a first input signal indicative of alveolar pressure of the conscious mammal; and
   a device that obtains a second input signal indicative of nasal flow.

27. The system of claim 25, wherein the first and second input signals are processed in the data collection and processing system to calculate a plurality of signals indicative of respiration function.

28. An apparatus for measuring airway obstructions in a conscious mammal, comprising:
   at least one chamber having a constant volume and at least one pressure sensor to obtain a first input signal indicative of alveolar pressure of the conscious mammal, the at least one chamber provides for a head-out breath-in configuration for the conscious mammal;
   a device to obtain a second input signal indicative of nasal flow, and
   a processing device in communication with the chamber to calculate a third signal by comparing the first and second input signals to characterize airway obstructions of the mammal.

29. The apparatus of claim 28, wherein the at least one chamber further comprising a tube to couple expired air from the conscious mammal into the chamber.

30. The apparatus of claim 28, wherein the at least one chamber comprises a constant volume plethysmographic measurement device.

31. The apparatus of claim 30, wherein the pneumotachographic measurement device comprises at least one of screen type, Fleisch, ultrasonic and turbine devices.

32. The apparatus of claim 28, wherein the device comprises a pneumotachographic measurement device.

33. The apparatus of claim 28, further comprising a heating device in the chamber.

34. The apparatus of claim 28, further comprising a plurality of differential pressure transducers.

35. The apparatus of claim 28, further comprising at least one sensor to monitor the temperature, humidity and barometric pressure of the chamber.

36. The apparatus of claim 28, wherein the processing device further comprises a programmable computer.

37. The apparatus of claim 28, wherein the apparatus is portable and weighs less than 30 pounds.

38. The apparatus of claim 28, wherein the volume of the at least one chamber is adjustable.

39. The apparatus of claim 28, wherein the processing device compares the first and second input signals in the same time domain.

40. A portable apparatus for measuring pulmonary function in a conscious mammal, comprising:
   at least one headout, breath in chamber having a constant volume and at least one pressure sensor to obtain a first input signal indicative of alveolar pressure of the conscious mammal;
   a device to obtain a second input signal indicative of nasal flow, and
   a processing device in communication with the chamber to calculate a third signal by comparing the first and second input signals to characterize airway obstructions of the mammal.

41. The apparatus of claim 40, wherein the at least one chamber provides for a head-out configuration for the conscious mammal; the at least one chamber having a tube to couple expired air from the conscious mammal into the chamber.

42. The apparatus of claim 40, wherein the at least one chamber comprises a constant volume plethysmographic measurement device.

43. The apparatus of claim 40, wherein the device comprises a pneumotachographic measurement device.

44. The apparatus of claim 40, further comprising a heating device in the chamber.

45. The apparatus of claim 40, further comprising a plurality of differential pressure transducers.

46. The apparatus of claim 42, wherein the pneumotachographic measurement device comprises at least one of screen type, Fleisch, ultrasonic and turbine devices.

47. The apparatus of claim 42, further comprising at least one sensor to monitor the temperature, humidity and barometric pressure of the chamber.

48. The apparatus of claim 42, wherein the processing device further comprises a programmable computer.

49. The apparatus of claim 42, wherein the apparatus weighs less than 30 pounds.

50. The apparatus of claim 42, wherein the volume of the at least one chamber is adjustable.

51. The apparatus of claim 42, wherein the processing device compares the first and second input signals in the same time domain.

* * * * *